(12) United States Patent
Furet et al.

(10) Patent No.: US 8,389,526 B2
(45) Date of Patent: Mar. 5, 2013

(54) 3-HETEROARYLMETHYL-IMIDAZO[1,2-B]PYRIDAZIN-6-YL DERIVATIVES

(75) Inventors: Pascal Furet, Thann (FR); Clive McCarthy, Froidefontaine (FR); Joseph Schoepfer, Riehen (CH); Stefan Stutz, Basel (CH)

(73) Assignee: Novartis AG, Basel (CH)

( * ) Notice: Subject to any disclaimer, the term of this patent is extended or adjusted under 35 U.S.C. 154(b) by 49 days.

(21) Appl. No.: 12/849,642

(22) Filed: Aug. 3, 2010

(65) Prior Publication Data

US 2011/0039831 A1    Feb. 17, 2011

Related U.S. Application Data

(60) Provisional application No. 61/273,756, filed on Aug. 7, 2009.

(51) Int. Cl.
    *A01N 43/58*      (2006.01)
    *A61K 31/50*      (2006.01)
    *C07D 487/00*      (2006.01)

(52) U.S. Cl. .................................. 514/250; 544/236

(58) Field of Classification Search ............... 544/236; 514/250
See application file for complete search history.

(56) References Cited

U.S. PATENT DOCUMENTS

| | | | |
|---|---|---|---|
| 3,489,755 A | 1/1970 | Lombardino et al. |
| 4,910,199 A | 3/1990 | Bourguignon et al. |
| 7,346,325 B2 | 3/2008 | Maeda et al. |
| 7,750,000 B2 | 7/2010 | Prien et al. |
| 2004/0082781 A1 | 4/2004 | Hibi et al. |
| 2006/0148801 A1 | 7/2006 | Hsieh et al. |
| 2007/0167460 A1 | 7/2007 | McArthur et al. |
| 2007/0265272 A1 | 11/2007 | Cheng et al. |
| 2008/0039457 A1 | 2/2008 | Zhuo et al. |
| 2008/0153813 A1 | 6/2008 | Chen et al. |
| 2009/0124609 A1 | 5/2009 | Albrecht et al. |
| 2009/0264406 A1 | 10/2009 | Furet et al. |

FOREIGN PATENT DOCUMENTS

| | | |
|---|---|---|
| EP | 306408 A1 | 3/1992 |
| EP | 490587 A1 | 6/1992 |
| EP | 1277754 B1 | 1/2003 |
| JP | 2009-227599 | 11/2009 |
| WO | WO 01/83461 A1 | 11/2001 |
| WO | WO 02/062800 A1 | 8/2002 |
| WO | WO 2004/058749 A1 | 7/2004 |
| WO | WO 2005/004607 A1 | 1/2005 |
| WO | WO 2005/004808 A2 | 1/2005 |
| WO | WO 2005/010005 A1 | 2/2005 |
| WO | WO 2005/041971 A1 | 5/2005 |
| WO | WO 2005/051906 A2 | 6/2005 |
| WO | WO 2005/073224 A2 | 8/2005 |
| WO | WO 2005/080355 A1 | 9/2005 |
| WO | WO 2006/124354 A2 | 11/2006 |
| WO | WO 2007/013673 A1 | 2/2007 |
| WO | WO 2007/038314 A2 | 4/2007 |
| WO | WO 2007/064797 A2 | 6/2007 |
| WO | WO 2007/075567 A1 | 7/2007 |
| WO | WO 2007/138472 A2 | 12/2007 |
| WO | WO 2008/008539 A2 | 1/2008 |
| WO | WO 2008/016192 A2 | 2/2008 |
| WO | WO 2008/030579 A2 | 3/2008 |
| WO | WO 2008/030744 A2 | 3/2008 |
| WO | WO 2008/051805 A2 | 3/2008 |
| WO | WO 2008/054157 A1 | 5/2008 |
| WO | WO 2008/155378 A1 | 12/2008 |
| WO | WO 2009/017954 A1 | 2/2009 |
| WO | WO 2009/060197 A1 | 5/2009 |
| WO | WO 2009/066955 A2 | 6/2009 |

*Primary Examiner* — Paul V. Ward
(74) *Attorney, Agent, or Firm* — Scott W. Reid

(57) ABSTRACT

The invention relates to compounds of formula (I) and salts thereof (I)

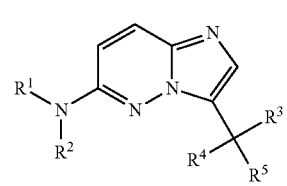

wherein the substituents are as defined in the specification, the application of a compound of formula (I) in a process for the treatment of the human or animal body, in particular with regard to C-Met tyrosine kinase mediated disease; the use of a compound of formula (I) for manufacturing a medicament for the treatment of such diseases; pharmaceutical compositions comprising a compound of the formula (I), optionally in the presence of a combination partner; processes for the preparation of a compound of formula (I).

9 Claims, No Drawings

3-HETEROARYLMETHYL-IMIDAZO[1,2-B]PYRIDAZIN-6-YL DERIVATIVES

The invention relates to 3-heteroarylmethyl-imidazo[1,2-b]pyridazin-6-yl derivatives of the formula (I) given below, as well as salts thereof; the application of a compound of formula (I) in a process for the treatment of the human or animal body, in particular with regard to a proliferative disease; the use of a compound of formula (I) for manufacturing a medicament for the treatment of such diseases; pharmaceutical compositions comprising a compound of the formula (I), optionally in the presence of a combination partner; and processes for the preparation of a compound of formula (I).

The Hepatocyte Growth Factor Receptor, herein referred to as c-Met, is a receptor tyrosine kinase that has been shown to be over-expressed and/or genetically altered in a variety of malignancies, specifically, gene amplification and a number of c-Met mutations are found in various solid tumors, see e.g. WO2007/126799. Further, the receptor tyrosine kinase c-Met is involved in the processes of migration, invasion and morphogenesis that accompany embryogenesis and tissue regeneration. C-met is also involved in the process of metastasis. Several lines of evidence have indicated that c-Met plays a role in tumor pathogenesis. Gain of function germ line mutations in c-Met is associated with development of hereditary papillary renal cell carcinoma (PRCC). Amplification or mutations in c-Met have also been reported in sporadic forms of PRCC, in head and neck squamous cell carcinoma, in gastric carcinoma, in pancreatic carcinoma and in lung cancer. Such alterations have been shown in selected instances to confer dependence of the tumor on c-Met and/or resistance to other targeted therapies. Elevated levels of c-Met, together with its unique ligand HGF/SF, are observed at high frequency in multiple clinically relevant tumors. A correlation between increased expression and disease progression, metastases and patient mortality has been reported in several cancers, including bladder, breast, squamous cell carcinoma and gastric carcinoma as well as leiomyosarcoma and glioblastoma.

WO 2008/008539 discloses certain fused heterocyclic derivatives which are useful in the treatment of HGF mediated diseases. WO 2007/013673 discloses fused heterocyclic derivatives as Lck inhibitors which are useful as immunosuppressive agents. EPO490587 discloses certain pyrazolopyrimidines which are useful as angiotensin II antagonists.

It is thus an aim of the present invention to provide further compounds that modulate (in particular inhibit) c-Met.

It has now been found that the compounds of the formula (I) given below have advantageous pharmacological properties and inhibit, for example c-Met. The compounds of formula (I) given below preferably show improved solubility and/or reduced cytochrome P450 inhibition hence reduced potential to lead to drug-drug interactions. Hence, the compounds of formula (I) are suitable, for example, to be used in the treatment of diseases dependent on c-Met activity, especially solid tumors or metastasis derived therefrom. Through the inhibition of c-Met, compounds of the invention may also have utility as anti-inflammatory agents, for example for the treatment of an inflammatory condition, for example, which is due to an infection.

The present invention provides a compound of formula (I),

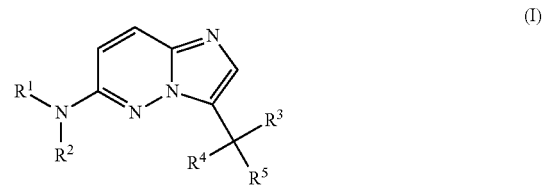

wherein
$R^1$ and $R^2$ together with the nitrogen to which they are attached form a 6 or 7 membered saturated monocyclic group comprising 1 ring N atom to which $R^1$ and $R^2$ are attached, and optionally 1 additional ring N atom, wherein said monocyclic group is unsubstituted or substituted one or more times by a substituent independently selected from $C_1$-$C_7$-alkyl, $C_3$-$C_{12}$-cycloalkyl, halo-$C_1$-$C_7$-alkyl, amino-$C_1$-$C_7$-alkyl, $C_1$-$C_7$-alkylcarbonyl, $C_1$-$C_7$-alkoxycarbonyl, formyl, aminocarbonyl, amino-$C_1$-$C_7$-alkyl-carbonyl, halo-$C_1$-$C_7$-alkylcarbonyl, halo-$C_1$-$C_7$-alkoxycarbonyl, phenyl, pyridyl, oxo;
$R^3$ is hydrogen, hydroxy, halogen or $C_1$-$C_7$-alkyl;
$R^4$ is hydrogen, halogen or $C_1$-$C_7$-alkyl;
$R^5$ is indazolyl or quinolinyl, each being substituted by at least one halogen atom;
or a pharmaceutically acceptable salt or N-oxide thereof.

The following general definitions shall apply in this specification, unless otherwise specified:

A "compound of the invention", or "compounds of the invention", or "a compound of the present invention" means a compound or compounds of formula (I) as described herein.

As used herein, the terms "including", "containing" and "comprising" are used herein in their open, non-limiting sense.

Where the plural form (e.g. compounds, salts) is used, this includes the singular (e.g. a single compound, a single salt). "A compound" does not exclude that (e.g. in a pharmaceutical formulation) more than one compound of the formula (I) (or a salt thereof) is present.

"Treatment" includes prophylactic (preventive) and therapeutic treatment as well as the delay of progression of a disease, disorder or condition.

Halogen (or halo) denotes fluorine, bromine, chlorine or iodine, in particular fluorine or chlorine, especially fluorine. Halogen-substituted groups and moieties, such as alkyl substituted by halogen (halogenalkyl or haloalkyl) can be mono-, poly- or per-halogenated.

Any non-cyclic carbon containing group or moiety with more than 1 carbon atom is straight-chain or branched.

"Alkyl" refers to a straight-chain or branched-chain alkyl group. For example, $C_1$-$C_7$alkyl is alkyl with from and including 1 up to and including 7 carbon atoms and includes methyl, ethyl, n- or iso-propyl, n-, iso-, sec- or tert-butyl, n-pentyl, neo-pentyl, n-hexyl and n-heptyl, with particular preference given to methyl, ethyl, n-propyl, iso-propyl, n-butyl and iso-butyl. $C_1$-$C_4$alkyl is preferred. Alkyl may be unsubstituted or substituted. Exemplary substituents include, but are not limited to hydroxyl, alkoxy, halogen and amino. An example of a substituted alkyl is trifluoro-methyl.

Each alkyl part of other groups like "halo-$C_1$-$C_7$-alkyl", "amino-$C_1$-$C_7$-alkyl", "$C_1$-$C_7$-alkylcarbonyl", "$C_1$-$C_7$-alkoxycarbonyl", "amino-carbonyl", "amino-$C_1$-$C_7$-alkylcarbonyl", "halo-$C_1$-$C_7$-alkylcarbonyl", "halo-$C_1$-$C_7$-alkoxycarbonyl, shall have the same meaning as described in the above-mentioned definition of "alkyl".

"$C_3$-$C_{12}$-cycloalkyl" refers to a saturated or partially saturated, monocyclic, fused polycyclic, or spiro polycyclic, carbocycle having from 3 to 12 ring atoms per carbocycle. Illustrative examples of cycloalkyl groups include the following moieties: cyclopropyl, cyclobutyl, cyclpentyl and cylclohexyl. Cycloalkyl may be unsubstituted or substituted; exemplary substituents are provided in the definition for alkyl. $C_3$-$C_5$-cycloalkyl is preferred, for example cyclopropyl.

The invention may be more fully appreciated by reference to the following description, including the following glossary of terms and the concluding examples. As used herein, the terms "including", "containing" and "comprising" are used herein in their open, non-limiting sense.

$R^1$ and $R^2$ together with the nitrogen to which they are attached preferably form a 6 or 7 membered saturated monocyclic group comprising 1 ring N atom to which $R^1$ and $R^2$ are attached, and 1 additional ring N atom.

Examples of groups formed from $R^1$ and $R^2$ together with the nitrogen to which they are attached and including 1 additional ring N, include (but not limited to) piperazine (especially piperazin-4-yl) and diazepane (especially 1,4-diazepane, such as 1,4-diazepan-4-yl).

When substituted, the monocyclic group formed from $R^1$ and $R^2$ is preferably substituted by one, two or three substituents, independently selected from the group consisting of $C_1$-$C_7$-alkyl, $C_3$-$C_{12}$-cyclo-alkyl, amino-$C_1$-$C_7$-alkyl, $C_1$-$C_7$-alkylcarbonyl, $C_1$-$C_7$-alkoxycarbonyl, formyl, amino-carbonyl, halo-$C_1$-$C_7$-alkylcarbonyl, phenyl, pyridyl, oxo. Preferably, said substitutents are independently selected from the group consisting of $C_1$-$C_4$-alkyl, $C_3$-$C_5$-cyclo-alkyl, amino-$C_1$-$C_4$-alkyl, $C_1$-$C_4$-alkylcarbonyl, $C_1$-$C_4$-alkoxycarbonyl, formyl, amino-carbonyl, halo-$C_1$-$C_4$-alkylcarbonyl, phenyl, pyridyl, oxo. Especially preferred are substituents selected from methyl, cyclopropyl, methylcarbonyl, formyl, methoxycarbonyl, aminocarbonyl, trifluoromethylcarbonyl, phenyl, pyridyl and oxo.

When the monocyclic group formed from $R^1$ and $R^2$ is substituted on a ring carbon atom thereof, preferred substituents include $C_1$-$C_7$-alkyl (more preferably $C_1$-$C_4$-alkyl, most preferably methyl) and/or oxo (=O). In this respect, preferably, one, two or three ring carbon atoms, most preferably 2 ring carbon atoms, are substituted.

Preferably, when the said 1 additional ring N is substituted, preferred substituents are selected from the group consisting of $C_1$-$C_7$-alkyl, $C_3$-$C_{12}$-cyclo-alkyl, amino-$C_1$-$C_7$-alkyl, $C_1$-$C_7$alkylcarbonyl, $C_1$-$C_7$-alkoxycarbonyl, formyl, amino-carbonyl, halo-$C_1$-$C_7$-alkylcarbonyl, phenyl, pyridyl. Preferably, said substitutents are independently selected from the group consisting of $C_1$-$C_4$-alkyl, $C_3$-$C_5$-cyclo-alkyl, amino-$C_1$-$C_4$-alkyl, $C_1$-$C_4$-alkylcarbonyl, $C_1$-$C_4$-alkoxycarbonyl, formyl, amino-carbonyl, halo-$C_1$-$C_4$-alkylcarbonyl, phenyl, pyridyl. Especially preferred are substituents selected from methyl, cyclopropyl, methylcarbonyl, formyl, methoxycarbonyl, aminocarbonyl, trifluoromethylcarbonyl, phenyl, pyridyl.

In an embodiment of the invention, $R^1$ and $R^2$ together with the nitrogen to which they are attached form a group:

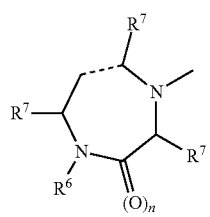

wherein, the dashed line is either absent (i.e. to form a piperazine ring) or is a single bond (i.e. to form a diazepane ring);

n is 0 or 1 (i.e. the oxo group is either present or absent);

$R^6$ is hydrogen or a group selected from $C_1$-$C_7$-alkyl, $C_3$-$C_{12}$-cycloalkyl, halo-$C_1$-$C_7$-alkyl, amino-$C_1$-$C_7$-alkyl, $C_1$-$C_7$-alkylcarbonyl, $C_1$-$C_7$-alkoxycarbonyl, formyl, amino-carbonyl, amino-$C_1$-$C_7$-alkyl-carbonyl, halo-$C_1$-$C_7$-alkylcarbonyl, halo-$C_1$-$C_7$-alkoxycarbonyl, phenyl, pyridyl; and each $R^7$ is independently selected from hydrogen, unsubstituted $C_1$-$C_7$-alkyl or substituted $C_1$-$C_7$-alkyl (e.g. halo-$C_1$-$C_7$-alkyl, amino-$C_1$-$C_7$-alkyl, hydroxy-$C_1$-$C_7$-alkyl);

$R^1$ and $R^2$ together with the nitrogen to which they are attached are very preferably 1-methyl-piperazin-4-yl-2-one, piperazin-4-yl-2-one, piperazin-1-yl, 4-methyl-piperazin-1-yl, 1-(4-piperazin-1-yl)-ethanone, piperazin-4-yl-1-carbaldehyde, piperazin-4-yl-1-carboxylic acid methyl ester, piperazin-4-yl-1-carboxylic acid amide, 1-(4-piperazin-1-yl)-2,2,2-trifluoro-ethanone, 3-methyl-piperazin-4-yl-2-one, [1,4]diazepan-1-yl-5-one, 1-cyclopentylpiperazin-4-yl-2-one, 1,3-dimethylpiperazin-4-yl-2-one, 1-phenylpiperazin-4-yl-2-one, 5-methylpiperazin-4-yl-2-one, 6-methylpiperazin-4-yl-2-one or 1-(pyridin-2-yl)piperazin-4-yl-2-one.

$R^3$ is preferably hydrogen or $C_1$-$C_7$-alkyl, more preferably hydrogen or $C_1$-$C_4$-alkyl, most preferably hydrogen or methyl.

$R^4$ is preferably hydrogen or $C_1$-$C_7$-alkyl, more preferably hydrogen or $C_1$-$C_4$-alkyl, most preferably hydrogen or methyl.

Preferably, at least one of $R^3$ and $R^4$ is hydrogen.

Most preferably, one of $R^3$ and $R^4$ is hydrogen and the other is $C_1$-$C_4$-alkyl, especially methyl, the preferred stereochemistry of the carbon atom to which they are attached is S-, and the S-enantiomer of the compounds of formula (I) is therefore preferred.

Preferably $R^5$ is indazolyl or quinolinyl substituted by at least one halo substituent, preferably at least one fluoro substituent.

Preferably $R^5$ is indazolyl or quinolinyl substituted by one or two fluoro substituents, most preferably two fluoro substituents.

In a particular embodiment of the invention, $R^5$ is 1-methyl-indazol-5-yl substituted by one fluoro substituent at position 6, and optionally a fluoro substituent at position 4, that is 1-methyl-6-fluoro-indazol-5-yl or 1-methyl-4-fluoro-6-fluoro-indazol-5-yl; or $R^5$ is quinolin-6-yl optionally substituted by one fluoro substituent at position 7, and optionally a fluoro substituent at position 5, that is 7-fluoro-quinolin-6-yl or 7-fluoro-5-fluoro-quinolin-6-yl.

In another embodiment of the invention, $R^5$ is represented by a group A or a group B:

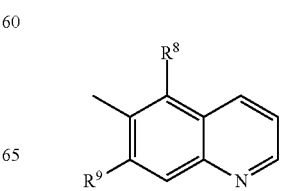

A

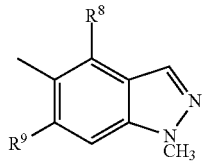

wherein $R^8$ is hydrogen or halogen and $R^9$ is halogen. Preferably, $R^8$ is hydrogen or fluoro and $R^9$ is fluoro.

In a further embodiment of the present invention, there is provided a compound of formula (I),

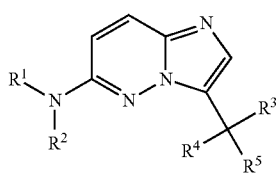

(I)

wherein $R^1$ and $R^2$ together with the nitrogen to which they are attached form a 6 or 7 membered saturated monocyclic group comprising 1 ring N atom to which $R^1$ and $R^2$ are attached, and optionally 1 additional ring N atom, wherein said monocyclic group is unsubstituted or substituted one or more times by a substituent independently selected from $C_1$-$C_7$-alkyl, $C_3$-$C_{12}$-cycloalkyl, halo-$C_1$-$C_7$-alkyl, amino-$C_1$-$C_7$-alkyl, $C_1$-$C_7$-alkylcarbonyl, $C_1$-$C_7$-alkoxycarbonyl, formyl, amino-carbonyl, amino-$C_1$-$C_7$-alkyl-carbonyl, halo-$C_1$-$C_7$-alkylcarbonyl, halo-$C_1$-$C_7$-alkoxycarbonyl, phenyl, pyridyl, oxo;

$R^3$ and $R^4$ are both hydrogen; or
$R^3$ is hydrogen and $R^4$ is methyl;
$R^5$ is 1-methyl-6-fluoro-indazol-5-yl, 1-methyl-4-fluoro-6-fluoro-indazol-5-yl, 7-fluoro-quinolin-6-yl or 7-fluoro-5-fluoro-quinolin-6-yl;
or a pharmaceutically acceptable salt or N-oxide thereof.

In this embodiment, preferably $R^5$ is 7-fluoro-quinolin-6-yl or 7-fluoro-5-fluoro-quinolin-6-yl.

In this embodiment, when $R^3$ is hydrogen and $R^4$ is methyl, the preferred stereochemistry of the carbon atom to which they are attached is S-, and the S-enantiomer of the compounds of formula (I) is therefore preferred.

In a further embodiment of the present invention, a compound of formula (II) is provided:

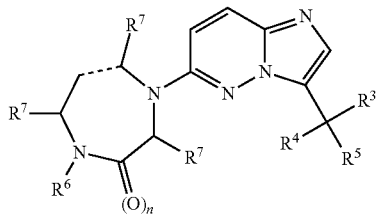

(II)

wherein,
the dashed line is either absent or is a single bond;
n is 0 or 1;
$R^3$ is hydrogen, hydroxy, halogen or $C_1$-$C_7$-alkyl;
$R^4$ is hydrogen, halogen or $C_1$-$C_7$-alkyl;
$R^5$ is indazolyl or quinolinyl substituted by at least one halogen atom;
$R^6$ is hydrogen or a group selected from $C_1$-$C_7$-alkyl, $C_3$-$C_{12}$-cycloalkyl, halo-$C_1$-$C_7$-alkyl, amino-$C_1$-$C_7$-alkyl, $C_1$-$C_7$-alkylcarbonyl, $C_1$-$C_7$-alkoxycarbonyl, formyl, amino-carbonyl, amino-$C_1$-$C_7$-alkyl-carbonyl, halo-$C_1$-$C_7$-alkylcarbonyl, halo-$C_1$-$C_7$-alkoxycarbonyl, phenyl, pyridyl;
each $R^7$ is independently at each occurrence selected from hydrogen, $C_1$-$C_7$-alkyl or substituted $C_1$-$C_7$-alkyl (e.g. halo-$C_1$-$C_7$-alkyl, amino-$C_1$-$C_7$-alkyl, hydroxy-$C_1$-$C_7$-alkyl);
or a pharmaceutically acceptable salt or N-oxide thereof.

In this embodiment, preferably in a compound of formula (II), the dashed line is absent, thus providing a piperazine moiety, i.e.

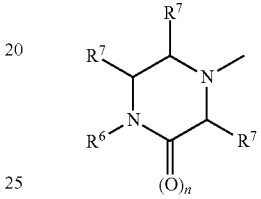

Preferably, in this embodiment, n=1, i.e. the oxo group is present.

Furthermore, in this embodiment, the preferred substituents as defined in other embodiments with respect to formula (I) also apply herein to formula (II), in particular, preferably,
$R^3$ and $R^4$ are both hydrogen; or
$R^3$ is hydrogen and $R^4$ is methyl;
$R^5$ is 1-methyl-6-fluoro-indazol-5-yl, 1-methyl-4-fluoro-6-fluoro-indazol-5-yl, 7-fluoro-quinolin-6-yl or 7-fluoro-5-fluoro-quinolin-6-yl.

A further embodiment of the present invention includes compounds of the following formula (I'):

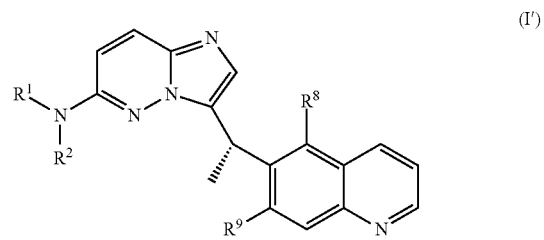

(I')

wherein $R^1$ and $R^2$ together with the nitrogen to which they are attached form a 6 or 7 membered saturated monocyclic group comprising 1 ring N atom to which $R^1$ and $R^2$ are attached, and optionally 1 additional ring N atom, wherein said monocyclic group is unsubstituted or substituted one or more times by a substituent independently selected from $C_1$-$C_7$-alkyl, $C_3$-$C_{12}$-cycloalkyl, halo-$C_1$-$C_7$-alkyl, amino-$C_1$-$C_7$-alkyl, $C_1$-$C_7$-alkylcarbonyl, $C_1$-$C_7$alkoxycarbonyl, formyl, amino-carbonyl, amino-$C_1$-$C_7$-alkyl-carbonyl, halo-$C_1$-$C_7$-alkylcarbonyl, halo-$C_1$-$C_7$-alkoxycarbonyl, phenyl, pyridyl, oxo;
$R^8$ is hydrogen or halogen; and
$R^9$ is halogen;
or a pharmaceutically acceptable salt or N-oxide thereof.

Preferably, in this embodiment $R^8$ is hydrogen or fluoro and $R^9$ is fluoro.

More preferably, in this embodiment $R^8$ is fluoro and $R^9$ is fluoro.

Furthermore, in this embodiment, the groups $R^1$ and $R^2$ together with the nitrogen to which they are attached may also take the values given herein with respect to other embodiments.

Various embodiments of the invention are described herein. It will be recognized that features specified in each embodiment may be combined with other specified features to provide further embodiments.

References herein to a compound of formula (I) also includes reference to compounds of formulae (I') and (II).

In a particular embodiment, the invention provides one or more compounds selected from the Example compounds disclosed herein, or a pharmaceutically acceptable salt or N-oxide thereof.

Any formula given herein is intended to represent compounds having structures depicted by the structural formula as well as certain variations or forms. In particular, compounds of any formula given herein may have asymmetric centers and therefore exist in different enantiomeric forms. If at least one asymmetrical carbon atom is present in a compound of the formula (I), such a compound may exist in optically active form or in the form of a mixture of optical isomers, e.g. in the form of a racemic mixture. All optical isomers and their mixtures, including the racemic mixtures, are part of the present invention. Thus, any given formula given herein is intended to represent a racemate, one or more enantiomeric forms, one or more diastereomeric forms, one or more atropisomeric forms, and mixtures thereof. Furthermore, certain structures may exist as geometric isomers (i.e. cis and trans isomers), as tautomers, or as atropisomers.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers or axes and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Any asymmetric atom (e.g., carbon or the like) of the compound(s) of the present invention can be present in racemic or enantiomerically enriched, for example the (R)-, (S)- or (R,S)-configuration, such as herein when the carbon atom to which $R^2$, $R^3$ and $R^4$ substituents are attached is an asymmetric carbon atom. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Preferably, when the carbon atom to which $R^2$, $R^3$ and $R^4$ substituents are attached is an asymmetric carbon atom, the (S) enantiomer is in excess, in amounts as described above.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (UPLC) using a chiral adsorbent.

Additionally, any formula given herein is intended to represent hydrates, solvates, and polymorphs of such compounds, and mixtures thereof.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$, $^{31}P$, $^{32}P$, $^{35}S$, $^{36}Cl$, $^{125}I$ respectively. Various isotopically labeled compounds of the present invention, for example those into which radioactive isotopes such as $^3H$, $^{13}C$, and $^{14}C$ are incorporated. Such isotopically labelled compounds are useful in metabolic studies (preferably with $^{14}C$), reaction kinetic studies (with, for example $^2H$ or $^3H$), detection or imaging techniques [such as positron emission tomography (PET) or single-photon emission computed tomography (SPECT) including drug or substrate tissue distribution assays, or in radioactive treatment of patients. In particular, an $^{18}F$ or labeled compound may be particularly preferred for PET or SPECT studies. Further, substitution with heavier isotopes such as deuterium (i.e., $^2H$) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a. readily available isotopically labeled reagent for a non-isotopically labeled reagent.

Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this invention any atom specifically designated as a deuterium (D) is meant to represent deuterium, for example in the ranges given above.

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Where the plural form (e.g. compounds, salts) is used, this includes the singular (e.g. a single compound, a single salt). "A compound" does not exclude that (e.g. in a pharmaceutical formulation) more than one compound of the formula (I) (or a salt thereof) is present.

"Salts" (which, what is meant by "or salts thereof" or "or a salt thereof", can be present alone or in mixture with free compound of the formula (I)) are preferably pharmaceutically acceptable salts. Such salts are formed, for example, as acid addition salts, preferably with organic or inorganic acids, from compounds of formula (I) with a basic nitrogen atom, especially the pharmaceutically acceptable salts. Suitable inorganic acids are, for example, halogen acids, such as hydrochloric acid, sulfuric acid, or phosphoric acid. Suitable organic acids are, e.g., carboxylic acids or sulfonic acids, such as fumaric acid or methansulfonic acid. For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred. In view of the close relationship between the novel compounds in free form and those in the form of their salts, including those salts that can be used as intermediates, for example in the purification or identification of the novel compounds, any reference to the free compounds hereinbefore and hereinafter is to be understood as referring also to the corresponding salts, as appropriate and expedient.

As used herein, the term "pharmaceutically acceptable salts" refers to salts that retain the biological effectiveness and properties of the compounds of this invention and, which typically are not biologically or otherwise undesirable. The salt can be present alone or in mixture with free compound of the formula (I). In many cases, the compounds of the present invention are capable of forming acid salts by virtue of the presence of amino groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulformate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

The pharmaceutically acceptable salts of the present invention can be synthesized from a parent compound, a basic or acidic moiety, by conventional chemical methods. Generally, such salts can be prepared by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002). "Salts", or "salts thereof" or "or a salt thereof", can be present alone or in mixture with free compound of the formula (I).

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

The compounds of the invention therefore include compounds of formula I, polymorphs, and isomers thereof (including optical, geometric and tautomeric isomers) and isotopically-labelled compounds of formula I, as defined herein. In preferred embodiments, which are preferred independently, collectively or in any combination or sub-combination, the invention relates to a compound of the formula (I), in free base form or in acid addition salt form, wherein the substituents are as defined herein.

The compounds of the present invention may be administered as prodrugs. Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. [Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association).]

Prodrugs can, for example, be produced by replacing appropriate functionalities present in the compounds of formula (I) with certain moieties known to those skilled in the art as 'promoieties' as described, for example, in "Design of Prodrugs" by H Bundgaard (Elsevier, 1985).

Some examples of such prodrugs include:
(i) where the compound of formula (I) contains a carboxylic acid functionality (—COOH), an ester thereof, for example, replacement of the hydrogen with $(C_1-C_8)$alkyl;
(ii) where the compound of formula (I) contains an alcohol functionality (—OH), an ether thereof, for example, replacement of the hydrogen with $(C_1-C_6)$alkanoyloxymethyl; and
(iii) where the compound of formula (I) contains a primary or secondary amino functionality (—$NH_2$ or —NHR where R≠H), an amide thereof, for example, replacement of one or both hydrogens with $(C_1-C_{10})$alkanoyl.

Certain compounds of formula (I) may also themselves act as prodrugs of other compounds of formula (I).

The invention further relates to a pharmaceutically acceptable prodrug of a compound of formula (I). The invention further relates to a pharmaceutically acceptable metabolite (especially of a pharmaceutically active metabolite) of a compound of formula (I).

"C-Met tyrosine kinase mediated diseases" are especially such disorders that respond in a beneficial way (e.g. amelioration of one or more symptoms, delay of the onset of a disease, up to temporary or complete cure from a disease) to the inhibition of a protein tyrosine kinase, especially inhibition of a c-Met kinase. These disorders include proliferative diseases such as tumor diseases, in particular solid tumors and metastasis derived thereof, e.g. hereditary papillary renal cell carcinoma (PRCC), sporadic forms of PRCC, head and neck cancer, squamous cell carcinoma, gastric carcinoma, pancreatic carcinoma, lung cancer, bladder cancer, breast cancer, leiomyosarcoma, glioblastoma, melanoma, alveolar soft part sarcoma. These disorders further include inflammatory conditions, such as inflammatory conditions due to an infection.

"Treatment" includes prophylactic (preventive) and therapeutic treatment as well as the delay of progression of a disease, disorder or condition.

"Combination" refers to either a fixed combination in one dosage unit form, or a kit of parts for the combined administration where a compound of the formula (I) and a combination partner (e.g. an other drug as explained below, also referred to as "therapeutic agent" or "co-agent") may be administered independently at the same time or separately within time intervals, especially where these time intervals allow that the combination partners show a cooperative, e.g. synergistic effect. The terms "co-administration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g. a compound of formula (I) and a combination partner, are both administered to a patient simultaneously in the form of a single entity or dosage. The term "non-fixed combination" means that the active ingredients, e.g. a compound of formula (I) and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more active ingredients.

In preferred embodiments, which are preferred independently, collectively or in any combination or sub-combination, the invention relates to a compound of the formula (I), in free base form or in acid addition salt form, wherein the substituents are as defined herein.

The invention further relates to pharmaceutically acceptable prodrugs of a compound of formula (I). The invention further relates to pharmaceutically acceptable metabolites of a compound of formula (I).

The invention relates especially to the compounds of the formula (I) as provided in the Examples, as well as the methods of manufacture described therein.

The compounds of formula (I) have valuable pharmacological properties, as described hereinbefore and hereinafter.

In another embodiment of the invention, there is provided a method for treating a c-Met related disorder or condition. The disorder or condition to be treated is preferably a proliferative disease such as a cancer or an inflammatory condition. Compounds of formula (I) are further useful for treating diseases associated with a c-Met-related condition.

A: Proliferative diseases: Compounds of formula (I) are particular useful for the treatment of one or more of the following proliferative diseases:

Compounds of formula (I) are useful in the treatment of cancer wherein the cancer is selected from the group consisting of brain cancer, stomach cancer, genital cancer, urinary cancer, prostate cancer, bladder cancer (superficial and muscle invasive), breast cancer, cervical cancer, colon cancer, colorectal cancer, glioma (including glioblastoma, anaplastic astrocytoma, oligoastrocytoma, oligodendroglioma), esophageal cancer, gastric cancer, gastrointestinal cancer, liver cancer, hepatocellular carcinoma (HCC) including childhood HCC, head and neck cancer (including head and neck squamous-cell carcinoma, nasopharyngeal carcinoma), Hurthle cell carcinoma, epithelial cancer, skin cancer, melanoma (including malignant melanoma), mesothelioma, lymphoma, myeloma (including multiple myeloma), leukemias, lung cancer (including non-small cell lung cancer (including all histological subtypes: adenocarcinoma, squamous cell carcinoma, bronchoalveolar carcinoma, large-cell carcinoma, and adenosquamous mixed type), small-cell lung cancer), ovarian cancer, pancreatic cancer, prostate cancer, kidney cancer (including but not limited to papillary renal cell carcinoma), intestine cancer, renal cell cancer (including hereditary and sporadic papillary renal cell cancer, Type I and Type II, and clear cell renal cell cancer); sarcomas, in particular osteosarcomas, clear cell sarcomas, and soft tissue sarcomas (including alveolar and embryonal rhabdomyosarcomas, alveolar soft part sarcomas); thyroid carcinoma (papillary and other subtypes).

Compounds of formula (I) are useful in the treatment of cancer wherein the cancer is stomach, colon, liver, genital, urinary, melanoma, or prostate. In a particular embodiment, the cancer is liver or esophageal.

Compounds of formula (I) are useful in the treatment of colon cancer, including metastases, e.g. in the liver, and of non-small-cell lung carcinoma.

Compounds of formula (I) may also be used in the treatment of hereditary papillary renal carcinoma (Schmidt, L. et al. Nat. Genet. 16, 68-73, 1997) and other proliferative diseases in which c-MET is overexpressed or constitutively activated by mutations (Jeffers and Vande Woude. Oncogene 18, 5120-5125, 1999; and reference cited therein) or chromosomal rearrange-ments (e.g. TPR-MET; Cooper et al. Nature 311, 29-33, 1984; Park. et al. Cell 45, 895-904, 1986).

Compounds of formula (I) are further useful in the treatment of additional cancers and conditions as provided herein or known in the art.

B: Inflammatory conditions: Compounds of formula (I) are particular suitable for the treatment of one or more inflammatory conditions.

In a further embodiment, the inflammatory condition is due to an infection. In one embodiment, the method of treatment would be to block pathogen infection. In a particular embodiment, the infection is a bacterial infection, e.g., a *Listeria* infection. See, e.g., Shen et al. Cell 103: 501-10, (2000) whereby a bacterial surface protein activates c-Met kinase through binding to the extracellular domain of the receptor, thereby mimicking the effect of the cognate ligand HGF/SF.

Compounds of formula (I) are further useful in the treatment of additional inflammatory disorders and conditions as provided herein or known in the art.

C: Combination therapy: In certain embodiments, any of the above methods involve further administering a chemotherapeutic agent.

In a related embodiment, the chemotherapeutic agent is an anti-cancer agent. Specific combinations are provided throughout the application.

In a further related embodiment, any of the above methods involve further administering a pathway specific inhibitor. The pathway specific inhibitor may be a chemotherapeutic agent or may be a biologic agent, e.g., such as antibodies. Pathway specific inhibitors include, but are not limited to, inhibitors of EGFR, Her-2, Her-3, VEGFR, Ron, IGF-IR, PI-3K, mTOR, Raf. In a further related embodiment to several of the above methods, following administering to the subject or contacting the cell, these methods can further involve observing amelioration or retardation of development or metastasis of the cancer.

Thus, in one embodiment, the invention relates to a method of treating a c-Met related disorder of condition which involves administering to a subject in need thereof an effective amount of any of a compound of formula (I).

In a further embodiment, the invention relates to a compound of formula (I) or a pharmaceutically acceptable salt, as a medicament/for use as a medicament, in particular for the treatment of one or more C-Met tyrosine kinase mediated diseases.

In a further embodiment, the invention relates to the use of a compound of formula (I) or a pharmaceutically acceptable salt, as active ingredient in a medicament, in particular for the treatment of one or more C-Met tyrosine kinase mediated diseases.

In a further embodiment, the invention relates to the use of a compound of formula (I) or a pharmaceutically acceptable salt, as medicament, in particular for the treatment of one or more C-Met tyrosine kinase mediated diseases.

In a further embodiment, the invention relates to the use of a compound of formula (I) or a pharmaceutically acceptable salt, for the manufacture of a medicament for the treatment of one or more C-Met tyrosine kinase mediated diseases.

In a further embodiment, the invention relates to a compound of formula (I) or a pharmaceutically acceptable salt of such a compound, for use in a method for the treatment of a subject in need thereof, especially for the treatment of a C-Met tyrosine kinase mediated disease, most especially in a patient requiring such treatment.

In a further embodiment, the invention relates to a method for the treatment of a disease or disorder which responds to an inhibition of C-Met tyrosine kinase, which comprises administering a compound of formula (I) or a pharmaceutically acceptable salt thereof, wherein the radicals and symbols have the meanings as defined above, especially in a quantity effective against said disease, to a warm-blooded animal requiring such treatment.

In a further embodiment, the invention relates to a pharmaceutical composition comprising a compound of formula (I) as active ingredient in association with at least one pharmaceutical carrier or diluent. Such compositions may be manufactured in conventional manner.

In a further embodiment, the invention relates to a method of treatment of one or more C-Met tyrosine kinase mediated diseases, in a subject in need of such treatment, which comprises administering to such subject a therapeutically effective amount of compound of formula (I).

In a further embodiment, the invention relates to pharmaceutical compositions comprising: (a) an effective amount of compound of formula (I) and pharmaceutically acceptable salts, pharmaceutically acceptable prodrugs, and pharmaceutically active metabolites thereof; and (b) one or more pharmaceutically acceptable excipients and/or diluents.

In a further embodiment, the invention relates to a pharmaceutical composition for treatment of a disease, e.g. of solid or liquid tumours in warm-blooded animals, including humans, comprising a dose effective in the treatment of said disease of a compound of the formula (I) as described above or a pharmaceutically acceptable salt of such a compound together with a pharmaceutically acceptable carrier (=carrier material).

The invention also provides a pharmaceutical preparation (composition), comprising a compound of formula (I) as defined herein, or a pharmaceutically acceptable salt of such a compound, or a hydrate or solvate thereof, and at least one pharmaceutically acceptable carrier and/or diluents and optionally one or more further therapeutic agents.

The compounds of the invention may be administered by any conventional route, in particular parenterally, for example in the form of injectable solutions or suspensions, enterally, e.g. orally, for example in the form of tablets or capsules, topically, e.g. in the form of lotions, gels, ointments or creams, or in a nasal or a suppository form. Topical administration is e.g. to the skin. A further form of topical administration is to the eye. Pharmaceutical compositions comprising a compound of the invention in association with at least one pharmaceutical acceptable carrier or diluent may be manufactured in conventional manner by mixing with a pharmaceutically acceptable carrier or diluent.

The invention relates also to pharmaceutical compositions comprising an effective amount, especially an amount effective in the treatment of one of the above-mentioned diseases (=disorders), of a compound of formula (I) or a pharmaceutically acceptable salt thereof together with one or more pharmaceutically acceptable carriers that are suitable for topical, enteral, for example oral or rectal, or parenteral administration and that may be inorganic or organic, solid or liquid. There can be used for oral administration especially tablets or gelatin capsules that comprise the active ingredient together with diluents, for example lactose, dextrose, mannitol, and/or glycerol, and/or lubricants and/or polyethylene glycol. Tablets may also comprise binders, for example magnesium aluminum silicate, starches, such as corn, wheat or rice starch, gelatin, methylcellulose, sodium carboxymethylcellulose and/or polyvinylpyrrolidone, and, if desired, disintegrators, for example starches, agar, alginic acid or a salt thereof, such as sodium alginate, and/or effervescent mixtures, or adsorbents, dyes, flavorings and sweeteners. It is also possible to use the pharmacologically active compounds of the present invention in the form of parenterally administrable compositions or in the form of infusion solutions. The pharmaceutical compositions may be sterilized and/or may comprise excipients, for example preservatives, stabilisers, wetting compounds and/or emulsifiers, solubilisers, salts for regulating the osmotic pressure and/or buffers. The present pharmaceutical compositions, which may, if desired, comprise other pharmacologically active substances are prepared in a manner known per se, for example by means of conventional mixing, granulating, confectionning, dissolving or lyophilising processes, and comprise approximately from 1% to 99%, especially from approximately 1% to approximately 20%, active ingredient(s).

The dosage of the active ingredient to be applied to a warm-blooded animal depends upon a variety of factors including type, species, age, weight, sex and medical condition of the patient; the severity of the condition to be treated; the route of administration; the renal and hepatic function of the patient; and the particular compound employed. A physician, clinician or veterinarian of ordinary skill can readily determine and prescribe the effective amount of the drug required to prevent, counter or arrest the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug. The dose of a compound of the formula (I) or a pharmaceutically acceptable salt thereof to be administered to warm-blooded animals, for example humans of approximately 70 kg body weight, is preferably from approximately 3 mg to approximately 5 g, more preferably from approximately 10 mg to approximately 1.5 g per person per day, divided preferably into 1 to 3 single doses which may, for example, be of the same size. Usually, children receive half of the adult dose.

The invention relates also to a combination of a compound of formula (I) with one or more other therapeutically active agents. Thus, a compound of formula (I) can be administered alone or in combination with one or more other therapeutic agents, possible combination therapy taking the form of fixed combinations or the administration of a compound of the invention and one or more other therapeutic agents being staggered or given independently of one another, or the combined administration of fixed combinations and one or more other therapeutic agents.

A compound of formula (I) can besides or in addition be administered especially for tumor therapy in combination with chemotherapy, radiotherapy, immunotherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Thus, a compound of the formula (I) may be used in combination with other antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity; anti-angiogenic compounds; compounds which target, decrease or inhibit the activity of a protein or lipid phosphatase; gonadorelin agonists; antiandrogens; methionine aminopeptidase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors; kinesin spindle protein inhibitors; MEK inhibitors; leucovorin; EDG binders; antileukemia compounds; ribonucleotide reductase inhibitors; S-adenosylmethionine decarboxylase inhibitors; angiostatic steroids; corticosteroids; other chemotherapeutic compounds (as defined below); photosensitizing compounds.

Further, alternatively or in addition they may be used in combination with other tumor treatment approaches, including surgery, ionizing radiation, photodynamic therapy, implants, e.g. with corticosteroids, hormones, or they may be used as radiosensitizers.

The term "aromatase inhibitor" as used herein relates to a compound which inhibits the estrogen production, i.e. the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketoconazole, vorozole, fadrozole, anastrozole and letrozole. Exemestane can be administered, e.g., in the form as it is marketed, e.g. under the trademark AROMASIN. Formestane can be administered, e.g., in the form as it is marketed, e.g. under the trademark LENTARON. Fadrozole can be administered, e.g., in the form as it is marketed, e.g. under the trademark AFEMA. Anastrozole can be administered, e.g., in the form as it is marketed, e.g. under the trademark ARIMIDEX. Letrozole can be administered, e.g., in the form as it is marketed, e.g. under the trademark FEMARA or FEMAR. Aminoglutethimide can be administered, e.g., in the form as it is marketed, e.g. under the trademark ORIMETEN. A combination of the invention comprising a chemotherapeutic agent which is an aromatase inhibitor is particularly useful for the treatment of hormone receptor positive tumors, e.g. breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen can be administered, e.g., in the form as it is marketed, e.g. under the trademark NOLVADEX. Raloxifene hydrochloride can be administered, e.g., in the form as it is marketed, e.g. under the trademark EVISTA. Fulvestrant can be formulated as disclosed in U.S. Pat. No. 4,659,516 or it can be administered, e.g., in the form as it is marketed, e.g. under the trademark FASLODEX. A combination of the invention comprising a chemotherapeutic agent which is an antiestrogen is particularly useful for the treatment of estrogen receptor positive tumors, e.g. breast tumors.

The term "anti-androgen" as used herein relates to any substance which is capable of inhibiting the biological effects of androgenic hormones and includes, but is not limited to, bicalutamide (CASODEX), which can be formulated, e.g. as disclosed in U.S. Pat. No. 4,636,505. The term "gonadorelin agonist" as used herein includes, but is not limited to abarelix, goserelin and goserelin acetate. Goserelin is disclosed in U.S. Pat. No. 4,100,274 and can be administered, e.g., in the form as it is marketed, e.g. under the trademark ZOLADEX. Abarelix can be formulated, e.g. as disclosed in U.S. Pat. No. 5,843,901.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148 (compound A1 in WO99/17804). Irinotecan can be administered, e.g. in the form as it is marketed, e.g. under the trademark CAMPTOSAR. Topotecan can be administered, e.g., in the form as it is marketed, e.g. under the trademark HYCAMTIN.

The term "topoisomerase II inhibitor" as used herein includes, but is not limited to the anthracyclines such as doxorubicin (including liposomal formulation, e.g. CAELYX), daunorubicin, epirubicin, idarubicin and nemorubicin, the anthraquinones mitoxantrone and losoxantrone, and the podophillotoxines etoposide and teniposide. Etoposide can be administered, e.g. in the form as it is marketed, e.g. under the trademark ETOPOPHOS. Teniposide can be administered, e.g. in the form as it is marketed, e.g. under the trademark VM 26-BRISTOL. Doxorubicin can be administered, e.g. in the form as it is marketed, e.g. under the trademark ADRIBLASTIN or ADRIAMYCIN. Epirubicin can be administered, e.g. in the form as it is marketed, e.g. under the trademark FARMORUBICIN. Idarubicin can be administered, e.g. in the form as it is marketed, e.g. under the trademark ZAVEDOS. Mitoxantrone can be administered, e.g. in the form as it is marketed, e.g. under the trademark NOVANTRON.

The term "microtubule active compound" relates to microtubule stabilizing, microtubule destabilizing compounds and microtublin polymerization inhibitors including, but not limited to taxanes, e.g. paclitaxel and docetaxel, vinca alkaloids, e.g., vinblastine, especially vinblastine sulfate, vincristine especially vincristine sulfate, and vinorelbine, discodermolides, cochicine and epothilones and derivatives thereof, e.g. epothilone B or D or derivatives thereof. Paclitaxel may be administered e.g. in the form as it is marketed, e.g. TAXOL. Docetaxel can be administered, e.g., in the form as it is marketed, e.g. under the trademark TAXOTERE. Vinblastine sulfate can be administered, e.g., in the form as it is marketed, e.g. under the trademark VINBLASTIN R.P. Vincristine sulfate can be administered, e.g., in the form as it is marketed, e.g. under the trademark FARMISTIN. Discodermolide can be obtained, e.g., as disclosed in U.S. Pat. No. 5,010,099. Also included are Epothilone derivatives which are disclosed in WO 98/10121, U.S. Pat. No. 6,194,181, WO 98/25929, WO 98/08849, WO 99/43653, WO 98/22461 and WO 00/31247. Especially preferred are Epothilone A and/or B.

The term "alkylating compound" as used herein includes, but is not limited to, cyclophosphamide, ifosfamide, melphalan or nitrosourea (BCNU or Gliadel). Cyclophosphamide can be administered, e.g., in the form as it is marketed, e.g. under the trademark CYCLOSTIN. Ifosfamide can be administered, e.g., in the form as it is marketed, e.g. under the trademark HOLOXAN.

The term "histone deacetylase inhibitors" or "HDAC inhibitors" relates to compounds which inhibit the histone deacetylase and which possess antiproliferative activity. This includes compounds disclosed in WO 02/22577, especially N-hydroxy-3-[4-[[(2-hydroxyethyl)[2-(1H-indol-3-yl) ethyl]-amino]methyl]phenyl]-2E-2-propenamide, N-hydroxy-3-[4-[[[2-(2-methyl-1H-indol-3-yl)-ethyl]-amino] methyl]phenyl]-2E-2-propenamide and pharmaceutically acceptable salts thereof. It further especially includes Suberoylanilide hydroxamic acid (SAHA). Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065, in particular, N-hydroxy-3-[4-[[[2-(2-methyl-1H-indol-3-yl)-ethyl]-amino]methyl]phenyl]-2E-2-propenamide, or a pharmaceutically acceptable salt thereof and N-hydroxy-3-[4-[(2-hydroxyethyl){2-(1H-indol-3-yl) ethyl]amino]methyl]phenyl]-2E-2-propenamide, or a pharmaceutically acceptable salt thereof, especially the lactate salt.

The term "antineoplastic antimetabolite" includes, but is not limited to, 5-Fluorouracil or 5-FU, capecitabine, gemcitabine, DNA demethylating compounds, such as 5-azacytidine and decitabine, methotrexate and edatrexate, and folic acid antagonists such as pemetrexed. Capecitabine can be administered, e.g., in the form as it is marketed, e.g. under the trademark XELODA. Gemcitabine can be administered, e.g., in the form as it is marketed, e.g. under the trademark GEMZAR.

The term "platin compound" as used herein includes, but is not limited to, carboplatin, cis-platin, cisplatinum and oxaliplatin. Carboplatin can be administered, e.g., in the form as it is marketed, e.g. under the trademark CARBOPLAT. Oxaliplatin can be administered, e.g., in the form as it is marketed, e.g. under the trademark ELOXATIN.

The term "compounds targeting/decreasing a protein or lipid kinase activity"; or a "protein or lipid phosphatase activity"; or "further anti-angiogenic compounds" as used herein includes, but is not limited to, c-Met tyrosine kinase and/or serine and/or threonine kinase inhibitors or lipid kinase inhibitors, e.g., a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, e.g. a N-phenyl-2-pyrimidine-amine derivative, e.g. imatinib, SU101, SU6668 and GFB-111;

b) compounds targeting, decreasing or inhibiting the activity of the fibroblast growth factor-receptors (FGFR);

c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, such as those compounds disclosed in WO 02/092599, or antibodies that target the extracellular domain of IGF-I receptor or its growth factors;

d) compounds targeting, decreasing or inhibiting the activity of the Trk receptor tyrosine kinase family, or ephrin kinase family inhibitors;

e) compounds targeting, decreasing or inhibiting the activity of the Axl receptor tyrosine kinase family;

f) compounds targeting, decreasing or inhibiting the activity of the Ret receptor tyrosine kinase;
g) compounds targeting, decreasing or inhibiting the activity of the Kit/SCFR receptor tyrosine kinase, e.g. imatinib;
h) compounds targeting, decreasing or inhibiting the activity of the C-kit receptor tyrosine kinases—(part of the PDGFR family), such as compounds which target, decrease or inhibit the activity of the c-Kit receptor tyrosine kinase family, especially compounds which inhibit the c-Kit receptor, e.g. imatinib;
i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, e.g. a N-phenyl-2-pyrimidine-amine derivative, e.g. imatinib or nilotinib (AMN107); PD180970; AG957; NSC 680410; PD173955 from ParkeDavis; or dasatinib (BMS-354825)
j) compounds targeting, decreasing or inhibiting the activity of members of the protein kinase C(PKC) and Raf family of serine/threonine kinases, members of the MEK, SRC, JAK, FAK, PDK1, PKB/Akt, and Ras/MAPK family members, and/or members of the cyclin-dependent kinase family (CDK) and are especially those staurosporine derivatives disclosed in U.S. Pat. No. 5,093,330, e.g. midostaurin; examples of further compounds include e.g. UCN-01, safingol, BAY 43-9006, Bryostatin 1, Perifosine; Ilmofosine; RO 318220 and RO 320432; GO 6976; Isis 3521; LY333531/LY379196; isochinoline compounds such as those disclosed in WO 00/09495; FTIs; PD184352 or QAN697 (a P13K inhibitor) or AT7519 (CDK inhibitor);
k) compounds targeting, decreasing or inhibiting the activity of protein-tyrosine kinase inhibitors, such as compounds which target, decrease or inhibit the activity of protein-tyrosine kinase inhibitors include imatinib mesylate (GLEEVEC) or tyrphostin. A tyrphostin is preferably a low molecular weight (Mr<1500) compound, or a pharmaceutically acceptable salt thereof, especially a compound selected from the benzylidenemalonitrile class or the S-arylbenzenemalonirile or bisubstrate quinoline class of compounds, more especially any compound selected from the group consisting of Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin);
l) compounds targeting, decreasing or inhibiting the activity of the epidermal growth factor family of receptor tyrosine kinases (EGFR, ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, e.g. EGF receptor, ErbB2, ErbB3 and ErbB4 or bind to EGF or EGF related ligands, and are in particular those compounds, proteins or monoclonal antibodies generically and specifically disclosed in WO 97/02266, e.g. the compound of ex. 39, or in EP 0 564 409, WO 99/03854, EP 0520722, EP 0 566 226, EP 0 787 722, EP 0 837 063, U.S. Pat. No. 5,747,498, WO 98/10767, WO 97/30034, WO 97/49688, WO 97/38983 and, especially, WO 96/30347 (e.g. compound known as CP 358774), WO 96/33980 (e.g. compound ZD 1839) and WO 95/03283 (e.g. compound ZM105180); e.g. trastuzumab (Herceptin™), cetuximab (Erbitux™), Iressa, Tarceva, OSI-774, CI-1033, EKB-569, GW-2016, E1.1, E2.4, E2.5, E6.2, E6.4, E2.11, E6.3 or E7.6.3, and 7Hpyrrolo-[2,3-d]pyrimidine derivatives which are disclosed in WO 03/013541; and
m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF;
n) compounds targeting, decreasing or inhibiting the activity of the Ron receptor tyrosine kinase.

Further anti-angiogenic compounds include compounds having another mechanism for their activity, e.g. unrelated to protein or lipid kinase inhibition e.g. thalidomide (THALOMID) and TN P-470.

The term "Compounds which target, decrease or inhibit the activity of a protein or lipid phosphatase" includes, but is not limited to inhibitors of phosphatase 1, phosphatase 2A, or CDC25, e.g. okadaic acid or a derivative thereof.

The term "Compounds which induce cell differentiation processes" includes, but is not limited to e.g. retinoic acid, α-γ- or δ-tocopherol or α- γ- or δ-tocotrienol.

The term "cyclooxygenase inhibitor" as used herein includes, but is not limited to, e.g. Cox-2 inhibitors, 5-alkyl substituted 2-arylaminophenylacetic acid and derivatives, such as celecoxib (CELEBREX), rofecoxib (VIOXX), etoricoxib, valdecoxib or a 5-alkyl-2-arylaminophenylacetic acid, e.g. 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. "Etridonic acid" can be administered, e.g., in the form as it is marketed, e.g. under the trademark DIDRONEL. "Clodronic acid" can be administered, e.g., in the form as it is marketed, e.g. under the trademark BONEFOS. "Tiludronic acid" can be administered, e.g., in the form as it is marketed, e.g. under the trademark SKELID. "Pamidronic acid" can be administered, e.g. in the form as it is marketed, e.g. under the trademark AREDIA™. "Alendronic acid" can be administered, e.g., in the form as it is marketed, e.g. under the trademark FOSAMAX. "Ibandronic acid" can be administered, e.g., in the form as it is marketed, e.g. under the trademark BONDRANAT. "Risedronic acid" can be administered, e.g., in the form as it is marketed, e.g. under the trademark ACTONEL. "Zoledronic acid" can be administered, e.g. in the form as it is marketed, e.g. under the trademark ZOMETA. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons, e.g. interferon γ.

The term "inhibitor of Ras oncogenic isoforms", e.g. H-Ras, K-Ras, or N-Ras, as used herein refers to compounds which target, decrease or inhibit the oncogenic activity of Ras e.g. a "farnesyl transferase inhibitor" e.g. L-744832, DK8G557 or R115777 (Zarnestra). The term "telomerase inhibitor" as used herein refers to compounds which target, decrease or inhibit the activity of telomerase. Compounds which target, decrease or inhibit the activity of telomerase are especially compounds which inhibit the telomerase receptor, e.g. telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase are e.g. bengamide or a derivative thereof.

The term "proteasome inhibitor" as used herein refers to compounds which target, decrease or inhibit the activity of the proteasome. Compounds which target, decrease or inhibit the activity of the proteasome include e.g. Bortezomid (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors e.g. compounds targeting, decreasing or inhibiting the activity of FMS-like tyrosine kinase receptors (Flt-3R); interferon, 1-b-D-arabinofuransylcytosine (ara-c) and bisulfan; and ALK inhibitors e.g. compounds which target, decrease or inhibit anaplastic lymphoma kinase.

The term "Compounds which target, decrease or inhibit the activity of FMS-like tyrosine kinase receptors (Flt-3R)" are especially compounds, proteins or antibodies which inhibit members of the Flt-3R receptor kinase family, e.g. PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90 e.g., 17-allylamino,17-demethoxygeldanamycin (17AAG, 17-DMAG), a geldanamycin derivative; other geldanamycin related compounds; radicicol and HDAC inhibitors; IPI-504, CNF1010, CNF2024, CNF1010 from Conforma Therapeutics; temozolomide (TEMODAL®), AUY922 from Novartis.

The term "antiproliferative antibodies" as used herein includes, but is not limited to, trastuzumab (Herceptin™), Trastuzumab-DM1, erbitux, bevacizumab (Avastin™), rituximab (Rituxan®), PRO64553 (anti-CD40) and 2C4 Antibody. By antibodies is meant e.g. intact monoclonal antibodies, polyclonal antibodies, multispecific antibodies formed from at least 2 intact antibodies, and antibodies fragments so long as they exhibit the desired biological activity.

The term "antileukemic compounds" includes, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. For the treatment of acute myeloid leukemia (AML), compounds of formula (I) can be used in combination with standard leukemia therapies, especially in combination with therapies used for the treatment of AML. In particular, compounds of formula (I) can be administered in combination with, e.g., farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

"Somatostatin receptor antagonists" as used herein refers to compounds which target, treat or inhibit the somatostatin receptor such as octreotide, and SOM230.

"Tumor cell damaging approaches" refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in *Principles and Practice of Oncology*, Devita et al., Eds., 4$^{th}$ Edition, Vol. 1, pp. 248-275 (1993).

The term "EDG binders" as used herein refers a class of immunosuppressants that modulates lymphocyte recirculation, such as FTY720.

The term "kinesin spindle protein inhibitors" is known in the field and includes SB715992 or SB743921 from GlaxoSmithKline, pentamidine/chlorpromazine from CombinatoRx;

The term "MEK inhibitors" is known in the field and includes ARRY142886 from Array PioPharma, AZD6244 from AstraZeneca, PD181461 from Pfizer, leucovorin.

The term "ribonucleotide reductase inhibitors" includes, but is not limited to to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives, such as PL-1, PL-2, PL-3, PL-4, PL-5, PL-6, PL-7 or PL-8 mentioned in Nandy et al., *Acta Oncologica*, Vol. 33, No. 8, pp. 953-961 (1994).

The term "S-adenosylmethionine decarboxylase inhibitors" as used herein includes, but is not limited to the compounds disclosed in U.S. Pat. No. 5,461,076.

Also included are in particular those compounds, proteins or monoclonal antibodies of VEGF/VEGFR disclosed in WO 98/35958, e.g. 1-(4-chloroanilino)-4-(4-pyridylmethyl)phthalazine or a pharmaceutically acceptable salt thereof, e.g. the succinate, or in WO 00/09495, WO 00/27820, WO 00/59509, WO 98/11223, WO 00/27819 and EP 0 769 947; those as described by Prewett et al, *Cancer Res*, Vol. 59, pp. 5209-5218 (1999); Yuan et al., *Proc Natl Acad Sci USA*, Vol. 93, pp. 14765-14770 (1996); Zhu et al., *Cancer Res*, Vol. 58, pp. 3209-3214 (1998); and Mordenti et al., *Toxicol Pathol*, Vol. 27, No. 1, pp. 14-21 (1999); in WO 00/37502 and WO 94/10202; ANGIOSTATIN, described by O'Reilly et al., *Cell*, Vol. 79, pp. 315-328 (1994); ENDOSTATIN, described by O'Reilly et al., *Cell*, Vol. 88, pp. 277-285 (1997); anthranilic acid amides; ZD4190; ZD6474; SU5416; SU6668; bevacizumab; or anti-VEGF antibodies or anti-VEGF receptor antibodies, e.g. rhuMAb and RHUFab, VEGF aptamer e.g. Macugon; FLT-4 inhibitors, FLT-3 inhibitors, VEGFR-2 IgG1 antibody, Angiozyme (RPI 4610) and Bevacizumab (Avastin™).

"Photodynamic therapy" as used herein refers to therapy which uses certain chemicals known as photosensitizing compounds to treat or prevent cancers. Examples of photodynamic therapy includes treatment with compounds, such as e.g. VISUDYNE and porfimer sodium.

"Angiostatic steroids" as used herein refers to compounds which block or inhibit angiogenesis, such as, e.g., anecortave, triamcinolone. hydrocortisone, 11-α-epihydrocotisol, cortexolone, 17α-hydroxyprogesterone, corticosterone, desoxycorticosterone, testosterone, estrone and dexamethasone.

"Corticosteroids" as used herein includes, but is not limited to compounds, such as e.g. fluocinolone, dexamethasone; in particular in the form of implants.

"Other chemotherapeutic compounds" include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

A compound of formula (I) may also be used in combination with one or more further drug substances selected from the group of anti-inflammatory drug substances; antihistamine drug substances; bronchodilatatory drug substances, NSAID; antagonists of chemokine receptors.

The compounds of the invention are also useful as co-therapeutic compounds for use in combination with such further drug substances, particularly in the treatment of inflammatory diseases such as those mentioned hereinbefore, for example as potentiators of therapeutic activity of such drugs or as a means of reducing required dosaging or potential side effects of such drugs. A compound of the invention may be mixed with such other drug substance in a fixed pharmaceutical composition or it may be administered separately (i.e. before, simultaneously with or after the other drug substance). Accordingly, the invention includes a combination of a compound of formula (I) with one or more further drug substance selected from the group of anti-inflammatory drug substances; antihistamine drug substances; bronchodilatatory drug substances, NSAID antagonists of chemokine receptors; said compound of the formula (I) and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate, or steroids described in WO 02/88167, WO 02/12266, WO 02/100879, WO 02/00679 (especially those of Examples 3, 11, 14, 17, 19, 26, 34, 37, 39, 51, 60, 67, 72, 73, 90, 99 and 101), WO 03/035668, WO 03/048181, WO 03/062259, WO 03/064445, WO 03/072592, non-steroidal glucocorticoid receptor agonists such as those described in WO 00/00531, WO 02/10143, WO 03/082280, WO 03/082787, WO 03/104195, WO 04/005229; LTB4 antagonists such LY293111, CGS025019C, CP-195543, SC-53228, BIIL 284, ONO 4057, SB 209247 and those described in U.S. Pat. No. 5,451,700; LTD4 antagonists such as montelukast and zafirlukast; PDE4 inhibitors such cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo), and those disclosed in WO 92/19594, WO 93/19749, WO 93/19750, WO 93/19751, WO 98/18796, WO 99/16766, WO 01/13953, WO 03/104204, WO 03/104205, WO 03/39544, WO 04/000814, WO 04/000839, WO 04/005258, WO 04/018450, WO 04/018451, WO 04/018457, WO 04/018465, WO 04/018431, WO 04/018449, WO 04/018450, WO 04/018451, WO 04/018457, WO 04/018465, WO 04/019944, WO 04/019945, WO 04/045607 and WO 04/037805; A2a agonists such as those disclosed in EP 409595A2, EP 1052264, EP 1241176, WO 94/17090, WO 96/02543, WO 96/02553, WO 98/28319, WO 99/24449, WO 99/24450, WO 99/24451, WO 99/38877, WO 99/41267, WO 99/67263, WO 99/67264, WO 99/67265, WO 99/67266, WO 00/23457, WO 00/77018, WO 00/78774, WO 01/23399, WO 01/27130, WO 01/27131, WO 01/60835, WO 01/94368, WO 02/00676, WO 02/22630, WO 02/96462, WO 03/086408, WO 04/039762, WO 04/039766, WO 04/045618 and WO 04/046083; A2b antagonists such as those described in WO 02/42298; and beta-2 adrenoceptor agonists such as albuterol (salbutamol), metaproterenol, terbutaline, salmeterol fenoterol, procaterol, and especially, formoterol and pharmaceutically acceptable salts thereof, and compounds (in free or salt or solvate form) of formula I of WO 0075114, which document is incorporated herein by reference, preferably compounds of the Examples thereof, especially a compound of formula

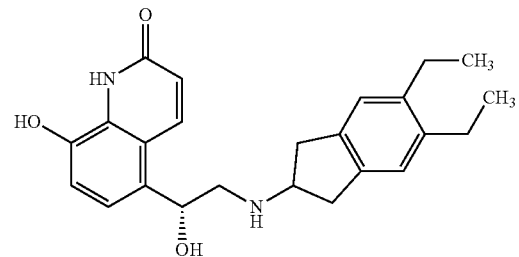 [SMILES: CCc1cc2c(cc1CC)CC(NC[C@H](O)c1ccc(O)c3[nH]c(=O)ccc13)C2]

and pharmaceutically acceptable salts thereof, as well as compounds (in free or salt or solvate form) of formula I of WO 04/16601, and also compounds of WO 04/033412. Suitable bronchodilatory drugs include anticholinergic or antimuscarinic compounds, in particular ipratropium bromide, oxitropium bromide, tiotropium salts and CHF 4226 (Chiesi), and glycopyrrolate, but also those described in WO 01/04118, WO 02/51841, WO 02/53564, WO 03/00840, WO 03/87094, WO 04/05285, WO 02/00652, WO 03/53966, EP 424021, U.S. Pat. No. 5,171,744, U.S. Pat. No. 3,714,357, WO 03/33495 and WO 04/018422.

Suitable chemokine receptors include, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCHD, Takeda antagonists such as N-[[4-[[[6,7-dihydro-2-(4-methylphenyl)-5H-benzocyclohepten-8-yl]carbonyl]amino]phenyl]methyl]tetrahydro-N,N-dimethyl-2H-pyran-4-aminium chloride (TAK-770), and CCR-5 antagonists described in U.S. Pat. No. 6,166,037 (particularly claims 18 and 19), WO 00/66558 (particularly claim 8), WO 00/66559 (particularly claim 9), WO 04/018425 and WO 04/026873.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine as well as those disclosed in WO 03/099807, WO 04/026841 and JP 2004107299.

Therapeutic agents for possible combination are especially one or more antiproliferative, cytostatic or cytotoxic compounds, for example one or several agents selected from the group which includes, but is not limited to, an inhibitor of polyamine biosynthesis, an inhibitor of a protein kinase, especially of a serine/threonine protein kinase, such as protein kinase C, or of a tyrosine protein kinase, such as the EGF receptor tyrosine kinase, e.g. Iressa®, the VEGF receptor tyrosine kinase, e.g. PTK787 or Avastin®, an antibody against the ligand VEGF, or the PDGF receptor tyrosine kinase, e.g. ST1571 (Glivec®), PI3K (such as BEZ235 from Novartis) and mToR inhibitors, such as rapamycin, RAD001, a cytokine, a negative growth regulator, such as TGF-β or IFN-β, an aromatase inhibitor, e.g. letrozole (Femara®) or anastrozole, an inhibitor of the interaction of an SH2 domain with a phosphorylated protein, antiestrogens, topoisomerase I inhibitors, such as irinotecan, topoisomerase II inhibitors, microtubule active agents, e.g. paclitaxel or an epothilone, alkylating agents, antiproliferative antimetabolites, such as gemcitabine or capecitabine, platin compounds, such as carboplatin or cis-platin, bisphosphonates, e.g. AREDIA® or ZOMETA®, and monoclonal antibodies, e.g. against HER2, such as trastuzumab.

The structure of the active agents identified by code nos., generic or trade names may be taken from the actual edition of the standard compendium "The Merck Index" or from databases, e.g. Patents International (e.g. IMS World Publications). The corresponding content thereof is hereby incorporated by reference.

The above-mentioned compounds, which can be used in combination with a compound of the formula (I), can be prepared and administered as described in the art, such as in the documents cited above.

Thus, the invention relates in a further embodiment to a combination, particularly a pharmaceutical composition) comprising a therapeutically effective amount of a compound of formula (I) in free form or in pharmaceutically acceptable salt form and a second therapeutically active agent, for simultaneous or sequential administration. The additional therapeutic agent is preferably selected from the group consisting of an anti-cancer agent; an anti-inflammatory agent.

The invention further relates to a method for the treatment of a disease or disorder which responds to a C-Met tyrosine kinase, especially a proliferative disorder or disease, in particular a cancer, said method comprises administration of an effective amount of a combination of pharmaceutical agents which comprise: (a) a compound of formula (I); and (b) one or more pharmaceutically active agents, to a subject in need thereof, especially human.

The invention further relates to the use of a combination of pharmaceutical agents which comprise: (a) a compound of formula (I); and (b) one or more pharmaceutically active agents for the treatment of a disease or disorder which responds to a C-Met tyrosine kinase, especially a proliferative disorder or disease, in particular a cancer.

The invention further relates to the use of a combination of pharmaceutical agents which comprise: (a) a compound of formula (I); and (b) one or more pharmaceutically active agents for the manufacture of a medicament for the treatment of a disease or disorder which responds to a C-Met tyrosine kinase, especially a proliferative disorder or disease, in particular a cancer.

The invention further relates to pharmaceutical compositions comprising (a) a compound of formula (I) and (b) a pharmaceutically active agent; and (c) a pharmaceutically acceptable carrier; wherein at least one pharmaceutically active agent is an anti-cancer therapeutic.

The present invention further relates to a commercial package or product comprising:
(a) a compound of formula (I); and (b) a pharmaceutical formulation of a pharmaceutically active agent for simultaneous, concurrent, separate or sequential use; wherein at least one pharmaceutically active agent is an anti-cancer therapeutic.

Also combinations of two or more of sequential, separate and simultaneous administration are possible, preferably such that the combination component-drugs show a joint therapeutic effect that exceeds the effect found when the combination component-drugs are used independently at time intervals so large that no mutual effect on their therapeutic efficiency can be found, a synergistic effect being especially preferred.

The term "delay of progression" as used herein means administration of the combination to patients being in a prestage or in an early phase, of the first manifestation or a relapse of the disease to be treated, in which patients, e.g., a pre-form of the corresponding disease is diagnosed or which patients are in a condition, e.g., during a medical treatment or a condition resulting from an accident, under which it is likely that a corresponding disease will develop.

The term "Jointly therapeutically active" or "joint therapeutic effect" means that the compounds may be given separately (in a chronically staggered manner, especially a sequence-specific manner) in such time intervals that they preferably, in the warm-blooded animal, especially human, to be treated, still show a (preferably synergistic) interaction (joint therapeutic effect). A joint therapeutic effect can, inter alia, be determined by following the blood levels, showing that both compounds are present in the blood of the human to be treated at least during certain time intervals.

The term "Pharmaceutically effective" preferably relates to an amount that is therapeutically or in a broader sense also prophylactically effective against the progression of a disease or disorder as disclosed herein.

The term "a commercial package" or "a product", as used herein defines especially a "kit of parts" in the sense that the components (a) and (b) as defined above can be dosed independently or by use of different fixed combinations with distinguished amounts of the components (a) and (b), i.e., simultaneously or at different time points. Moreover, these terms comprise a commercial package comprising (especially combining) as active ingredients components (a) and (b), together with instructions for simultaneous, sequential (chronically staggered, in time-specific sequence, preferentially) or (less preferably) separate use thereof in the delay of progression or treatment of a proliferative disease. The parts of the kit of parts can then, e.g., be administered simultaneously or chronologically staggered, that is at different time points and with equal or different time intervals for any part of the kit of parts. Very preferably, the time intervals are chosen such that the effect on the treated disease in the combined use of the parts is larger than the effect which would be obtained by use of only any one of the combination partners (a) and (b) (as can be determined according to standard methods. The ratio of the total amounts of the combination partner (a) to the combination partner (b) to be administered in the combined preparation can be varied, e.g., in order to cope with the needs of a patient sub-population to be treated or the needs of the single patient which different needs can be due to the particular disease, age, sex, body weight, etc. of the patients. Preferably, there is at least one beneficial effect, e.g., a mutual enhancing of the effect of the combination partners (a) and (b), in particular a more than additive effect, which hence could be achieved with lower doses of each of the combined drugs, respectively, than tolerable in the case of treatment with the individual drugs only without combination, producing additional advantageous effects, e.g., less side effects or a combined therapeutic effect in a non-effective dosage of one or both of the combination partners (components) (a) and (b), and very preferably a strong synergism of the combination partners (a) and (b).

Both in the case of the use of the combination of components (a) and (b) and of the commercial package, any combination of simultaneous, sequential and separate use is also possible, meaning that the components (a) and (b) may be administered at one time point simultaneously, followed by administration of only one component with lower host toxicity either chronically, e.g., more than 3-4 weeks of daily dosing, at a later time point and subsequently the other component or the combination of both components at a still later time point (in subsequent drug combination treatment courses for an optimal effect) or the like.

In a further aspect, the invention relates to methods of manufacturing a compound of formula (I) and intermediates thereof. A compound of the formula (I) may be prepared by processes that, though not applied hitherto for the new compounds of the present invention where they thus form new processes, are known per se. The following schemes illustrate methods for such preparations. Scheme 1 provides a general overview of synthetic strategies to obtain a compound of formula (I)

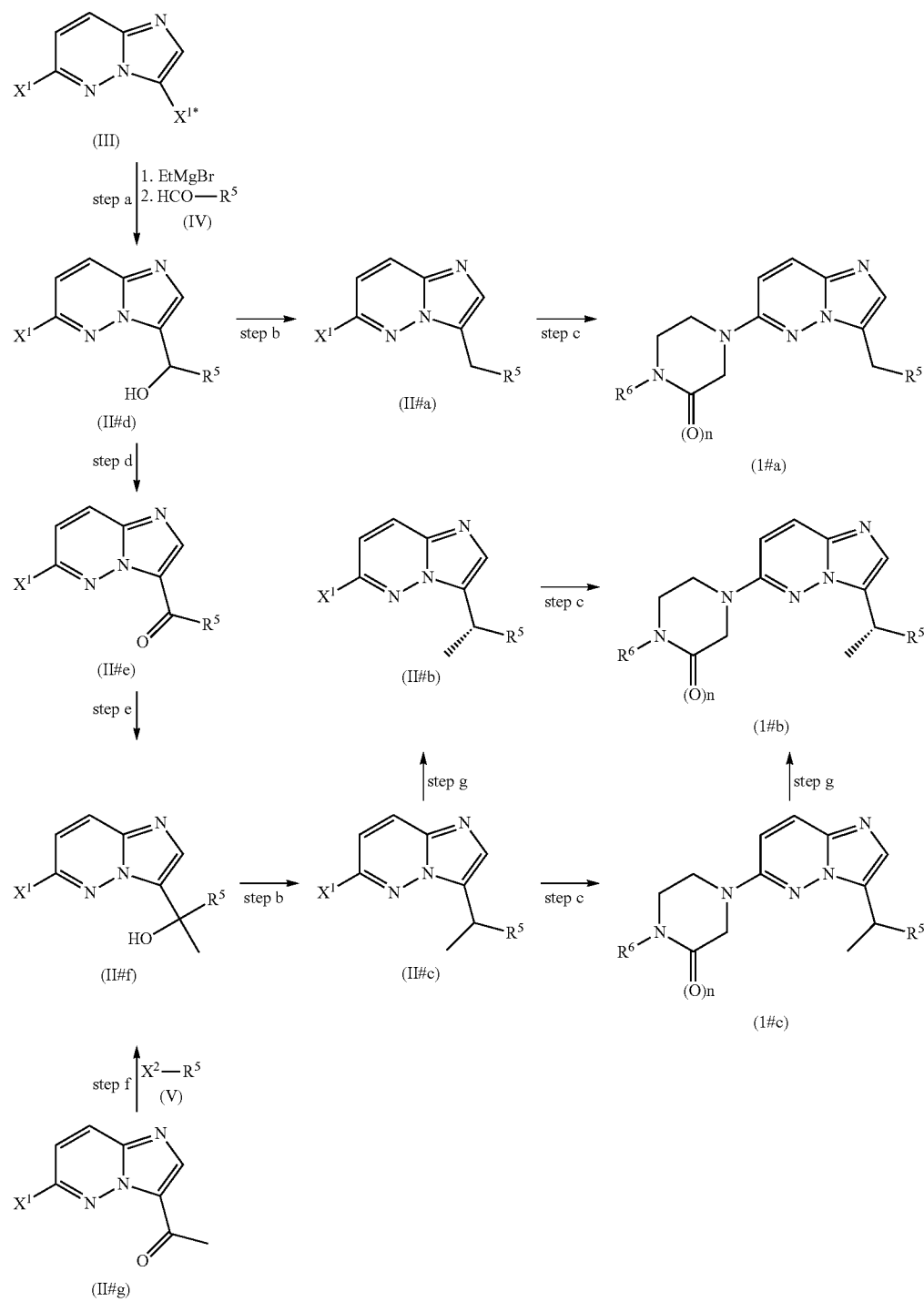

Preparation of a Compound of Formula (I#a)

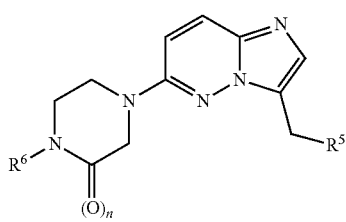
(I#a)

Step a: Reacting a Compound of Formula (III)

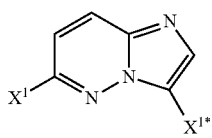
(III)

wherein $X^1$ represents a halogen, in particular chloro and $X^{1*}$ represents a halogen, in particular bromo, first with a Mg-compound of the Gringnard type, in particular EtMgBr, followed by a reaction with an aldehyde of formula (IV) to obtain a compound of formula (II#d)

$$HCO-R^5 \quad (IV)$$

wherein $R^5$ is as defined herein, and

Step b: Reacting a Compound of Formula (II#d)

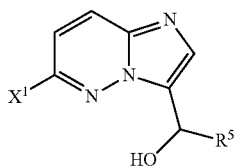
(II#d)

wherein the substituents are as defined herein, with a reducing agent, such as a combination of hypophosphoric acid and iodine to obtain a compound of formula (II#a), and Step c: Reacting a Compound of Formula (II#a)

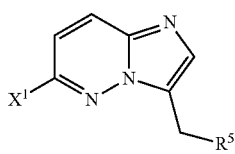
(II#a)

wherein the substituents are as defined herein, with an amine of formula $R^1R^2NH_2$, preferably a pipererazine or piperazinone derivative in presence of KF or KF and N-ethyldiisopropylamine in an organic solvent, preferably N-methylpyrrolidone to obtain a compound of formula (I#a)

Preparation of a Compound of Formula (I#c)

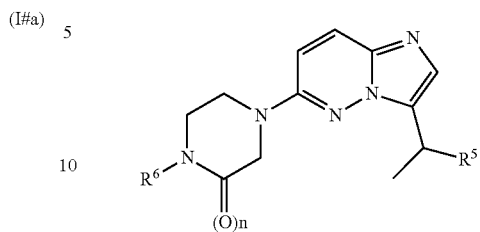

Step d: Reacting a Compound of Formula (II#d)

(II#d)

wherein the substituents are as defined herein, with oxidizing agents, such as Dess-Martin periodinane or 2-iodoxybenzoic acid to obtain a compound of formula (II#e), and Step e: Reacting a Compound of Formula (II#e)

(II#e)

wherein the substituents are as defined herein, with methyl magnesium to obtain a compound of formula (II#f)

or alternatively by

Step f: Reacting a Compound of Formula (II#g)

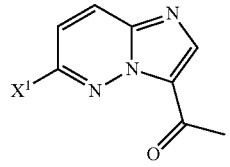
(II#g)

wherein the substituents are as defined herein, with an organolithium species obtained from $X^2-R^5$ (V) (wherein $X^2$ is H or could alternatively be halo such as Br or I) and lithium diisopropylamide or butyl lithium to obtain a compound of formula (II#f)
and reacting a compound of formula (II#f)

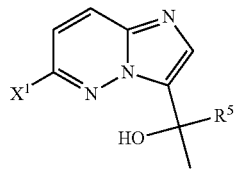
(II#f)

in analogy to step b to obtain a compound of formula (II#c)
and reacting a compound of formula (II#c)

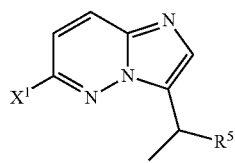
(II#c)

in analogy to step c to obtain a compound of formula (I#c)
Preparation of a Compound of Formula (I#b)
Step g: Separating the Enantiomers of a Compound of Formula (II#c)

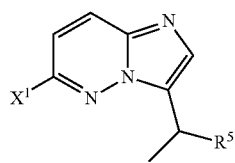
(II#c)

wherein the substituents are as defined herein, by using chiral chromatography to obtain a pure enantiomer of formula (II#b)
and reacting a compound of formula (II#b)

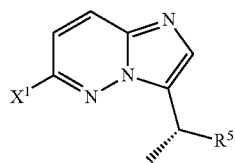
(II#b)

in analogy to step c to obtain a compound of formula (I#b)
or alternatively by
reacting a compound of formula (II#c)

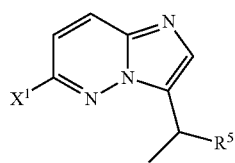
(II#c)

in analogy to step c to obtain a compound of formula (I#c)
and separating the enantiomers of a compound of formula (I#c)

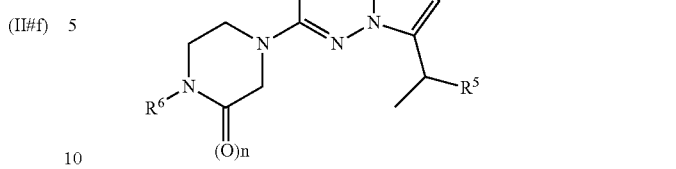
(I#c)

in analogy to step g obtain a compound of formula (I#b)

Scheme 2

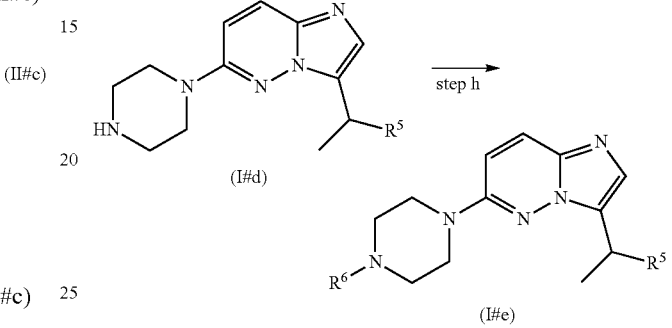
(I#d)
(I#e)

Alternative Preparation of a Compound of Formula (I#e)
Step h: Reacting a Compound of Formula (I#d)

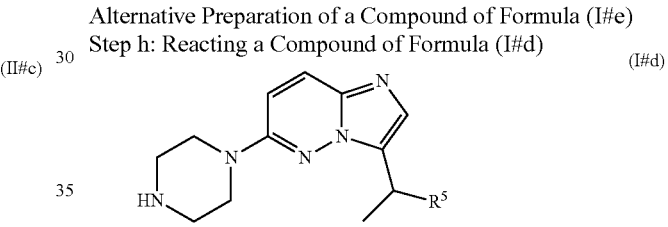
(I#d)

with alkylating, or acylating (preferably acylating) agents such a acetyl chloride or 4-nitrophenyl formate or methyl chloroformate in presence of an organic base such as pyridine to obtain a compound of formula (I#e)

Reaction Conditions

Where temperatures are given hereinbefore or hereinafter, "about" has to be added, as minor deviations from the numeric values given, e.g. variations of ±10%, are tolerable. All reactions may take place in the presence of one or more diluents and/or solvents. The starting materials may be used in equimolar amounts; alternatively, a compound may be used in excess, e.g. to function as a solvent or to shift equilibrium or to generally accelerate reaction rates. Reaction aids, such as acids, bases or catalysts may be added in suitable amounts, as known in the field, required by a reaction and in line with generally known procedures.

Protecting Groups

If one or more other functional groups, for example carboxy, hydroxy, amino, sulfhydryl or the like are or need to be protected in a starting material as described herein or any other precursor, because they should not take part in the reaction or disturb the reaction, these are such groups as are usually used in the synthesis of peptide compounds, and also of cephalosporins and penicillins, as well as nucleic acid derivatives and sugars. Protecting groups are such groups that are no longer present in the final compounds once they are removed, while groups that remain as substituents are not protecting groups in the sense used here which are groups that are added at a starting material or intermediate stage and removed to obtain a final compound. Also in the case of conversions of a compound of the formula (I) into a different compound of the formula (I), protecting groups may be introduced and removed, if useful or required.

The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by acetolysis, protonolysis, solvolysis, reduction, photolysis or also by enzyme activity, for example under conditions analogous to physiological conditions, and that they are not present in the end-products. The specialist knows, or can easily establish, which protecting groups are suitable with the reactions mentioned above and below. The protection of such functional groups by such protecting groups, the protecting groups themselves, and their removal reactions are described for example in standard reference works, such as J. F. W. McOmie, "Protective Groups in Organic Chemistry", Plenum Press, London and New York 1973, in T. W. Greene, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (*Methods of organic chemistry*), Houben Weyl, 4th edition, Volume 15/I, Georg Thieme Verlag, Stuttgart 1974, in H.-D. Jakubke and H. Jescheit, "Aminosauren, Peptide, Proteine" (Amino acids, peptides, proteins), Verlag Chemie, Weinheim, Deerfield Beach, and Basel 1982, and in Jochen Lehmann, "Chemie der Kohlenhydrate: Monosaccharide and Derivate" (*Chemistry of carbohydrates: monosaccharides and derivatives*), Georg Thieme Verlag, Stuttgart 1974.

Salts of a compound of formula (I) with a salt-forming group may be prepared in a manner known per se. Acid addition salts of compounds of formula (I) may thus be obtained by treatment with an acid or with a suitable anion exchange reagent. A salt with two acid molecules (for example a dihalogenide of a compound of formula (I)) may also be converted into a salt with one acid molecule per compound (for example a monohalogenide); this may be done by heating to a melt, or for example by heating as a solid under a high vacuum at elevated temperature, for example from 130 to 170° C., one molecule of the acid being expelled per molecule of a compound of formula (I). Salts can usually be converted to free compounds, e.g. by treating with suitable basic compounds, for example with alkali metal carbonates, alkali metal hydrogencarbonates, or alkali metal hydroxides, typically potassium carbonate or sodium hydroxide.

Stereoisomeric mixtures, e.g. mixtures of diastereomers, can be separated into their corresponding isomers in a manner known per se by means of suitable separation methods. Diastereomeric mixtures for example may be separated into their individual diastereomers by means of fractionated crystallization, chromatography, solvent distribution, and similar procedures. This separation may take place either at the level of a starting compound or in a compound of formula (I) itself. Enantiomers may be separated through the formation of diastereomeric salts, for example by salt formation with an enantiomer-pure chiral acid, or by means of chromatography, for example by UPLC, using chromatographic substrates with chiral ligands.

It should be emphasized that reactions analogous to the conversions mentioned in this chapter may also take place at the level of appropriate intermediates (and are thus useful in the preparation of corresponding starting materials).

The following examples illustrate the invention without limiting the scope thereof. In the examples provided, temperatures are measured in degrees Celsius. Unless otherwise indicated, the reactions take place at rt. Further, if not indicated otherwise, the analytical UPLC conditions are as follows:
Conditions 1:
The flow is 2 mL/min of acetonitrile and water (both +0.1% TFA)
0-8.0 min: 2% to 100% of acetonitrile
8.0-10.0 min: 100% of acetonitrile
Column: Chromolith Performance, RP-18e 4.6×100 mm from Merck
Conditions 2:
The flow is 0.7 mL/min of 20% n-hexane and 80% ethanol
Column: Chiralpak AD, 4.6×250 mm from Daicel
Conditions 3:
The flow is 0.7 mL/min of 20% n-hexane and 80% ethanol
Column: Chiralcel OJ, 4.6×250 mm from Daicel
Conditions 4:
The flow is 2 mL/min of acetonitrile and water (both +0.1% TFA)
0-2.2 min: 5% to 95% of acetonitrile
2.2-2.7 min: 95% of acetonitrile
2.7-2.9 min: 95% to 5% of acetonitrile
2.9-3.5 min: 5% of acetonitrile
Column: Sunfire C18 3.5 μm, 2.1×20 mm from Waters
Conditions 5:
The flow is 2 mL/min of acetonitrile and water (both +0.1% formic acid)
0-8.0 min: 2% to 100% of acetonitrile
8.0-10.0 min: 100% of acetonitrile
Column: Chromolith Performance, RP-18e 4.6×100 mm from Merck
Precolumn: Chromolith Performance, RP-18e 4.6×5 mm from Merck
Conditions 6:
The flow is 2 mL/min of acetonitrile and water (both +0.1% TFA)
0-2.2 min: 5% to 95% of acetonitrile
2.2-2.7 min: 95% of acetonitrile
Column Atlantis T3 3 μm 4.6×30 mm from Waters.

In the following examples, the abbreviations given below are used:
atm. atmosphere
DCM dichloromethane
DMF N,N-dimethylformamide
DMSO dimethyl sulfoxide
eq. equivalent(s)
$Et_2O$ diethyl ether
EtOAc ethyl acetate
h hour(s)
UPLC High Performance Liquid Chromatography
HV high vacuum
LDA lithium diisopropylamide
MeOH methanol
Min minute(s)
mL milliliter(s)
MPLC Medium Pressure Liquid Chormatography
MS mass spectrometry
MW microwave
n-BuLi n-Butyllithium
NMP N-Methylpyrrolidinone
RM reaction mixture
RT room temperature
SPE solid phase extraction
TBME methyl tert-butyl ether TFA trifluoroacetic acid
THF tetrahydrofuran
$t_R$ retention time
UPLC ultra performance liquid chomatography
UV Ultraviolet Synthesis of Intermediates Synthesis of Intermediates A, B, C and D

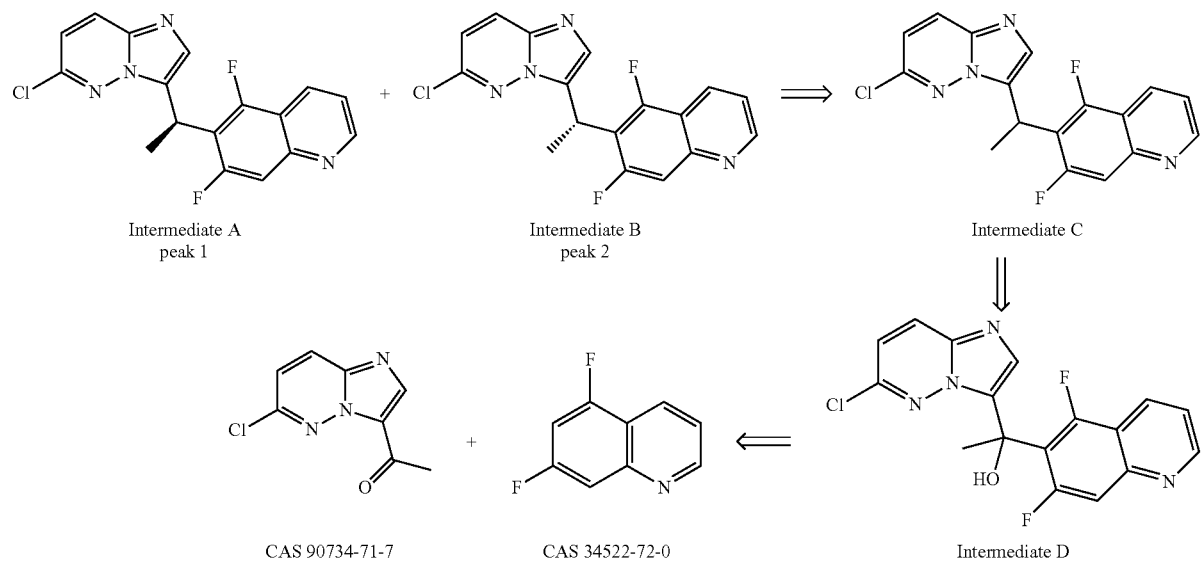

Intermediate A
peak 1

Intermediate B
peak 2

Intermediate C

CAS 90734-71-7

CAS 34522-72-0

Intermediate D

Intermediate A

6-[(R)-1-(6-Chloro-imidazo[1,2-b]pyridazin-3-yl)-ethyl]-5,7-difluoro-quinoline

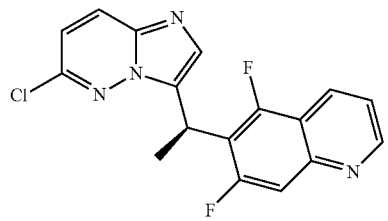 [SMILES: C[C@H](c1c(F)cc2ncccc2c1F)c1cnc2ccc(Cl)nn12]

and

Intermediate B

6-[(S)-1-(6-Chloro-imidazo[1,2-b]pyridazin-3-yl)-ethyl]-5,7-difluoro-quinoline

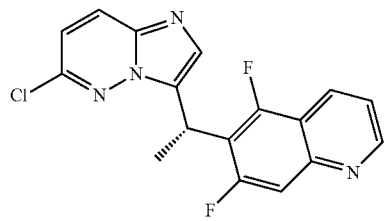 [SMILES: C[C@@H](c1c(F)cc2ncccc2c1F)c1cnc2ccc(Cl)nn12]

The title compounds were obtained from the chiral separation of (rac)-6-[1-(6-chloro-imidazo[1,2-b]pyridazin-3-yl)-ethyl]-5,7-difluoro-quinoline (Intermediate C, 10.0 g, 28.5 mmol) using a preparative UPLC (column: AD-H Temperature: 40° C.; mobile phase: methanol/CO2=40/60 flow rate: 3 mL/min; back pressure: 150 bar) as white solids:

Intermediate A (peak 1): ($t_R$ 3.60 min (conditions 1), $t_R$ 9.76 min (conditions 2), $^1$H-NMR in DMSO-d6: 8.93 (d, 1H); 8.43 (d, 1H); 8.16 (d, 1H); 7.93 (s, 1H); 7.67 (d, 1H); 7.58 (m, 1H); 7.25 (d, 1H); 5.06 (q, 1H); 1.88 (d, 3H)).

Intermediate B (peak 2): ($t_R$ 3.60 min (conditions 1), $t_R$ 10.87 min (conditions 2), $^1$H-NMR in DMSO-d6: 8.93 (s, 1H); 8.43 (d, 1H); 8.16 (d, 1H); 7.93 (s, 1H); 7.67 (d, 1H); 7.58 (m, 1H); 7.25 (d, 1H); 5.06 (q, 1H); 1.88 (d, 3H)).

Intermediate C (rac)-6-[1-(6-Chloro-imidazo[1,2-b]pyridazin-3-yl)-ethyl]-5,7-difluoro-quinoline

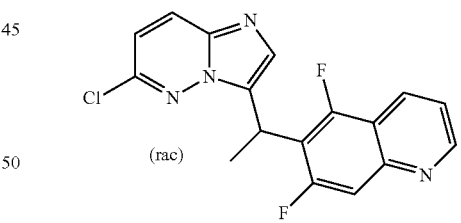

(rac)-1-(6-Chloro-imidazo[1,2-b]pyridazin-3-yl)-1-(5,7-difluoro-quinolin-6-yl)-ethanol (Intermediate D, 23.2 g, 63.7 mmol was dissolved in acetic acid (317 mL) and introduced in 23 microwave reactor-vials. Iodide (2.11 g×23, 191 mmol), followed by H$_3$PO$_2$ 50% (2.28 mL×23, 464 mmol) were then added into each vial. Then they were submitted to microwave irradiations 5 min at 150° C. The combined RMs were concentrated in vacuo and the residue was diluted with water, basified by a 4 M NaOH solution and extracted with EtOAc (3×). The organics were joined and washed with brine, dried over Na$_2$SO$_4$ and the solvent was removed. The residue was triturated with diisopropyl ether. The precipitate formed was filtered off to give a beige solid ($t_R$ 3.60 min (conditions 1), $t_R$ 9.76/10.87 min (conditions 2), MH+=345, $^1$H-NMR in DMSO-d6: 8.93 (d, 1H); 8.43 (d, 1H); 8.16 (d, 1H); 7.93 (s, 1H); 7.67 (d, 1H); 7.58 (m, 1H); 7.25 (d, 1H); 5.06 (q, 1H); 1.88 (d, 3H)).

Intermediate D (rac)-1-(6-Chloro-imidazo[1,2-b]pyridazin-3-yl)-1-(5,7-difluoro-quinolin-6-yl)-ethanol

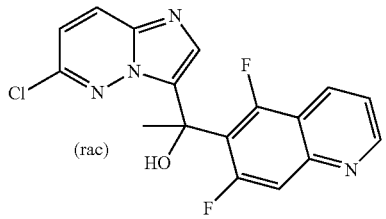 [SMILES: CC(O)(c1c(F)cc2ncccc2c1F)c1cnc2ccc(Cl)nn12]

A solution of 5,7-difluoro-quinoline (CAS 34522-72-0, 18.57 g, 112 mmol) in dry THF (120 mL) was added dropwise to a freshly prepared solution of LDA (n-BuLi 77 mL and diisopropylamine 18.94 mL, 123 mmol, in 500 mL THF) at −78° C. The solution was stirred at this temperature for 1 h, and then the solution of 1-(6-chloro-imidazo[1,2-b]pyridazin-3-yl)ethanone (CAS 90734-71-7, 20.0 g, 102 mmol) in 400 mL THF was added dropwise at −70° C. After stirring additional 45 min at −70 to −30° C. the RM was quenched with 1M NH$_4$Cl, diluted with water, and extracted with EtOAc (3×). The organic layers were washed with brine, dried over Na$_2$SO$_4$, filtered and concentrated. The residue was purified by flash chromatography and then crystallized in DCM to afford the title compound as a beige solid (t$_R$ 2.94 min (conditions 1), MH+=361, $^1$H-NMR in DMSO-d6: 8.93 (d, 1H); 8.43 (d, 1H); 8.18 (d, 1H); 7.92 (s, 1H); 7.57 (m, 2H); 7.24 (d, 1H); 6.49 (s, 1H); 2.18 (s, 3H)).

Synthesis of intermediates E, F and G

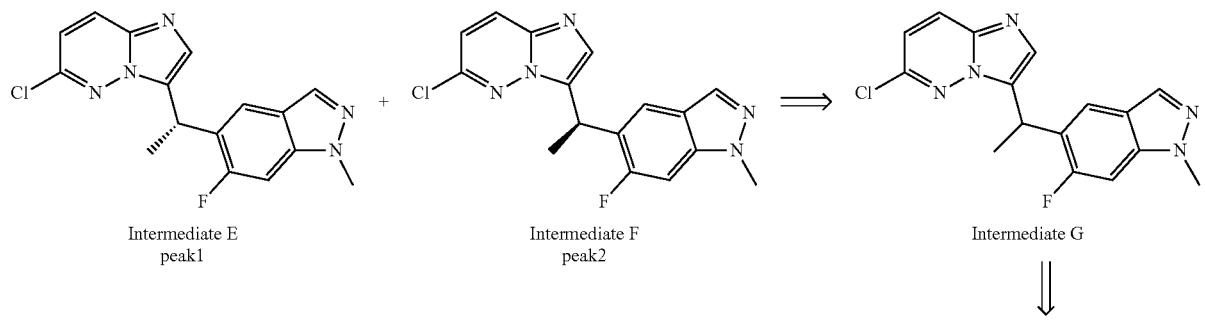

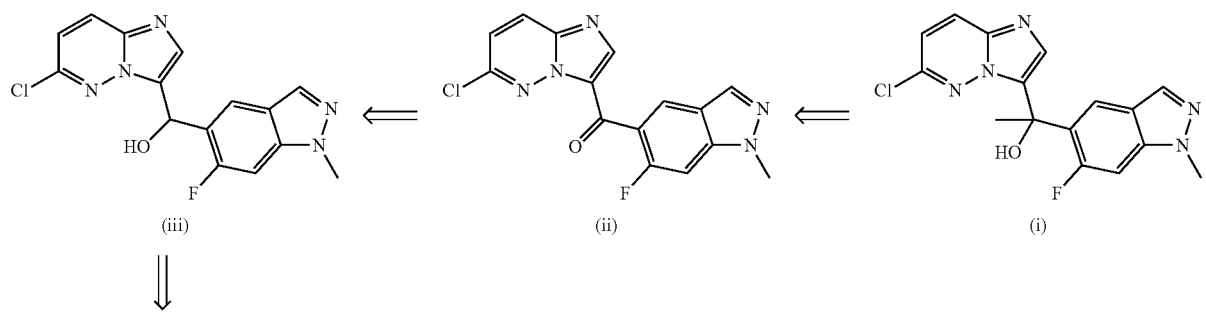

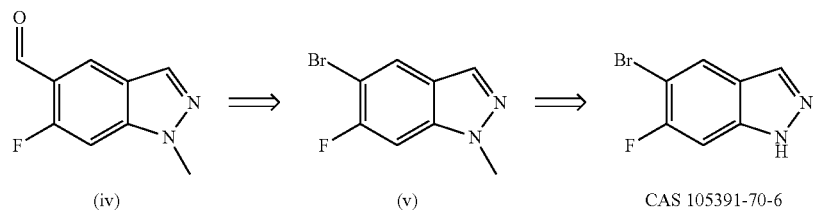

Intermediate E

6-Chloro-3-[(S)-1-(6-fluoro-1-methyl-1H-indazol-5-yl)-ethyl]-imidazo[1,2-b]pyridazine

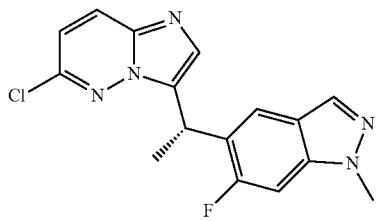 [SMILES: C[C@@H](c1cc2cnn(C)c2cc1F)c1cnc2ccc(Cl)nn12]

and

Intermediate F

6-Chloro-3-[(R)-1-(6-fluoro-1-methyl-1H-indazol-5-yl)-ethyl]-imidazo[1,2-b]pyridazine

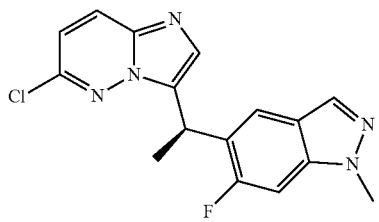 [SMILES: C[C@H](c1cc2cnn(C)c2cc1F)c1cnc2ccc(Cl)nn12]

The title compounds were obtained from the chiral separation of (rac)-6-chloro-3-[1-(6-fluoro-1-methyl-1H-indazol-5-yl)-ethyl]-imidazo[1,2-b]pyridazine (Intermediate G, 10.0 g, 30.3 mmol) using a preparative UPLC (column: OD Sepaxcel; Temperature: 39° C.; mobile phase: methanol/CO2=30/70; flow rate: 3 mL/min; back pressure: 151 bar) as slightly yellow solids:

Intermediate E (peak 1): ($t_R$ 4.04 min (conditions 1), $t_R$ 14.39 min (conditions 2), $^1$H-NMR in DMSO-d6: 8.19 (d, 1H); 7.92 (s, 1H); 7.80 (s, 1H); 7.55 (d, 1H); 7.42 (d, 1H); 7.28 (d, 1H); 4.84 (m, 1H); 3.96 (s, 3H); 1.71 (d, 3H)).

Intermediate F (peak 2): ($t_R$ 4.04 min (conditions 1), $t_R$ 16.40 min (conditions 2), $^1$H-NMR in DMSO-d6: 8.19 (d, 1H); 7.92 (s, 1H); 7.80 (s, 1H); 7.55 (d, 1H); 7.42 (d, 1H); 7.28 (d, 1H); 4.84 (m, 1H); 3.96 (s, 3H); 1.71 (d, 3H)).

Intermediate G (rac)-6-Chloro-3-[1-(6-fluoro-1-methyl-1H-indazol-5-yl)-ethyl]-imidazo[1,2-b]pyridazine

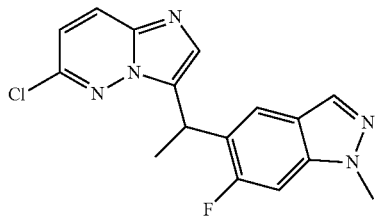 [SMILES: CC(c1cc2cnn(C)c2cc1F)c1cnc2ccc(Cl)nn12]

(rac)-1-(6-Chloro-imidazo[1,2-b]pyridazin-3-yl)-1-(6-fluoro-1-methyl-1H-indazol-5-yl)-ethanol ((i), 21.4 g, 61.9 mmol) was dissolved in acetic acid (310 mL) and introduced in 20 microwave reactor-vials. Iodide (2.36 g×20, 186 mmol), followed by $H_3PO_2$ 50% (2.56 mL×20, 464 mmol) were then added into each vial. Then they were submitted to microwave irradiations 10 min at 150° C. The combined RMs were concentrated in vacuo and the residue was diluted with water, basified by a 4 M NaOH solution and extracted twice with EtOAc. The organics were joined and washed with brine, dried over $Na_2SO_4$ and the solvent was removed. The residue was triturated with diisopropyl ether. The precipitate formed was filtered off to give a beige solid ($t_R$ 4.08 min (conditions 1), $t_R$ 14.39/16.40 min (conditions 2), MH+=330, $^1$H-NMR in DMSO-d6: 8.19 (d, 1H); 7.92 (s, 1H); 7.80 (s, 1H); 7.55 (d, 1H); 7.42 (d, 1H); 7.28 (d, 1H); 4.84 (m, 1H); 3.96 (s, 3H); 1.71 (d, 3H)).

(rac)-1-(6-Chloro-imidazo[1,2-b]pyridazin-3-yl)-1-(6-fluoro-1-methyl-1H-indazol-5-yl)ethanol (i)

To a stirred suspension of (6-chloro-imidazo[1,2-b]pyridazin-3-yl)-(6-fluoro-1-methyl-1H-indazol-5-yl)-methanone ((ii), 25.45 g, 74 mmol) and THF (4 L) was added methyl magnesium bromide (3 M, 43 mL) at 38° C. during 15 min. The mixture was stirred at 38° C. for 20 min. The RM was cooled to RT, quenched with 1M $NaHCO_3$ and extracted with EtOAc (3×). The organic layers were washed with brine, dried over $Na_2SO_4$, filtered and concentrated. The title compound was obtained after crystallization in DCM-TBME (1:2) as a beige solid ($t_R$ 3.30 min (conditions 1); MH+=346).

(6-Chloro-imidazo[1,2-b]pyridazin-3-yl)-(6-fluoro-1-methyl-1H-indazol-5-yl)-methanone (ii)

To a stirred suspension of (rac)-6-chloro-imidazo[1,2-b]pyridazin-3-yl)-(6-fluoro-1-methyl-1H-indazol-5-yl)-methanol ((iii), 25.5 g, 77 mmol) and acetone (2 L) was added 2-iodoxybenzoic acid (CAS 61717-82-6 44.4 g, 154 mmol) at RT. The mixture was stirred for 7 h at reflux temperature. The RM was cooled to RT and concentrated in vacuo.

To the residue was added water (1 L) and 1M NaOH (1 L) and the resulting suspension was stirred over night at RT. The crystals were filtered off, washed with water (3×) and dried to afford the title compound as a beige solid ($t_R$ 4.06 min (conditions 1); MH+=330.0).

(rac)-6-chloro-imidazo[1,2-b]pyridazin-3-yl)-(6-fluoro-1-methyl-1H-indazol-5-yl)methanol (iii)

3-Bromo-6-chloro-imidazo[1,2-b]pyridazine (CAS 13526-66-4, 19.69 g, 85 mmol) was suspended in THF (303 mL) and the ethylmagnesium solution (1 M, 102 mL) was added slowly at 0-5° C. under argon condition. The RM was stirred for 30 min at RT. The RM was cooled to 0° C. and the solution of 6-fluoro-1-methyl-1H-indazole-5-carbaldehyde ((iv), 15.4 g, 85 mmol) in THF (303 mL) was added slowly at 0-5° C. The RM was stirred additional 2 h at RT. The RM was concentrated in vacuo. To the residue was added water (0.5 L) and the resulting suspension was stirred over night at RT. The crystals were filtered off, washed with water (1×) and dried. To the crude product was added EtOAc (0.5 L) and the resulting suspension was stirred over night at RT. The crystals were filtered off, washed with EtOAc (1×) and dried to afford the title compound as a beige solid ($t_R$ 3.26 min (conditions 1); $^1$H-NMR in DMSO-d6: 8.22 (d, 1H); 8.07 (s, 1H); 7.90 (d, 1H); 7.50 (d, 1H); 7.48 (s, 1H); 7.37 (d, 1H); 6.44 (d, 1H); 6.30 (d, 1H); 2.48 (s, 3H)).

6-Fluoro-1-methyl-1H-indazole-5-carbaldehyde (iv)

A 2 M solution of n-butyl magnesium chloride in THF (22.4 mL, 44.8 mmol) was added to toluene (160 mL) under nitrogen and cooled to −10° C. To this was added a 1.6 M solution of n-butyl lithium in hexane (57 mL, 91 mmol) and after 1 h, the RM was cooled to −30° C. To the RM was then added a solution of 5-bromo-6-fluoro-1-methyl-1H-indazole ((v) 19.0 g, 83 mmol) in THF (160 mL) and the reaction was warmed up to −10° C. After 1 h, DMF (8.23 mL, 106 mmol) was added and the RM was stirred at −10° C. for another 1 h. The reaction was quenched using 2 N HCl and was allowed to warm up to room temperature. After 30 min, the RM was basified with saturated aqueous NaHCO$_3$ solution and then extracted with EtOAc. The organic phase was washed with brine, dried over Na$_2$SO$_4$ and evaporated under vacuo. The residue was triturated with Et$_2$O. The precipitate formed was filtered off to give a beige solid identified as the desired aldehyde (t$_R$ 3.61 min (conditions 1), NMR in DMSO-d6: 10.16 (s, 1H); 8.36 (d, 1H); 8.30 (s, 1H); 7.70 (d, 1H); 4.03 (s, 3H)).

5-Bromo-6-fluoro-1-methyl-1H-indazole (v)

To a suspension of NaH (8.84 g, 221 mmol) in THF (50 mL) was added dropwise a solution of 5-bromo-6-fluoro-1H-indazole (CAS 105391-70-6, 44.1 g, 201 mmol) in THF (200 mL) at 5° C. After 15 min at 5° C., MeI (31.7 mL, 221 mmol) was added at 5° C. and the RM was stirred between 0° C. and 5° C. for 1.5 h. The reaction was quenched with 0.5 M HCl and extracted with EtOAc. The organic phases were combined, washed with brine, dried over Na$_2$SO$_4$ and evaporated under vacuo. The 2 isomers formed were separated by MPLC with heptane and EtOAc to afford the title compound as a yellow solid (t$_R$ 5.07 min (conditions 1), NMR in DMSO-d6: 8.14 (d, 1H); 8.04 (s, 1H); 7.79 (d, 1H); 4.00 (s, 3H)).

Synthesis of Intermediate H and I

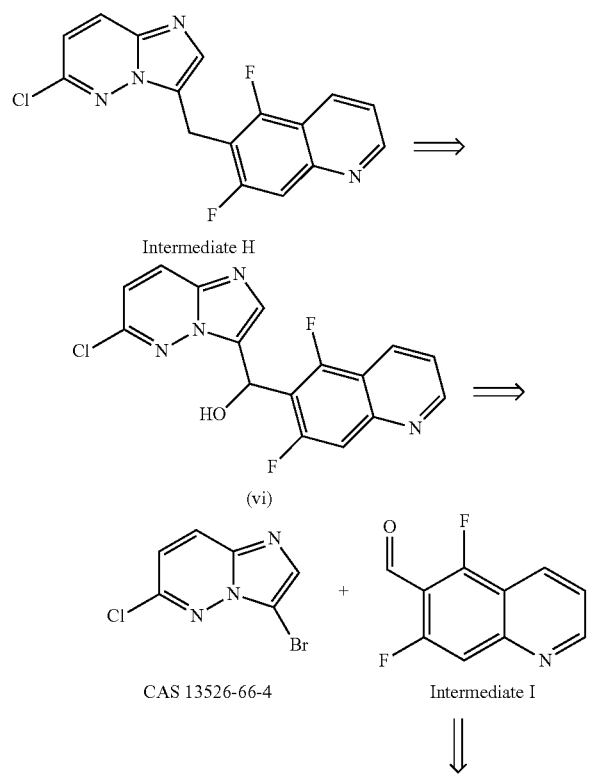

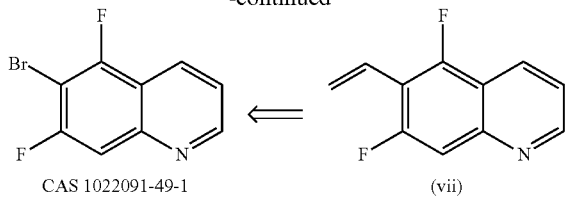

Intermediate H 6-(6-Chloro-imidazo[1,2-b]pyridazin-3-ylmethyl)-5,7-difluoro-quinoline

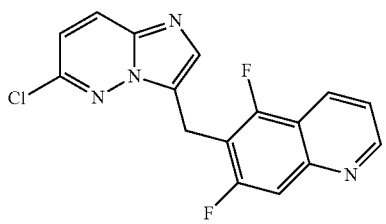 [SMILES: Fc1cc2ncccc2c(F)c1Cc1cnc2ccc(Cl)nn12]

To the stirred solution of (rac)-6-chloro-imidazo[1,2-b]pyridazin-3-yl)-(5,7-difluoro-quinolin-6-yl)-methanol ((vi), 21.0 g, 60.6 mmol) and acetic acid (303 mL) were added H$_3$PO$_2$ 50% (33.3 mL, 303 mmol), followed by iodide (30.7 g, 121 mmol). The mixture was stirred 2 h at reflux temperature (oil bath temperature=130° C.). The RM was concentrated in vacuo and the residue was diluted with water, basified with 2M NaOH solution and extracted twice with DCM. The organics were joined, dried over Na$_2$SO$_4$ and the solvent was removed. The residue was triturated with Et$_2$O. The precipitate formed was filtered off to give a beige solid (t$_R$ 3.55 min (conditions 1), MH+=331.0, NMR in DMSO-d6: 8.97 (d, 1H); 8.48 (d, 1H); 8.19 (d, 1H); 7.74 (d, 1H); 7.61 (d, 1H); 7.60 (s, 1H); 7.33 (d, 1H); 4.50 (s, 2H)).

(rac)-6-Chloro-imidazo[1,2-b]pyridazin-3-yl)-(5,7-difluoro-quinolin-6-yl)-methanol (vi)

3-Bromo-6-chloro-imidazo[1,2-b]pyridazine (CAS 13526-66-4, 15.0 g, 63.9 mmol) was suspended in THF (235 mL), cooled to 0° C. and the ethylmagnesium solution (1 M, 77 mL) was added slowly at 0-5° C. under argon condition. The RM was stirred at RT for 30 min. The RM was cooled to 0° C. and the solution of 5,7-difluoro-quinoline-6-carbaldehyde (Intermediate I, 12.46 g, 63.9 mmol) in THF (235 mL) was added dropwise. The RM was stirred an additional hour at RT and then concentrated in vacuo. To the residue was added water (0.4 L) and the resulting suspension was stirred over night at RT. The crystals were filtered off, washed with water (1×) and dried. To the crude product was added EtOAc (0.5 L) and the resulting suspension was stirred 2 h at RT. The crystals were filtered off, washed with EtOAc (1×) and dried to afford the title compound as a beige solid (t$_R$ 2.94 min (conditions 1), MH+=347).

Intermediate I

5,7-Difluoro-quinoline-6-carbaldehyde

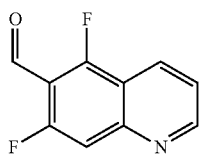

5,7-Difluoro-6-vinyl-quinoline ((vii), 614 mg, 3.21 mmol) was dissolved in dioxane (1.7 mL) and water (0.6 mL). 2,6-lutidine (0.761 mL, 6.42 mmol), sodium periodate (2.75 g, 12.85 mmol) and osmium tetroxide (653 mg, 0.064 mmol) were added to the previous solution. The RM was stirred at RT for 15 min. A precipitate was formed. Water was added to the RM and it was extracted twice with EtOAc. The organics were joined and washed with brine, dried over Na$_2$SO$_4$ and the solvent was removed. The residue was purified by MPLC with Hexane and EtOAc to give the title compound as a white solid (t$_R$ 1.2 min (conditions 4), MH+=244, $^1$H-NMR in DMSO-d6: 10.36 (s, 1H); 9.15 (s, 1H); 8.65 (d, 1H); 7.79 (d, 1H); 7.69 (dd, 1H)).

5,7-Difluoro-6-vinyl-quinoline (vii)

6-Bromo-5,7-difluoro-quinoline ((viii), 1 g, 4.10 mmol), tetrakis(triphenylphosphine)palladium (0) (47 mg, 0.041 mmol) and tributyl(vinyl)tin (1.34 g, 4.10 mmol) were put together with dioxane (3.7 mL) in a microwave reactor and stirred for 25 min at 150° C. under microwave irradiations. The solvent was removed and the residue was purified by MPLC with hexane and EtOAc. The title compound was obtained as a colorless oil (t$_R$ 1.1 min (conditions 4), MH+=192).

Synthesis of Intermediates J, K and L

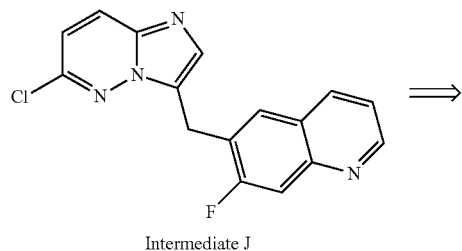

Intermediate J

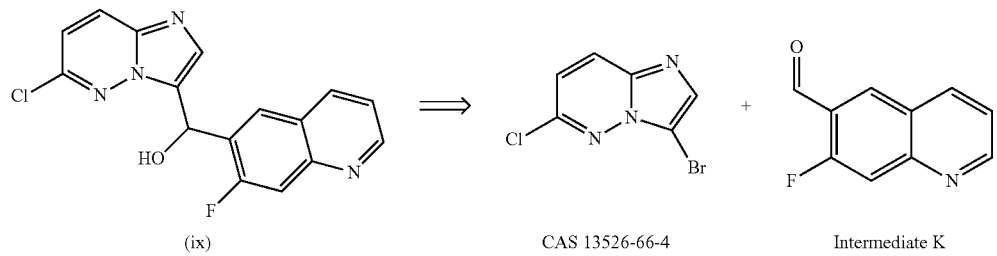

(ix)     CAS 13526-66-4     Intermediate K

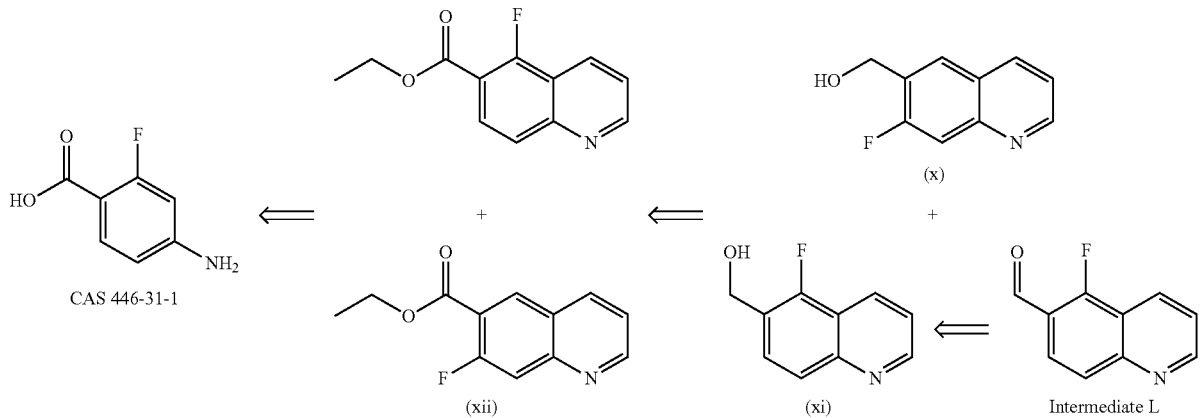

Intermediate J

6-(6-Chloro-imidazo[1,2-b]pyridazin-3-ylmethyl)-7-fluoro-quinoline

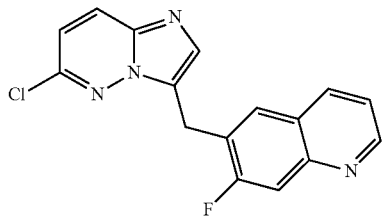 [SMILES: Fc1cc2ncccc2cc1Cc1cnc2ccc(Cl)nn12]

The title compound was obtained from (rac)-(6-chloro-imidazo[1,2-b]pyridazin-3-yl)-(7-fluoro-quinolin-6-yl)-methanol (ix) treated with iodine and $H_3PO_2$ in the conditions described in Intermediate H ($t_R$ 4.41 min (conditions 5), MH+=313).

(rac)-(6-Chloro-imidazo[1,2-b]pyridazin-3-yl)-(7-fluoro-quinolin-6-yl)-methanol (ix)

3-Bromo-6-chloro-imidazo[1,2-b]pyridazine (CAS 13526-66-4, 1.327 g, 5.71 mmol) was dissolved THF (40 mL) and under nitrogen conditions, it was cooled down to 0° C. and ethylmagnesium bromide solution (1 M, 6.85 mL) was added. The RM was stirred at RT for 30 min then a solution of 7-fluoro-quinoline-6-carbaldehyde (Intermediate K, 1.0 g, 5.71 mmol) in THF (20 mL) was added by 0° C. The RM was stirred at RT for 2 h. The solvent was partially removed by evaporation and water (40 mL) was added to the residual mash. After 1 h stirring, the crystallized product was filtered and dried overnight under vacuum to afford the title compound as a powder ($t_R$ 3.70 min (conditions 5), MH+=329, $^1$H-NMR in DMSO-d6: 8.90 (dd, 1H); 8.46 (d, 1H); 8.29-8.23 (m, 2H); 7.72 (d, 1H); 7.54-7.49 (m, 2H); 7.40 (d, 1H); 6.56-6.49 (m, 2H)).

Intermediate K

7-Fluoro-quinoline-6-carbaldehyde

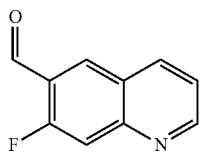

and

Intermediate L

5-Fluoro-quinoline-6-carbaldehyde

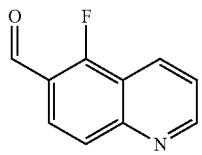 [SMILES: O=Cc1ccc2ncccc2c1F]

The title compounds were each obtained from the treatment of the corresponding regioisomer (x) respectively (xi) dissolved in DCM, with 10 eq. $MnO_2$ at RT. After 16 h stirring, the black solid was filtered off over celite and the solvent was removed to obtain a white solid.

Intermediate K ($t_R$ 4.04 min (conditions 5), MH+=176, $^1$H-NMR in DMSO-d6: 10.31 (s, 1H); 9.05 (s, 1H); 8.66 (d, 1H); 8.63 (d, 1H); 7.91 (d, 1H); 7.64 (dd, 1H)).

Intermediate L ($t_R$ 4.37 min (conditions 5), MH+=176, $^1$H-NMR in DMSO-d6: 10.47 (s, 1H); 9.13 (s, 1H); 8.70 (d, 1H); 8.05 (t, 1H); 7.97 (d, 1H); 7.75 (dd, 1H)).

(7-Fluoro-quinolin-6-yl)-methanol (x) and (5-fluoro-quinolin-6-yl)-methanol (xi)

A mixture of regioisomers ((xii), 792 mg, 3.6 mmol) was dissolved in THF (7.5 mL) under nitrogen and cooled down to 0° C. with an ice-water bath. Then a solution of $LiAlH_4$ (1 M in THF, 4.3 mL) was added slowly. The precipitate formed was filtered off and the filtrate was concentrated. The residue was purified by MPLC eluting with a DCM/MeOH gradient to afford:

(7-Fluoro-quinolin-6-yl)-methanol (x) as a white solid ($t_R$ 0.3 min (conditions 6), MH+=178).

(5-Fluoro-quinolin-6-yl)-methanol (xi) as a yellow solid pure at 79% by $^1$H-NMR ($t_R$ 0.3 min (conditions 6), MH+=178).

5-Fluoro-quinoline-6-carboxylic acid ethyl ester and 7-fluoro-quinoline-6-carboxylic acid ethyl ester mixture (xii)

To a suspension of 4-amino-2-fluoro-benzoic acid (1 g, 6.38 mmol) in sulfuric acid 75% (15 mL) were added glycerol anhydrous (2.108 mL, 28.72 mmol) and sodium 3-nitrosulfonate (2.93 g, 12.8 mmol). The mixture was stirred at 100° C. for 4 h. It was then cooled down to 60° C. and EtOH was added. The mixture was then stirred at 60° C. for 45 h. The solution was poured into ice-water mixture and then basified with saturated aqueous ammonium hydroxide. It was extracted twice with EtOAc. The organic phases were joined and washed with brine, dried over $Na_2SO_4$ and concentrated. The residue was purified by MPLC eluting with a DCM/MeOH gradient to afford a yellow oil as a mixture (1:1) of 5-fluoro-quinoline-6-carboxylic acid ethyl ester and 7-fluoro-quinoline-6-carboxylic acid ethyl ester ($t_R$ 1.3 min and $t_R$ 1.1 min (conditions 6), MH+=220).

Synthesis of Intermediate M

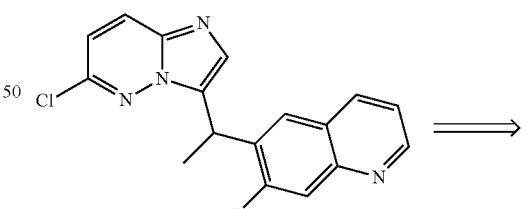

Intermediate M

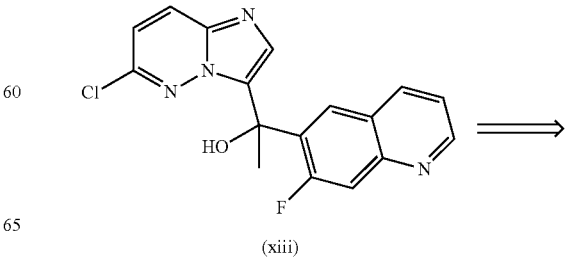

(xiii)

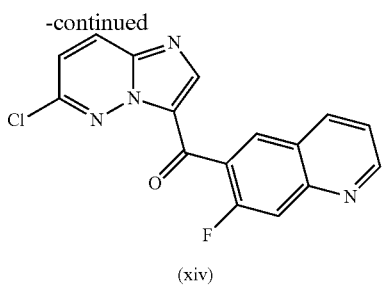

(xiv)

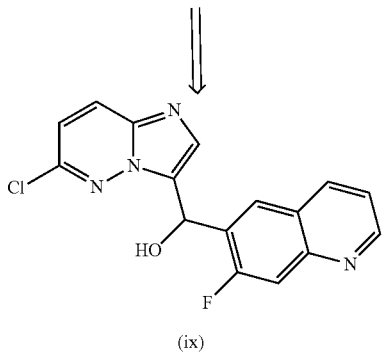

(ix)

Intermediate M (rac)-6-[1-(6-Chloro-imidazo[1,2-b]pyridazin-3-yl)-ethyl]-7-fluoro-quinoline

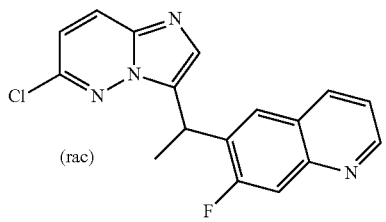 [SMILES: CC(c1cc2cccnc2cc1F)c1cnc2ccc(Cl)nn12]

(rac)

To a solution of (rac)-1-(6-chloro-imidazo[1,2-b]pyridazin-3-yl)-1-(7-fluoro-quinolin-6-yl)-ethanol ((xiii), 200 mg, 0.584 mmol) in acetic acid (3.2 mL) were added iodine (296 mg, 1.167 mmol) and $H_3PO_2$ (0.642 mL of a 50% aqueous solution, 5.84 mmol). The RM was heated at 150° C. for 30 min. After cooling down to RT the acetic acid was evaporated under reduced pressure, water was added and the solution was neutralized with a solution of 10% $NaHCO_3$. The product which precipitated was extracted with DCM, the combined organic phase were dried over $MgSO_4$, filtered, evaporated to dryness and the residue was purified by flash chromatography to afford the title compound as a off white crystalline solid ($t_R$ 4.61 min (conditions 5), MH+=327.2, $^1$H-NMR in DMSO-d6: 8.85 (dd, 1H); 8.28 (dd, 1H); 8.20 (d, 1H); 7.85 (s, 1H); 7.78-7.68 (2H, m); 7.44 (dd, 1H); 7.29 (d, 1H); 4.95 (q, 1H); 1.79 (d, 3H)).

(rac)-1-(6-Chloro-imidazo[1,2-b]pyridazin-3-yl)-1-(7-fluoro-quinolin-6-yl)-ethanol (xiii)

(6-Chloro-imidazo[1,2-b]pyridazin-3-yl)-(7-fluoro-quinolin-6-yl)-methanone ((xiv), 294 mg, 0.9 mmol) was dissolved in anhydrous THF (70 mL) at 40° C. and methylmagnesium bromide in $Et_2O$ (3 M, 0.36 mL) was slowly added and the RM was then allowed to cool down to RT and stirred for 2 h. More methylmagnesium bromide in $Et_2O$ (3 M, 0.5 mL) was added and the RM was stirred for 1 h more. It was then taken into DCM and 10% aqueous $NaHCO_3$ solution and extracted. The organic phase was dried on $MgSO_4$. After evaporation of the solvent the crude was purified by flash chromatography to afford the title compound ($t_R$ 3.74 min (conditions 5), MH+=343, $^1$H-NMR in DMSO-d6: 8.87 (dd, 1H); 8.50 (d, 1H); 8.49 (d, 1H); 8.18 (d, 1H); 7.85 (s, 1H); 7.59 (d, 1H); 7.51 (dd, 1H); 7.23 (d, 1H); 6.33 (s, 1H); 2.13 (s, 3H)).

(6-Chloro-imidazo[1,2-b]pyridazin-3-yl)-(7-fluoro-quinolin-6-yl)-methanone (xiv)

(rac)-(6-Chloro-imidazo[1,2-b]pyridazin-3-yl)-(7-fluoro-quinolin-6-yl)-methanol ((ix), 329 g, 1.0 mmol) was dissolved in acetone (40 mL) and 2-iodoxybenzoic acid (45%, 1.245 g, 2.0 mmol) was added. The RM was heated to reflux for 3 h (suspension). The acetone was then removed under reduced pressure and the residue was taken up with water and 2 M NaOH. The beige suspension was filtered, washed with water and dried overnight under vacuum to afford the title compound as a beige powder ($t_R$ 4.31 min (conditions 5), MH+=327, $^1$H-NMR in DMSO-d6: 9.03 (d, 1H); 8.53 (d, 1H); 8.49-8.41 (m, 2H); 8.39 (s, 1H); 7.90 (d, 1H); 7.74 (d, 1H); 7.62 (dd, 1H)).

Intermediate N 6-(6-Chloro-imidazo[1,2-b]pyridazin-3-ylmethyl)-5-fluoro-quinoline

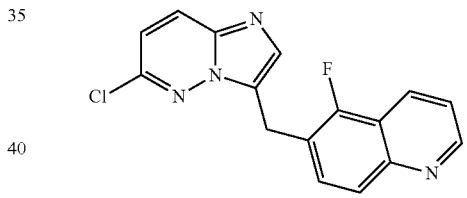

The title compound was obtained from 5-fluoro-quinoline-6-carbaldehyde (Intermediate L) treated with using a procedure analogous to the one used to prepare Intermediate J ($t_R$ 4.96 min (conditions 5), MH+=313).

Intermediate O

6-[1-(6-Chloro-imidazo[1,2-b]pyridazin-3-yl)-ethyl]-5-fluoro-quinoline

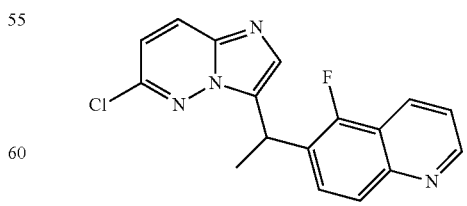

The title compound was obtained from 5-fluoro-quinoline-6-carbaldehyde (Intermediate L) treated with using a procedure analogous to the one used to prepare Intermediate M ($t_R$ 0.9 min (conditions 5), MH+=176).

Synthesis of Intermediates P, Q, R and S

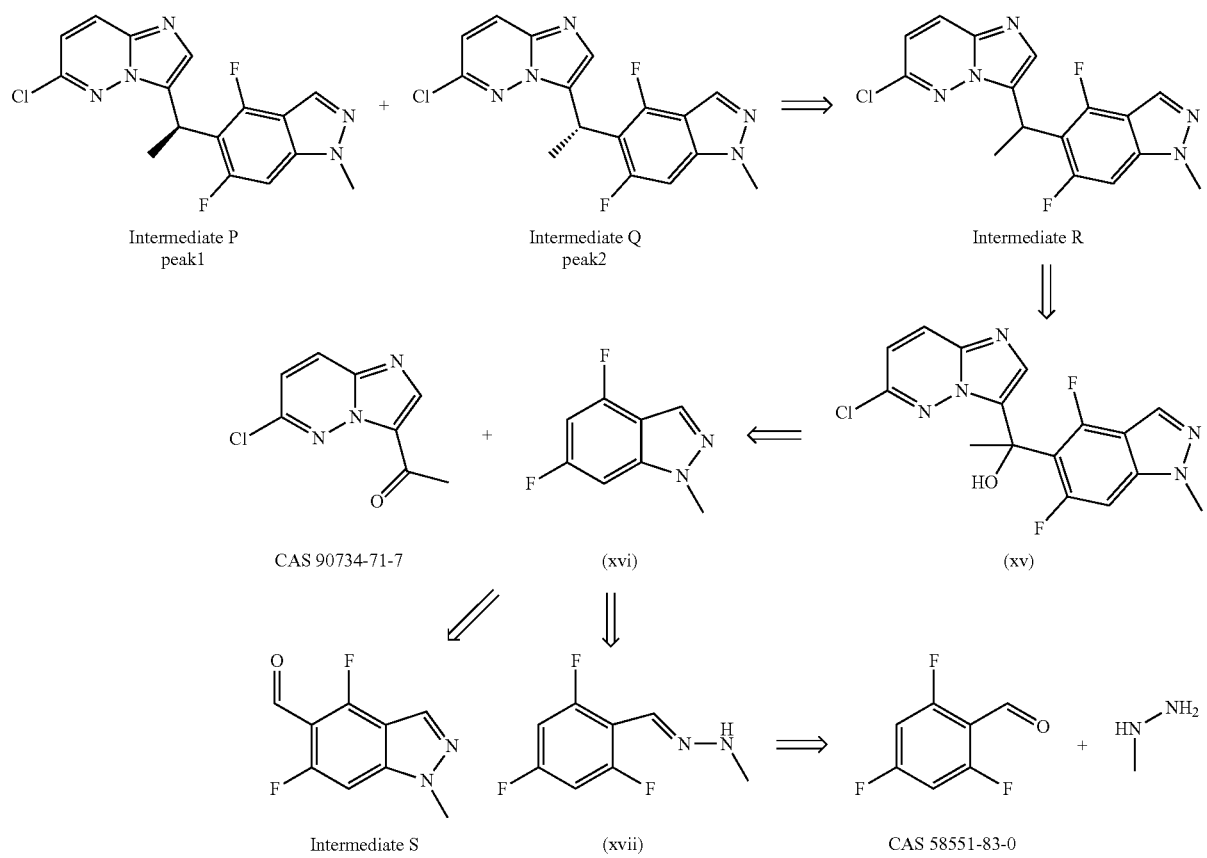

Intermediate P

6-Chloro-3-[(R)-1-(4,6-difluoro-1-methyl-1H-indazol-5-yl)-ethyl]-imidazo[1,2-b]pyridazine

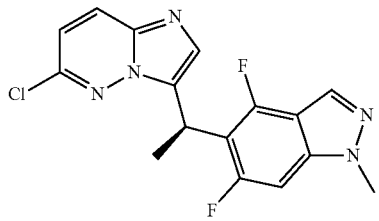 [SMILES: C[C@H](c1c(F)cc2c(cnn2C)c1F)c1cnc2ccc(Cl)nn12]

and

Intermediate Q

6-Chloro-3-[(S)-1-(4,6-difluoro-1-methyl-1H-indazol-5-yl)-ethyl]-imidazo[1,2-b]pyridazine

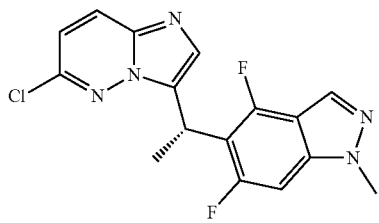 [SMILES: C[C@@H](c1c(F)cc2c(cnn2C)c1F)c1cnc2ccc(Cl)nn12]

The title compounds were obtained from the chiral separation of (rac)-6-chloro-3-(1-(4,6-difluoro-1-methyl-1H-indazol-5-yl)ethyl)imidazo[1,2-b]pyridazine (Intermediate R, 580 mg, 1.67 mmol) using a preparative UPLC (column: AD-H Temperature: 25° C.; mobile phase: Hexane/Ethanol (0.1% DEA)=70/30; flow rate: 1 mL/min as white solids:

Intermediate P (peak 1): ($t_R$ 5.36 min (conditions 5), $t_R$ 8.48 min (conditions 2), $^1$H-NMR in DMSO-d6: 8.16 (d, 1H); 8.11 (s, 1H); 7.85 (s, 1H); 7.43 (d, 1H); 7.25 (d, 1H); 4.94 (m, 1H); 3.97 (s, 3H); 1.81 (d, 3H)).

Intermediate Q (peak 2): ($t_R$ 5.39 min (conditions 5), $t_R$ 10.50 min (conditions 2), $^1$H-NMR in DMSO-d6: 8.16 (d, 1H); 8.11 (s, 1H); 7.85 (s, 1H); 7.43 (d, 1H); 7.25 (d, 1H); 4.94 (m, 1H); 3.97 (s, 3H); 1.81 (d, 3H)).

Intermediate R

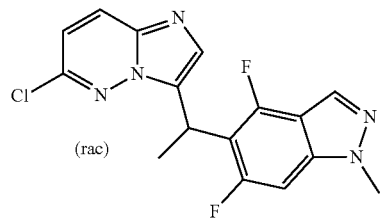 [SMILES: CC(c1c(F)cc2c(cnn2C)c1F)c1cnc2ccc(Cl)nn12]

(rac)-6-chloro-3-(1-(4,6-difluoro-1-methyl-1H-indazol-5-yl)ethyl)imidazo[1,2-b]pyridazine (rac)-1-(6-Chloro-imidazol[1,2-b]pyridazin-3-yl)-1-(4,6-difluoro-1-methyl-1H-indazol-5-yl)ethanol ((xv), 1.1 g, 3.02 mmol was dissolved in acetic acid (16 mL) and introduced in 2 microwave reactor-vials. Iodide (1.15 g×2, 9.07 mmol), followed by H$_3$PO$_2$ 50% (1.18 mL×2, 22.68 mmol) were then added into each vial. Then they were submitted into a hot oil-bath (150° C.) for 10 min. The combined RMs were concentrated in vacuo and the residue was diluted with water, basified by a NaHCO$_3$ 10% solution and extracted with EtOAc (3×). The organics were joined and washed with brine, dried over Na$_2$SO$_4$ and the solvent was removed. The residue was purified by flash chromatography and then crystallized in EtOAc/Pentane to afford the title compound as a yellow solid. (t$_R$ 5.41 min (conditions 5), (t$_R$ 8.59/10.78 min (conditions 2), (MH+=348.1, $^1$H-NMR in DMSO-d6: 8.16 (d, 1H); 8.12 (s, 1H); 7.86 (s, 1H); 7.43 (d, 1H); 7.25 (d, 1H); 4.94 (m, 1H); 3.97 (s, 3H); 1.81 (d, 3H)).

(rac)-1-(6-Chloro-imidazol[1,2-b]pyridazin-3-yl)-1-(4,6-difluoro-1-methyl-1H-indazol-5-yl)-ethanol (xv)

N-BuLi, 6.88 mL, was added dropwise to a solution of 4,6-difluoro-1-methyl-1H-indazole ((xvi), 1.68 g, 10 mmol) in dry THF (50 mL) at −78° C. The solution was stirred at this temperature for 1 h, and then the solution of 1-(6-chloro-imidazo[1,2-b]pyridazin-3-yl)ethanone (CAS 90734-71-7, 1.95 g, 10 mmol) in 50 mL THF was added dropwise at −70/75° C. After stirring additional 3 h at −70/75° C. the RM was quenched with NH$_4$Cl 10%, and at 0° C. diluted with water, and extracted with EtOAc (3×). The organic layers were washed with brine, dried over Na$_2$SO$_4$, filtered and concentrated. The residue was purified by flash chromatography to afford the title compound as a yellow foam (t$_R$ 4.40 min (conditions 5), MH+=364.2, $^1$H-NMR in DMSO-d6: 8.16 (d, 1H); 8.11 (s, 1H); 7.85 (s, 1H); 7.30 (d, 1H); 7.22 (d, 1H); 6.26 (s, 1H); 3.96 (s, 3H); 2.12 (d, 3H)).

4,6-Difluoro-1-methyl-1H-indazole (xvi)

The title compound was synthesized by following a procedure described in *Synthethic Communications*, 1997, 27(7), 1199-1207: N-methyl-N'-[1-(2,4,6-trifluoro-phenyl)methylidene]-hydrazine (xvii) (1.84 g, 9.8 mmol) was fused at 150° C. for 1 h. The residue was purified by flash chromatography to afford the title compound as a yellow crystalline powder (t$_R$ 5.26 min (conditions 5), $^1$H-NMR in DMSO-d6: 8.17 (s, 1H); 7.45 (dt, 1H); 7.00 (td, 1H); 4.00 (s, 3H)).

N-Methyl-N'-[1-(2,4,6-trifluoro-phenyl)-methylidene]-hydrazine[1-methyl-2-(2,4,6-trifluorobenzylidene)hydrazine] (xvii)

2,4,6-Trifluoro-benzaldehyde (4.5 g, 27.3 mmol) was dissolved in Et$_2$O, methyl hydrazine was added (1.43 mL, 27.3 mmol) and the RM was stirred overnight. The solvent was evaporated and the solid residue was suspended in a mixture of pentane and EtOAc to afford after filtration the title compound as a bright yellow crystalline solid (t$_R$ 4.95 min (conditions 5), MH+=198.1).

Intermediate S 4,6-Difluoro-1-methyl-1H-indazole-5-carbaldehyde

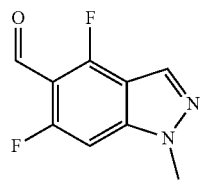

A solution of 4,6-difluoro-1-methyl-1H-indazole ((xvi), 168 mg, 1 mmol) in dry THF (1 mL) was added dropwise to a freshly prepared solution of LDA (n-BuLi 1.25 mL and diisopropylamine 0.285 mL, 2 mmol, in 10 mL THF) at −78° C. The solution was stirred at this temperature for 2 h, and then N-methylformanilide (0.247 mL, 2 mmol) was added dropwise at −70° C. After stirring 2 additional hours at −78° C. the RM was quenched with glacial acetic acid, diluted with water, and extracted twice with EtOAc. The combined organic phases were washed with brine, dried over Na$_2$SO$_4$ and the solvent was removed. The residue was purified by flash chromatography to afford the title compound as a yellowish crystalline powder (t$_R$ 4.49 min (conditions 5), MH+=197, $^1$H-NMR in DMSO-d6: 10.2 (s, 1H); 8.42 (s, 1H); 7.61 (d, 1H); 4.04 (s, 3H)).

Intermediate T

6-Chloro-3-(4,6-difluoro-1-methyl-1H-indazol-5-ylmethyl)-imidazo[1,2-b]pyridazine

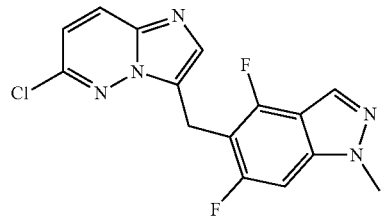 [SMILES: Cn1ncc2c(F)c(Cc3cnc4ccc(Cl)nn34)c(F)cc21]

The title compound was obtained from 4,6-difluoro-1-methyl-1H-indazole-5-carbaldehyde (Intermediate S) treated with using a procedure analogous to the one used to prepare Intermediate J (t$_R$ 5.28 min (conditions 5), MH+=334.1).

Intermediate U (rac)-6-chloro-3-(1-(4,6-difluoro-1-isopropyl-1H-indazol-5-yl)ethyl)imidazo[1,2-b]pyridazine

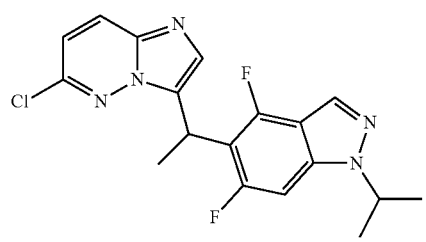 [SMILES: CC(c1c(F)cc2c(cnn2C(C)C)c1F)c1cnc2ccc(Cl)nn12]

The title compound was obtained in analogy to Intermediate R by reacting 4,6-difluoro-1-isopropyl-1H-indazole (xviii) instead of 4,6-difluoro-1-methyl-1H-indazole, (t$_R$ 7.60 min (conditions 5), MH+=376.2, ¹H-NMR in DMSO-d6: 8.16 (d, 1H), 8.14 (s, 1H), 7.86 (s, 1H), 7.50 (d, 1H), 7.26 (d, 1H), 4.93 (m, 2H), 1.81 (d, 3H), 1.42 (m, 6H), 4,6-difluoro-1-isopropyl-1H-indazole (xviii)

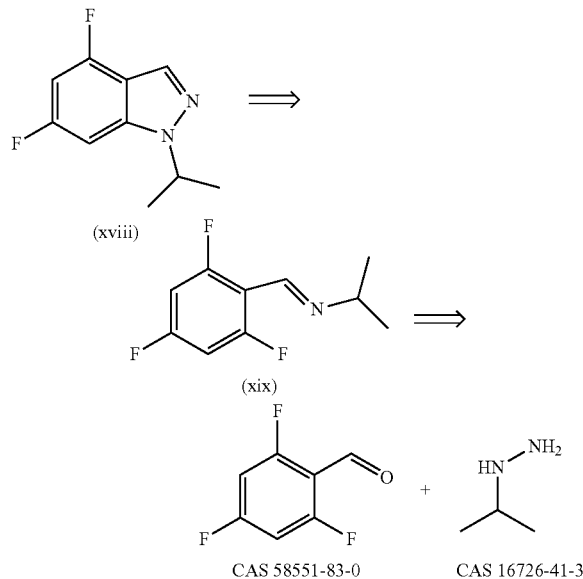

1  N-Isopropyl-N'-[1-(2,4,6-trifluoro-phenyl)-methylidene]-hydrazine ((xix), 865 mg, 4 mmol) was dissolved in 5 mL mesitylene, K₂CO₃ (1.65 g, 12.00 mmol) were added and stirred at 170° C. for 6 h. The RM was cooled, filtered, washed with EtOAc and concentrated. The residue was purified by flash chromatography and afforded the title compound as a yellow oil (t_R 6.86 min (conditions 5), MH−=195, ¹H-NMR in CDCl3: 7.25 (s, 1H); 6.89 (d, 1H), 6.60 (m, 1H), 4.70 (m, 1H), 1.58 (d, 6H).

N-Isopropyl-N'-[1-(2,4,6-trifluoro-phenyl)-methylidene]-hydrazine[1-isopropyl-2-(2,4,6-trifluorobenzylidene)hydrazine] (xix)

2,4,6-trifluorobenzaldehyde (CAS 58551-83-0, 658 mg, 4.11 mmol) was dissolved in Et₂O (11 mL), isopropyl hydrazine-hydrochloride (CAS 16726-41-3, 500 mg, 4.52 mmol), water (1 mL) and NaHCO₃ (380 mg, 4.52 mmol) were added and stirred 3 h at RT. An emulsion was formed Et₂O was added and washed with brine, dried over MgSO4 and the solvent was removed to give the title compound as a light yellow liquid (898 mg, t_R 5.81 min (conditions 5), MH+=217.2).

EXAMPLE 1

(rac)-4-{3-[1-(5,7-Difluoro-quinolin-6-yl)-ethyl]-imidazo[1,2-b]pyridazin-6-yl}-1-methyl-piperazin-2-one

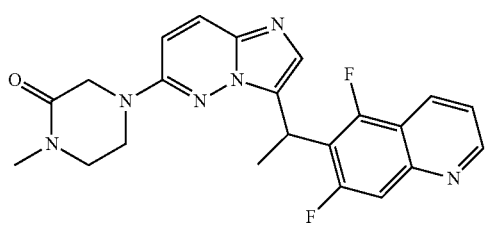 [SMILES: CC(c1c(F)cc2ncccc2c1F)c1cnc2ccc(N3CCN(C)C(=O)C3)nn12]

(rac)-6-[1-(6-Chloro-imidazo[1,2-b]pyridazin-3-yl)-ethyl]-5,7-difluoro-quinoline (Intermediate C, 50 mg, 0.145 mmol), KF (84 mg, 1.45 mmol) and 1-methylpiperazine-2-one hydrochloride (65 mg, 0.435 mmol) were suspended in NMP (0.483 mL). The RM was stirred at 180° C. for 5 h. The mixture was filtered and the obtained filtrate was purified by reverse phase chromatography (water+0.1% TFA/acetonitrile+0.1% TFA). The collected fractions were concentrated and the residue was dissolved in MeOH, passed through an SPE cartridge of PL-HCO3 MP. The filtrate was concentrated to afford the title compound as a brownish oil (t_R 3.19 min (conditions 1), MH+=423).

EXAMPLE 2

4-{3-[(S)-1-(5,7-Difluoro-quinolin-6-yl)-ethyl]-imidazo[1,2-b]pyridazin-6-yl}-1-methyl-piperazin-2-one

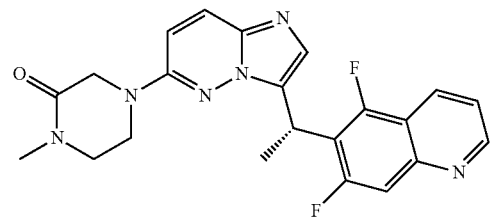 [SMILES: C[C@@H](c1c(F)cc2ncccc2c1F)c1cnc2ccc(N3CCN(C)C(=O)C3)nn12]

6-[(S)-1-(6-chloro-imidazo[1,2-b]pyridazin-3-yl)-ethyl]-5,7-difluoro-quinoline (Intermediate B, 3.0 g, 8.58 mmol), KF (2.52 g, 42.9 mmol), 1-methylpiperazine-2-one hydrochloride (3.88 g, 25.7 mmol), N-ethyldiisopropylamine (5.99 mL, 35 mmol) were suspended in NMP (60 mL). The RM was stirred at 180° C. for 8.5 h. The mixture was diluted with EtOAc and washed with 1M Na₂CO₃ (1×) and water (2×). The aqueous was further extracted with EtOAc (2×). The combined organic layers were dried over Na₂SO₄, filtered and concentrated. The residue was purified by flash chromatography and then crystallized in EtOAc to afford the title compound as a white solid (t_R 3.19 min (conditions 1), (t_R 8.84 min (conditions 2), MH+=423.2, ¹H-NMR in DMSO-d6: 8.94 (d, 1H); 8.45 (d, 1H); 7.84 (d, 1H); 7.63 (s, 1H); 7.59 (m, 2H); 7.08 (d, 1H); 4.98 (m, 1H); 4.02 (d, 1H); 3.73 (d, 1H); 3.60 (m, 2H); 3.31 (m, 1H); 3.25 (m, 1H); 2.80 (s, 3H); 1.88 (d, 3H)).

EXAMPLE 3

(rac)-4-{3-[1-(5,7-Difluoro-quinolin-6-yl)-ethyl]-imidazo[1,2-b]pyridazin-6-yl}-piperazin-2-one

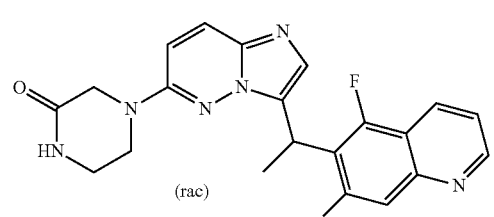

(rac)-6-[1-(6-Chloro-imidazo[1,2-b]pyridazin-3-yl)-ethyl]-5,7-difluoro-quinoline (Intermediate C, 6.40 g, 18.21 mmol), KF (5.34 g, 91.0 mmol), piperazin-2-one (5.64 g, 54.6 mmol) were suspended in NMP (60 mL). The RM was stirred at 180° C. for 7 h. The mixture was diluted with EtOAc and washed with 1M Na$_2$CO$_3$ (1×) and water (2×). The aqueous was further extracted with EtOAc (2×). The combined organic layers were dried over Na$_2$SO$_4$, filtered and concentrated. The residue was purified by flash chromatography and then crystallized in DCM to afford the title compound as a beige solid (t$_R$ 3.02 min (conditions 1), (t$_R$ 7.58/10.54 min (conditions 3), MH+=409.1, $^1$H-NMR in DMSO-d6: 8.94 (d, 1H); 8.45 (d, 1H); 8.05 (s, 1H); 7.83 (d, 1H); 7.63 (m, 1H); 7.62 (s, 1H); 7.59 (m, 1H); 7.05 (d, 1H); 4.99 (m, 1H); 3.97 (d, 1H); 3.69 (d, 1H); 3.51 (m, 2H); 3.19 (m, 1H); 3.12 (m, 1H); 1.88 (d, 3H)).

EXAMPLE 4

4-{3-[(R)-1-(5,7-Difluoro-quinolin-6-yl)-ethyl]-imidazo[1,2-b]pyridazin-6-yl}-piperazin-2-one

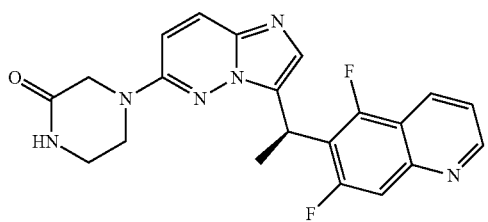 [SMILES: C[C@H](c1c(F)cc2ncccc2c1F)c1cnc2ccc(N3CCNC(=O)C3)nn12]

The title compound was obtained from the chiral separation of compound of Example 3 using a preparative UPLC (Column: Chiracel OJ 10×50 cm Mobile phase: heptane-ethanol 60:40 Flow rate: 110 mL/min Detection: UV 210 nm. The first eluted peak (t$_R$ 85 min) afforded the title compound after crystallization in EtOAc as a slightly beige solid (t$_R$ 3.00 min (conditions 1), (t$_R$ 7.58 min (conditions 3), MH+=409.1, $^1$H-NMR in DMSO-d6: 8.94 (d, 1H); 8.45 (d, 1H); 8.05 (s, 1H); 7.83 (d, 1H); 7.63 (m, 1H); 7.62 (s, 1H); 7.59 (m, 1H); 7.05 (d, 1H); 4.99 (m, 1H); 3.97 (d, 1H); 3.69 (d, 1H); 3.51 (m, 2H); 3.19 (m, 1H); 3.12 (m, 1H); 1.88 (d, 3H)).

EXAMPLE 5

4-{3-[(S)-1-(5,7-Difluoro-quinolin-6-yl)-ethyl]-imidazo[1,2-b]pyridazin-6-yl}-piperazin-2-one

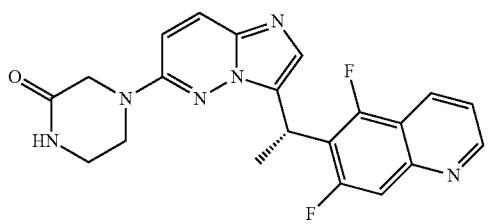 [SMILES: C[C@@H](c1c(F)cc2ncccc2c1F)c1cnc2ccc(N3CCNC(=O)C3)nn12]

The title compound was obtained from the chiral separation of compound of Example 3 using a preparative UPLC (Column: Chiracel OJ 10×50 cm Mobile phase: heptane-ethanol 60:40 Flow rate: 110 mL/min Detection: UV 210 nm. The second eluted peak (t$_R$ 130 min) afforded the title compound after crystallization in EtOAc as a slightly beige solid (t$_R$ 3.00 min (conditions 1), (t$_R$ 10.54 min (conditions 3), MH+=409.1, $^1$H-NMR in DMSO-d6: 8.94 (d, 1H); 8.45 (d, 1H); 8.05 (s, 1H); 7.83 (d, 1H); 7.63 (m, 1H); 7.62 (s, 1H); 7.59 (m, 1H); 7.05 (d, 1H); 4.99 (m, 1H); 3.97 (d, 1H); 3.69 (d, 1H); 3.51 (m, 2H); 3.19 (m, 1H); 3.12 (m, 1H); 1.88 (d, 3H)).

EXAMPLE 6

(rac)-5,7-Difluoro-6-[1-(6-piperazin-1-yl-imidazo[1,2-b]pyridazin-3-yl)-ethyl]-quinoline

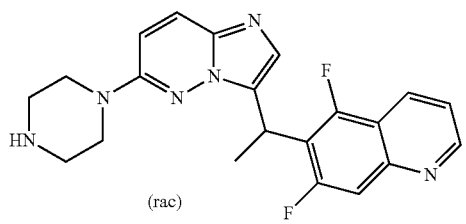 [SMILES: CC(c1c(F)cc2ncccc2c1F)c1cnc2ccc(N3CCNCC3)nn12]

(rac)-6-[1-(6-Chloro-imidazo[1,2-b]pyridazin-3-yl)-ethyl]-5,7-difluoro-quinoline (Intermediate C, 200 mg, 0.569 mmol), KF (371 mg, 6.26 mmol) and piperazine (490 mg, 5.69 mmol) were suspended in NMP (2.85 mL). The RM was stirred at 170° C. for 1 h. The mixture was diluted with EtOAc and washed with 1M Na$_2$CO$_3$ (1×) and water (2×). The aqueous was further extracted with EtOAc (2×). The combined organic layers were dried over Na$_2$SO$_4$, filtered and concentrated. The residue was purified by flash chromatography and afford the title compound as a yellow foam (t$_R$ 2.78 min (conditions 1), MH+=395).

EXAMPLE 7

5,7-Difluoro-6-[(S)-1-(6-piperazin-1-yl-imidazo[1,2-b]pyridazin-3-yl)-ethyl]-quinoline

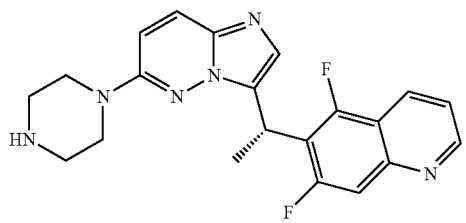 [SMILES: C[C@@H](c1c(F)cc2ncccc2c1F)c1cnc2ccc(N3CCNCC3)nn12]

6-[(S)-1-(6-chloro-imidazo[1,2-b]pyridazin-3-yl)-ethyl]-5,7-difluoro-quinoline (Intermediate B, 200 mg, 0.569 mmol), KF (371 mg, 6.26 mmol) and piperazine (490 mg, 5.69 mmol) were suspended in NMP (2.85 mL). The RM was stirred at 170° C. for 1 h. The mixture was diluted with EtOAc and washed with 1M Na$_2$CO$_3$ (1×) and water (2×). The aqueous was further extracted with EtOAc (2×). The combined organic layers were dried over Na$_2$SO$_4$, filtered and concentrated. The residue was purified by flash chromatography and afforded the title compound as a yellow foam (t$_R$ 2.78 min (conditions 1), MH+=395, $^1$H-NMR in DMSO-d6: 8.95 (d, 1H); 8.45 (d, 1H); 7.77 (d, 1H); 7.61 (d, 1H); 7.59 (s, 1H); 7.58 (m, 1H); 7.02 (d, 1H); 4.95 (m, 1H); 3.23 (m, 2H); 3.07 (m, 2H); 2.62 (m, 2H); 2.56 (m, 2H); 1.87 (d, 3H)).

EXAMPLE 8

(rac)-5,7-Difluoro-6-{1-[6-(4-methyl-piperazin-1-yl)-imidazo[1,2-b]pyridazin-3-yl]-ethyl}-quinoline

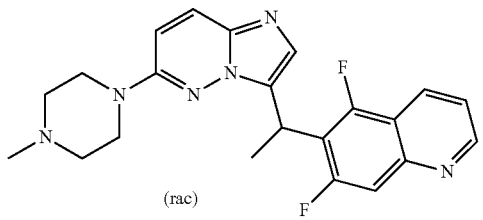 [SMILES: CC(c1c(F)cc2ncccc2c1F)c1cnc2ccc(N3CCN(C)CC3)nn12]

(rac)-6-[1-(6-chloro-imidazo[1,2-b]pyridazin-3-yl)-ethyl]-5,7-difluoro-quinoline (Intermediate C, 69 mg, 0.20 mmol), KF (58 mg, 1.0 mmol) and N-methyl-piperazine (60 mg, 0.60 mmol) were suspended in NMP (1.0 mL). The RM was stirred at 170° C. for 2 h. The mixture was diluted with EtOAc and washed with 1M $Na_2CO_3$ (1×) and water (2×). The aqueous was further extracted with EtOAc (2×). The combined organic layers were dried over $Na_2SO_4$, filtered and concentrated. The residue was purified by flash chromatography and afforded the title compound as a yellow foam ($t_R$ 2.83 min (conditions 1), MH+=409.1).

EXAMPLE 9

5,7-Difluoro-6-{(S)-1-[6-(4-methyl-piperazin-1-yl)-imidazo[1,2-b]pyridazin-3-yl]-ethyl}-quinoline

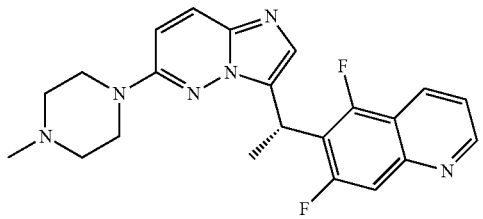 [SMILES: C[C@@H](c1c(F)cc2ncccc2c1F)c1cnc2ccc(N3CCN(C)CC3)nn12]

The title compound was prepared in analogy to Example 8 using 6-[(S)-1-(6-chloro-imidazo[1,2-b]pyridazin-3-yl)ethyl]-5,7-difluoro-quinoline (Intermediate B) instead of (rac)-6-[1-(6-chloro-imidazo[1,2-b]pyridazin-3-yl)-ethyl]-5,7-difluoro-quinoline ($t_R$ 2.85 min (conditions 1), MH+=409.1, $^1$H-NMR in DMSO-d6: 8.94 (d, 1H); 8.45 (d, 1H); 7.78 (d, 1H); 7.63 (d, 1H); 7.60 (s, 1H); 7.59 (d, 1H); 7.04 (d, 1H); 4.96 (m, 1H); 3.15-3.35 (m, 4H); 2.22-2.11 (m, 4H); 2.06 (s, 3H); 1.87 (d, 3H)).

EXAMPLE 10

(rac)-1-(4-{3-[1-(5,7-Difluoro-quinolin-6-yl)-ethyl]-imidazo[1,2-b]pyridazin-6-yl}-piperazin-1-yl)ethanone

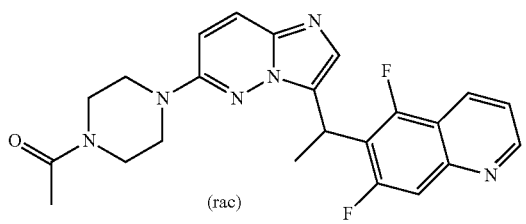 [SMILES: CC(=O)N1CCN(c2ccc3ncc(C(C)c4c(F)cc5ncccc5c4F)n3n2)CC1]

(rac)-5,7-Difluoro-6-[1-(6-piperazin-1-yl-imidazo[1,2-b]pyridazin-3-yl)-ethyl]-quinoline (Example 6, 50 mg, 0.127 mmol) was dissolved in pyridine (1.27 mL) and acetyl chloride (0.014 mL, 0.190 mmol) was added. The RM was stirred at RT for 0.5 h. The mixture was concentrated and the residue was purified by flash chromatography and afforded the title compound as a beige foam ($t_R$ 3.36 min (conditions 1), MH+ 437).

EXAMPLE 11

1-(4-{3-[(S)-1-(5,7-Difluoro-quinolin-6-yl)-ethyl]-imidazo[1,2-b]pyridazin-6-yl}-piperazin-1-yl)ethanone

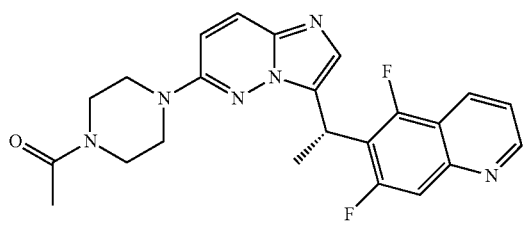 [SMILES: CC(=O)N1CCN(c2ccc3ncc([C@@H](C)c4c(F)cc5ncccc5c4F)n3n2)CC1]

The title compound was prepared in analogy to Example 10 using 5,7-difluoro-6-[(S)-1-(6-piperazin-1-yl-imidazo[1,2-b]pyridazin-3-yl)-ethyl]-quinoline (Example 7) instead of (rac)-5,7-difluoro-6-[1-(6-piperazin-1-yl-imidazo[1,2-b]pyridazin-3-yl)-ethyl]-quinoline ($t_R$ 3.39 min (conditions 1), ($t_R$ 8.38 min (conditions 2), MH+=437, $^1$H-NMR in DMSO-d6: 8.94 (d, 1H); 8.49 (d, 1H); 7.82 (d, 1H); 7.65 (d, 1H); 7.62 (s, 1H); 7.60 (m, 1H); 7.07 (d, 1H); 4.98 (m, 1H); 3.15-3.40 (m, 8H); 1.98 (s, 3H); 1.88 (d, 3H)).

EXAMPLE 12

(rac)-4-{3-[1-(5,7-Difluoro-quinolin-6-yl)-ethyl]-imidazo[1,2-b]pyridazin-6-yl}-piperazine-1-carbaldehyde

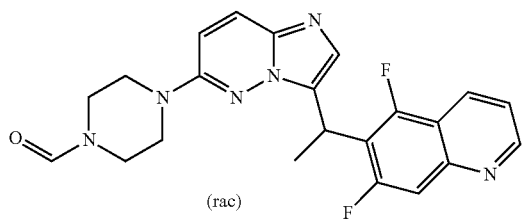 [SMILES: CC(c1c(F)cc2ncccc2c1F)c1cnc2ccc(N3CCN(C=O)CC3)nn12]

(rac)-5,7-Difluoro-6-[1-(6-piperazin-1-yl-imidazo[1,2-b]pyridazin-3-yl)-ethyl]-quinoline (Example 6, 50 mg, 0.127 mmol) and 4-nitrophenyl formate (29.7 mg, 0.177 mmol) were dissolved in DCM (1.27 mL) and triethylamine (0.021 mL, 0.152 mmol) was added. The RM was stirred at RT for 0.5 h. The mixture was concentrated and the residue was purified by flash chromatography and afforded the title compound as a white foam ($t_R$ 3.25 min (conditions 1), MH+=423).

EXAMPLE 13

4-{3-[(S)-1-(5,7-Difluoro-quinolin-6-yl)-ethyl]-imidazo[1,2-b]pyridazin-6-yl}-piperazine-1-carbaldehyde

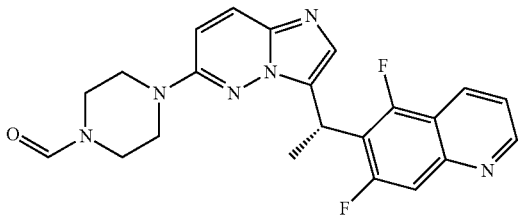 [SMILES: C[C@@H](c1c(F)cc2ncccc2c1F)c1cnc2ccc(N3CCN(C=O)CC3)nn12]

The title compound was prepared in analogy to Example 12 using 5,7-difluoro-6-[(S)-1-(6-piperazin-1-yl-imidazo[1,2-b]pyridazin-3-yl)-ethyl]-quinoline (Example 7) instead of (rac)-5,7-difluoro-6-[1-(6-piperazin-1-yl-imidazo[1,2-b]pyridazin-3-yl)-ethyl]-quinoline ($t_R$ 3.28 min (conditions 1), ($t_R$ 9.84 min (conditions 2), MH+=423, $^1$H-NMR in DMSO-d6: 8.95 (d, 1H); 8.47 (d, 1H); 8.02 (s, 1H); 7.82 (d, 1H); 7.65 (d, 1H); 7.63 (s, 1H); 7.60 (m, 1H); 7.08 (d, 1H); 4.98 (m, 1H); 3.15-3.40 (m, 8H); 1.88 (d, 3H)).

EXAMPLE 14

(rac)-4-{3-[1-(5,7-Difluoro-quinolin-6-yl)-ethyl]-imidazo[1,2-b]pyridazin-6-yl}-piperazine-1-carboxylic acid methyl ester

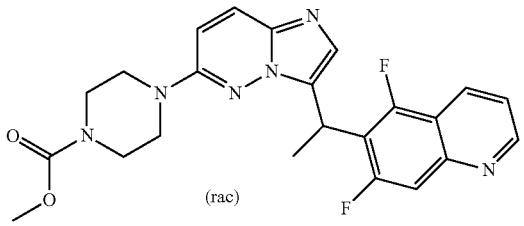 [SMILES: COC(=O)N1CCN(c2ccc3ncc(C(C)c4c(F)cc5ncccc5c4F)n3n2)CC1]

(rac)-5,7-Difluoro-6-[1-(6-piperazin-1-yl-imidazo[1,2-b]pyridazin-3-yl)-ethyl]-quinoline (Example 6, 35 mg, 0.089 mmol) was dissolved in pyridine (0.89 mL) and methyl chloroformate (0.010 mL, 0.133 mmol) was added. The RM was stirred at RT for 1.5 h. The mixture was concentrated and the residue was purified by flash chromatography and afforded the title compound as a beige foam ($t_R$ 3.70 min (conditions 1), MH+=453).

EXAMPLE 15

(rac)-4-{3-[1-(5,7-Difluoro-quinolin-6-yl)-ethyl]-imidazo[1,2-b]pyridazin-6-yl}-piperazine-1-carboxylic acid amide

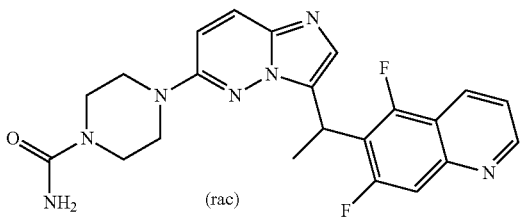 [SMILES: CC(c1c(F)cc2ncccc2c1F)c1cnc2ccc(N3CCN(C(N)=O)CC3)nn12]

The title compound was prepared in analogy to Example 3 using (rac)-6-[1-(6-chloro-imidazo[1,2-b]pyridazin-3-yl)-ethyl]-5,7-difluoro-quinoline (Intermediate C) and piperazine-1-carboxamide instead of piperazin-2-one ($t_R$ 3.16 min (conditions 1), MH+=438, $^1$H-NMR in DMSO-d6: 8.95 (d, 1H); 8.46 (d, 1H); 7.80 (d, 1H); 7.65 (d, 1H); 7.61 (s, 1H); 7.60 (m, 1H); 7.08 (d, 1H); 6.07 (s, 2H); 4.98 (m, 1H); 3.15-3.40 (m, 8H); 1.88 (d, 3H)).

EXAMPLE 16

4-{3-[(S)-1-(5,7-Difluoro-quinolin-6-yl)-ethyl]-imidazo[1,2-b]pyridazin-6-yl}-piperazine-1-carboxylic acid amide

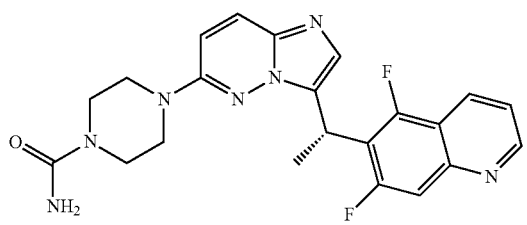 [SMILES: C[C@@H](c1c(F)cc2ncccc2c1F)c1cnc2ccc(N3CCN(C(N)=O)CC3)nn12]

The title compound was prepared in analogy to Example 3 using 6-[(S)-1-(6-chloro-imidazo[1,2-b]pyridazin-3-yl)-ethyl]-5,7-difluoro-quinoline (Intermediate B) and piperazine-1-carboxamide instead of piperazin-2-one ($t_R$ 3.17 min (conditions 1), MH+=438, $^1$H-NMR in DMSO-d6: 8.95 (d, 1H); 8.46 (d, 1H); 7.80 (d, 1H); 7.65 (d, 1H); 7.61 (s, 1H); 7.60 (m, 1H); 7.08 (d, 1H); 6.07 (s, 2H); 4.98 (m, 1H); 3.15-3.40 (m, 8H); 1.88 (d, 3H)).

EXAMPLE 17

(rac)-1-(4-{3-[1-(5,7-Difluoro-quinolin-6-yl)-ethyl]-imidazo[1,2-b]pyridazin-6-yl}-piperazin-1-yl)-2,2,2-trifluoro-ethanone

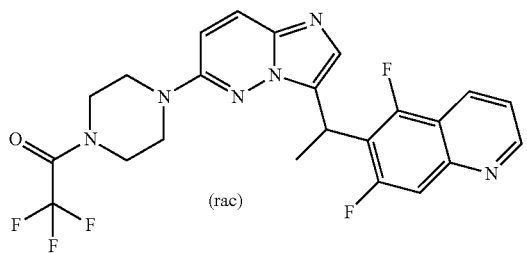 [SMILES: CC(c1c(F)cc2ncccc2c1F)c1cnc2ccc(N3CCN(C(=O)C(F)(F)F)CC3)nn12]

(rac)-5,7-Difluoro-6-[1-(6-piperazin-1-yl-imidazo[1,2-b]pyridazin-3-yl)-ethyl]-quinoline (Example 6, 50 mg, 0.127 mmol) and triethylamine (0.141 mL, 1.014 mmol) were dissolved in THF (1.27 mL) and trifluoroacetic anhydride (0.070 mL, 0.507 mmol) was added. The RM was stirred at RT for 0.75 h. The mixture was diluted with EtOAc and washed with 1M NaHCO$_3$ (1×) and brine (1×). The aqueous was further extracted with EtOAc (1×). The combined organic layer was dried over Na$_2$SO$_4$, filtered and concentrated. The residue was purified by flash chromatography and afforded the title compound as a beige foam ($t_R$ 4.00 min (conditions 1), MH+=491, $^1$H-NMR in DMSO-d6: 8.95 (d, 1H); 8.48 (d, 1H); 7.86 (d, 1H); 7.66 (d, 1H); 7.64 (s, 1H); 7.60 (m, 1H); 7.06 (d, 1H); 4.99 (m, 1H); 3.25-3.55 (m, 8H); 1.88 (d, 3H)).

EXAMPLE 18

(rac)-4-{3-[1-(5,7-Difluoro-quinolin-6-yl)-ethyl]-imidazo[1,2-b]pyridazin-6-yl}-3-methyl-piperazin-2-one

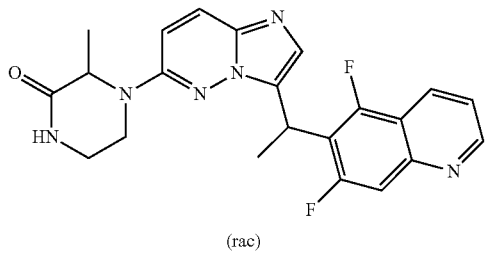 [SMILES: CC(c1c(F)cc2ncccc2c1F)c1cnc2ccc(N3CCNC(=O)C3C)nn12]

(rac)

(rac)-6-[1-(6-Chloro-imidazo[1,2-b]pyridazin-3-yl)-ethyl]-5,7-difluoro-quinoline (Intermediate C, 55 mg, 0.160 mmol), KF (46.3 mg, 0.798 mmol), 3-methylpiperazine (54.6 mg, 0.479 mmol) were suspended in NMP (532 µL). The RM was stirred at 180° C. for 16 h. The mixture was purified by preparative UPLC with acetonitrile and water (+0.1% TFA) The fractions were collected and acetonitrile was removed. It was taken up with EtOAc/MeOH (9/1) and washed with 5% Na₂CO₃ solution and brine. The organic layer was dried over sodium sulfate and the solvent was removed. A brown solid was obtained ($t_R$ 0.9 min (conditions 4), MH+=423)

EXAMPLE 19

(rac)-4-{3-[1-(5,7-Difluoro-quinolin-6-yl)-ethyl]-imidazo[1,2-b]pyridazin-6-yl}-[1,4]diazepan-5-one

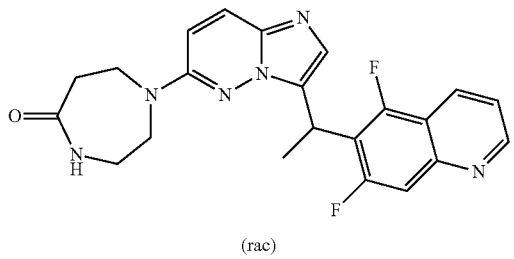 [SMILES: CC(c1c(F)cc2ncccc2c1F)c1cnc2ccc(N3CCNC(=O)CC3)nn12]

(rac)

The title compound was prepared in analogy to Example 18 using 1,4diazepan-5-one instead of 3-methyl piperazin-2-one over 5 h at 180° C. ($t_R$ 0.9 min (conditions 4), MH+=423)

EXAMPLE 20

(rac)-4-{3-[1-(5,7-Difluoro-quinolin-6-yl)-ethyl]-imidazo[1,2-b]pyridazin-6-yl}-1-cyclopentylpiperazin-2-one

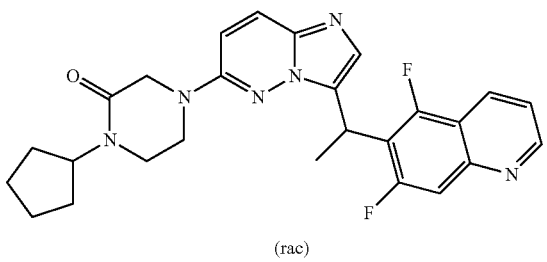 [SMILES: CC(c1c(F)cc2ncccc2c1F)c1cnc2ccc(N3CCN(C4CCCC4)C(=O)C3)nn12]

(rac)

(rac)-6-[1-(6-Chloro-imidazo[1,2-b]pyridazin-3-yl)-ethyl]-5,7-difluoro-quinoline (Intermediate C, 50 mg, 0.145 mmol), KF (84 mg, 1.450 mmol), 1-cyclopentylpiperazin-2-one TFA salt (129 mg, 0.435 mmol) were suspended in NMP (483 µL). The RM was stirred at 180° C. for 5 h. The mixture was purified by preparative UPLC with acetonitrile and water (+0.1% TFA) The fractions were collected and acetonitrile was removed. It was taken up with MeOH and passed through an SPE cartridge of PL-HCO3 MP from polymer lab. The solvent was removed and a brown solid was obtained ($t_R$ 1.1 min (conditions 4), MH+=477)

EXAMPLE 21

(rac)-4-{3-[1-(5,7-Difluoro-quinolin-6-yl)-ethyl]-imidazo[1,2-b]pyridazin-6-yl}-1,3-dimethylpiperazin-2-one

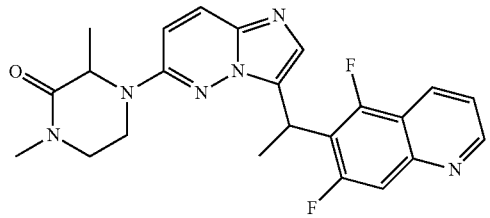 [SMILES: CC(c1c(F)cc2ncccc2c1F)c1cnc2ccc(N3CCN(C)C(=O)C3C)nn12]

(rac)-6-[1-(6-Chloro-imidazo[1,2-b]pyridazin-3-yl)-ethyl]-5,7-difluoro-quinoline (Intermediate C, 50 mg, 0.145 mmol), KF (84 mg, 1.450 mmol), 1,3-dimethylpiperazin-2-one HCl salt (75 mg, 0.435 mmol) were suspended in NMP (483 µL). The RM was stirred at 180° C. for 20 h. The mixture was purified by preparative UPLC with acetonitrile and water (+0.1% TFA) The fractions were collected and acetonitrile was removed. It was taken up with MeOH and passed through an SPE cartridge of PL-HCO3 MP from polymer lab. The solvent was removed and a brown solid was obtained ($t_R$ 0.9 min (conditions 4), MH+=437).

EXAMPLE 22

(rac)-4-{3-[1-(5,7-Difluoro-quinolin-6-yl)-ethyl]-imidazo[1,2-b]pyridazin-6-yl}-1-phenylpiperazin-2-one

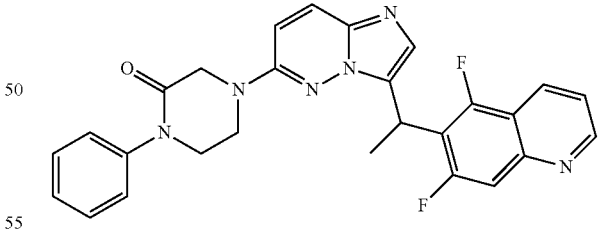

(rac)-6-[1-(6-Chloro-imidazo[1,2-b]pyridazin-3-yl)-ethyl]-5,7-difluoro-quinoline (Intermediate C, 50 mg, 0.145 mmol), KF (84 mg, 1.450 mmol), 1-phenylpiperazin-2-one TFA salt (133 mg, 0.435 mmol) were suspended in NMP (483 µL). The RM was stirred at 180° C. for 5 h. The mixture was purified by preparative UPLC with acetonitrile and water (+0.1% TFA) The fractions were collected and acetonitrile was removed. It was taken up with MeOH and passed through an SPE cartridge of PL-HCO3 MP from polymer lab. The solvent was removed and a brown solid was obtained ($t_R$ 1.0 min (conditions 4), MH+=485).

EXAMPLE 23

(rac)-4-{3-[1-(5,7-Difluoro-quinolin-6-yl)-ethyl]-imidazo[1,2-b]pyridazin-6-yl}-5-methylpiperazin-2-one

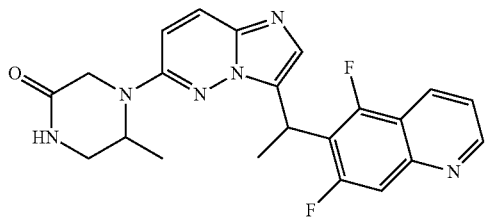 [SMILES: CC(c1c(F)cc2ncccc2c1F)c1cnc2ccc(N3CC(=O)NCC3C)nn12]

(rac)-6-[1-(6-Chloro-imidazo[1,2-b]pyridazin-3-yl)-ethyl]-5,7-difluoro-quinoline (Intermediate C, 50 mg, 0.145 mmol), KF (84 mg, 1.450 mmol), 5-methylpiperazin-2-one hydrochloride salt (65.5 mg, 0.435 mmol) were suspended in NMP (483 µL). The RM was stirred at 180° C. for 16 h. The mixture was purified by preparative UPLC with acetonitrile and water (+0.1% TFA) The fractions were collected and acetonitrile was removed. It was taken up with MeOH and passed through an SPE cartridge of PL-HCO3 MP from polymer lab. The solvent was removed and a brown solid was obtained ($t_R$ 0.9 min (conditions 4), MH+=423).

EXAMPLE 24

(rac)-4-{3-[1-(5,7-Difluoro-quinolin-6-yl)-ethyl]-imidazo[1,2-b]pyridazin-6-yl}-6-methylpiperazin-2-one

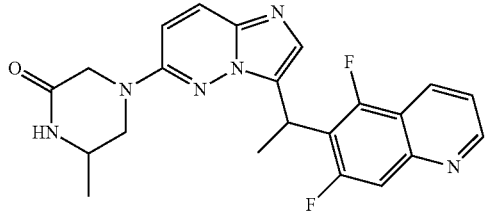 [SMILES: CC1CN(c2ccc3ncc(C(C)c4c(F)cc5ncccc5c4F)n3n2)CC(=O)N1]

(rac)-6-[1-(6-Chloro-imidazo[1,2-b]pyridazin-3-yl)-ethyl]-5,7-difluoro-quinoline (Intermediate C, 50 mg, 0.145 mmol), KF (42.1 mg, 0.725 mmol), 6-methylpiperazin-2-one (49.7 mg, 0.435 mmol) were suspended in NMP (483 µL). The RM was stirred at 180° C. for 16 h. The mixture was purified by preparative UPLC with acetonitrile and water (+0.1% TFA) The fractions were collected and acetonitrile was removed. It was taken up with MeOH and passed through an SPE cartridge of PL-HCO3 MP from polymer lab. The solvent was removed and a brown solid was obtained ($t_R$ 0.9 min (conditions 4), MH+=423).

EXAMPLE 25

(rac)-4-{3-[1-(5,7-Difluoro-quinolin-6-yl)-ethyl]-imidazo[1,2-b]pyridazin-6-yl}-1-(pyridin-2-yl)piperazin-2-one

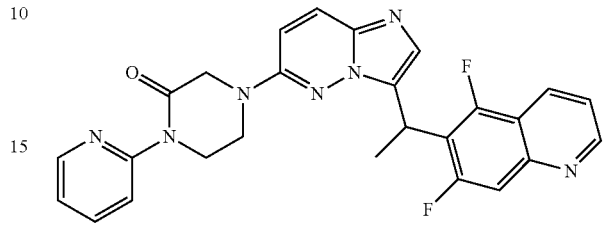

(rac)-6-[1-(6-Chloro-imidazo[1,2-b]pyridazin-3-yl)-ethyl]-5,7-difluoro-quinoline (Intermediate C, 50 mg, 0.145 mmol), KF (84 mg, 1.450 mmol), 1-(pyridin-2-yl)piperazin-2-one dihydrochloride salt (109 mg, 0.435 mmol) were suspended in NMP (483 µL). The RM was stirred at 180° C. for 16 h. The mixture was purified by preparative UPLC with acetonitrile and water (+0.1% TFA) The fractions were collected and acetonitrile was removed. It was taken up with MeOH and passed through an SPE cartridge of PL-HCO3 MP from polymer lab. The solvent was removed and a brown solid was obtained ($t_R$ 1.0 min (conditions 4), MH+=486).

EXAMPLE 26

4-{3-[(S)-1-(6-Fluoro-1-methyl-1H-indazol-5-yl)-ethyl]-imidazo[1,2-b]pyridazin-6-yl}-1-methyl-piperazin-2-one

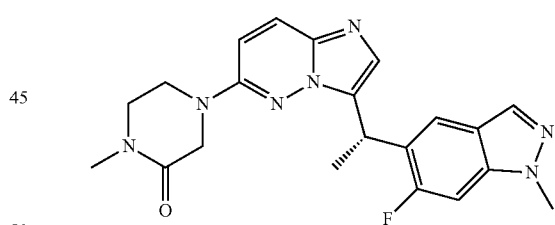

6-Chloro-3-[(S)-1-(6-fluoro-1-methyl-1H-indazol-5-yl)-ethyl]-imidazo[1,2-b]pyridazine (Intermediate E, 50.0 mg, 0.152 mmol), KF (26.4 mg, 0.455 mmol) and 1-methylperazine-2-one hydrochloride (51.9 mg, 0.455 mmol) were suspended in NMP (1 mL). The RM was stirred at 180° C. for 5 h. The mixture was diluted with EtOAc and washed with NaHCO3 10% (2×) and water (4×). The combined organic layers were dried over Na2SO4, filtered and concentrated. The residue was purified by flash chromatography and afforded the title compound as a light brown foam ($t_R$ 3.66 min (conditions 5), ($t_R$ 12.22 min (conditions 2), MH+=408.2, $^1$H-NMR in DMSO-d6: 7.92 (s, 1H); 7.83 (d, 1H); 7.49 (m, 3H); 7.11 (d, 1H); 4.78 (m, 1H); 4.00 (d, 1H); 3.95 (s, 3H); 3.86 (d, 1H); 3.67 (m, 2H); 3.30 (m, 2H); 2.80 (s, 3H); 1.71 (d, 3H)).

EXAMPLE 27

(rac)-4-{3-[1-(6-Fluoro-1-methyl-1H-indazol-5-yl)-ethyl]-imidazo[1,2-b]pyridazin-6-yl}-piperazin-2-one

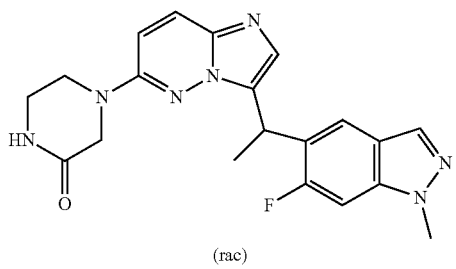 [SMILES: CC(c1cc2cnn(C)c2cc1F)c1cnc2ccc(N3CCNC(=O)C3)nn12]

(rac)

(rac)-6-Chloro-3-[1-(6-fluoro-1-methyl-1H-indazol-5-yl)-ethyl]-imidazo[1,2-b]pyridazine (Intermediate G, 100 mg, 0.303 mmol), KF (88 mg, 1.5 mmol), piperazin-2-one (91 mg, 0.91 mmol) were suspended in NMP (1 mL). The RM was stirred at 180° C. for 2 h. The mixture was diluted with EtOAc and washed with 1M $Na_2CO_3$ (1×) and water (2×). The aqueous was further extracted with EtOAc (2×). The combined organic layers were dried over $Na_2SO_4$, filtered and concentrated. The residue was purified by preparative UPLC with acetonitrile and water (+0.1% TFA). The fractions were joined and were lyophilized. The residue was dissolved in MeOH and it was passed through an SPE cartridge of $HCO_3$ to remove the TFA salt. The filtrate was evaporated and the residue was triturated with pentane. The precipitate was filtered off and dried to afford the title compound as a white solid ($t_R$ 0.88 min (conditions 4), MH+=394, $^1$H-NMR in DMSO-d6: 8.10 (br. s, 1H); 7.95-7.87 (m, 2H); 7.65 (s, 1H); 7.51 (s, 1H); 7.54 (d, 1H); 7.49 (s, 1H); 7.22 (d, 1H); 4.79 (q, 1H); 3.95 (s, 4H); 3.87-3.78 (m, 1H); 3.67-3.55 (m, 2H); 3.22 (dd, 1H); 3.29-3.14 (m, 1H); 1.71 (d, 3H)).

EXAMPLE 28

4-{3-[(S)-1-(6-Fluoro-1-methyl-1H-indazol-5-yl)-ethyl]-imidazo[1,2-b]pyridazin-6-yl}-piperazin-2-one

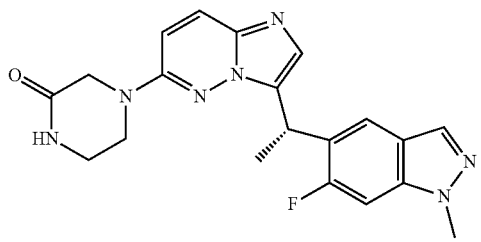 [SMILES: C[C@@H](c1cc2cnn(C)c2cc1F)c1cnc2ccc(N3CCNC(=O)C3)nn12]

6-Chloro-3-[(S)-1-(6-fluoro-1-methyl-1H-indazol-5-yl)-ethyl]-imidazo[1,2-b]pyridazine (Intermediate E, 66.0 mg, 0.2 mmol), KF (59.3 mg, 1.0 mmol) and piperazin-2-one (61.9 mg, 0.6 mmol) were suspended in NMP (0.5 mL). The RM was stirred at 180° C. for 3 h. The mixture was diluted with $CH_3CN$ and purified by reverse phase chromatography (Büchi MPLC: 5-24% $CH_3CN$, 0.1% HCOOH). The fractions was combined, concentrated and neutralized with $NaHCO_3$, extracted with EtOAc. The combined organics layers were tried over $Na_2SO_4$, filtered, concentrated to afford the title compound as a yellow foam ($t_R$ 3.53 min (conditions 4), ($t_R$ 8.25 (conditions 5), MH+=394.3, $^1$H-NMR in DMSO-d6: 8.04 (s, 1H); 7.92 (s, 1H); 7.81 (d, 1H); 7.50 (m, 1H); 7.46 (d, 1H); 7.06 (d, 1H); 4.78 (m, 1H); 3.95 (s, 3H); 3.95 (d, 1H); 3.80 (d, 1H); 3.58 (m, 2H); 3.22 (m, 2H); 1.71 (d, 3H)).

EXAMPLE 29

1-(4-{3-[(S)-1-(6-Fluoro-1-methyl-1H-indazol-5-yl)-ethyl]-imidazo[1,2-b]pyridazin-6-yl}-piperazin-1-yl)-ethanone

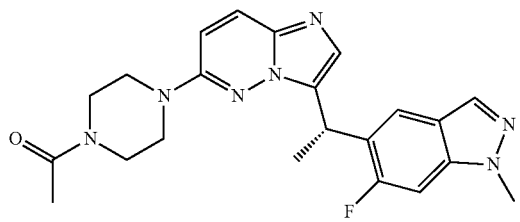 [SMILES: CC(=O)N1CCN(c2ccc3ncc([C@@H](C)c4cc5cnn(C)c5cc4F)n3n2)CC1]

The title compound was prepared analogy to Example 38 using 6-chloro-3-[(S)-1-(6-fluoro-1-methyl-1H-indazol-5-yl)-ethyl]-imidazo[1,2-b]pyridazine (Intermediate E) (50 mg, 0.153 mmol) and 1-acetylpiperazine (39.2 mg, 0.306 mmol) ($t_R$ 3.67 min (conditions 5), MH+=421, $^1$H-NMR in DMSO-d6: 7.93 (s, 1H); 7.81 (d, 1H); 7.52 (d, 1H); 7.50 (s, 1H); 7.47 (d, 1H); 4.75 (m, 1H); 3.95 (s, 3H); 3.42 (m, 6H); 2.00 (s, 3H); 1.70 (d, 3H)).

EXAMPLE 30

4-[3-(5,7-Difluoro-quinolin-6-ylmethyl)-imidazo[1,2-b]pyridazin-6-yl]-1-methyl-piperazin-2-one

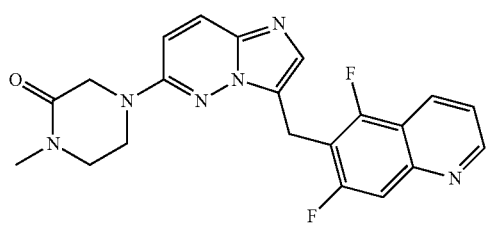 [SMILES: CN1CCN(c2ccc3ncc(Cc4c(F)cc5ncccc5c4F)n3n2)CC1=O]

The title compound was prepared in analogy to Example 1 using 6-(6-chloro-imidazo[1,2-b]pyridazin-3-ylmethyl)-5,7-difluoro-quinoline (Intermediate H) instead of (rac)-6-[1-(6-chloro-imidazo[1,2-b]pyridazin-3-yl)-ethyl]-5,7-difluoro-quinoline. ($t_R$ 3.49 min (conditions 5), MH+=409.1, $^1$H-NMR in DMSO-d6: 8.94 (m, 1H); 8.48 (d, 1H); 7.83 (d, 1H); 7.66 (d, 1H); 7.60 (m, 1H); 7.40 (s, 1H); 7.12 (d, 1H); 4.43 (s, 2H); 4.02 (s, 2H); 3.73 (m, 2H); 3.38 (m, 2H); 2.85 (s, 3H)).

EXAMPLE 31

4-[3-(5,7-Difluoro-quinolin-6-ylmethyl)-imidazo[1,2-b]pyridazin-6-yl]-piperazin-2-one

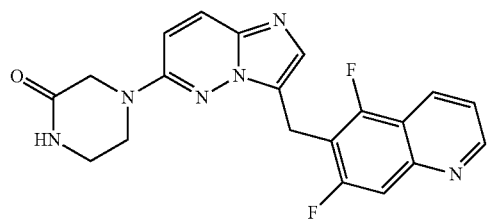 [SMILES: O=C1CN(c2ccc3ncc(Cc4c(F)cc5ncccc5c4F)n3n2)CCN1]

The title compound was prepared in analogy to Example 3 using 6-(6-chloro-imidazo[1,2-b]pyridazin-3-ylmethyl)-5,7-difluoro-quinoline (Intermediate H) ($t_R$ 2.79 min (conditions 1), MH+=395, $^1$H-NMR in DMSO-d6: 8.97 (d, 1H); 8.49 (d, 1H); 8.12 (s, 1H); 7.84 (d, 1H); 7.68 (d, 1H); 7.61 (m, 1H); 7.41 (s, 1H); 7.11 (d, 1H); 4.45 (s, 2H); 3.99 (s, 2H); 3.66 (m, 2H); 3.27 (m, 2H)).

EXAMPLE 32

5,7-Difluoro-6-(6-piperazin-1-yl-imidazo[1,2-b]pyridazin-3-ylmethyl)-quinoline

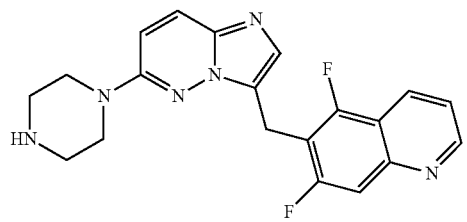 [SMILES: Fc1cc2ncccc2c(F)c1Cc1cnc2ccc(N3CCNCC3)nn12]

The title compound was prepared analogy to Example 6 using 6-(6-chloro-imidazo[1,2-b]pyridazin-3-ylmethyl)-5,7-difluoro-quinoline (Intermediate H) ($t_R$ 2.96 min (conditions 5), MH+=381.2, $^1$H-NMR in DMSO-d6: 8.94 (d, 1H); 8.46 (d, 1H); 8.75 (d, 1H); 7.67 (d, 1H); 7.59 (m, 1H); 7.37 (s, 1H); 7.05 (d, 1H); 4.41 (s, 2H); 3.30 (m, 4H); 2.70 (m, 4H)).

EXAMPLE 33

5,7-Difluoro-6-[6-(4-methyl-piperazin-1-yl)-imidazo[1,2-b]pyridazin-3-ylmethyl]-quinoline

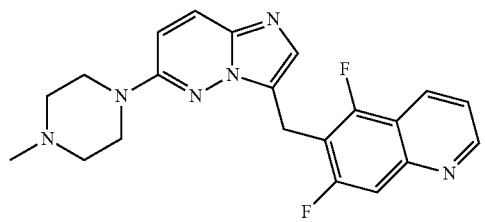 [SMILES: CN1CCN(c2ccc3ncc(Cc4c(F)cc5ncccc5c4F)n3n2)CC1]

The title compound was prepared in analogy to Example 8 using 6-(6-chloro-imidazo[1,2-b]pyridazin-3-ylmethyl)-5,7-difluoro-quinoline (Intermediate H) ($t_R$ 2.97 min (conditions 5), MH+=395.1, $^1$H-NMR, 600 MHz in DMSO-d6: 9.03 (d, 1H); 8.55 (d, 1H); 8.28 (d, 1H); 8.17 (s, 1H); 7.78 (m, 2H); 7.66 (m, 1H); 4.55 (s, 2H); 4.39 (d, 2H); 3.56 (d, 2H); 3.33 (m, 2H) 3.07 (m, 2H); 2.80 (s, 3H)).

EXAMPLE 34

1-{4-[3-(5,7-Difluoro-quinolin-6-ylmethyl)-imidazo[1,2-b]pyridazin-6-yl]-piperazin-1-yl}-ethanone

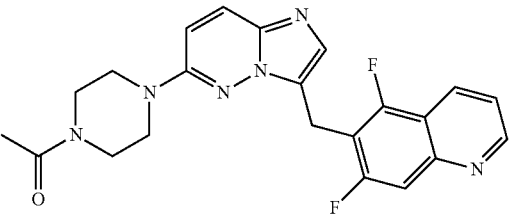 [SMILES: CC(=O)N1CCN(c2ccc3ncc(Cc4c(F)cc5ncccc5c4F)n3n2)CC1]

The title compound was prepared in analogy to Example 10 using 5,7-difluoro-6-(6-piperazin-1-yl-imidazo[1,2-b]pyridazin-3-ylmethyl)-quinoline (Example 32) ($t_R$ 3.58 min (conditions 5), MH+=423.1, $^1$H-NMR in DMSO-d6: 8.95 (d, 1H); 8.49 (d, 1H); 7.81 (d, 1H); 7.68 (d, 1H); 7.59 (m, 1H); 7.40 (s, 1H); 7.11 (d, 1H); 4.42 (s, 2H); 3.47 (s, 6H); 3.40 (m, 2H); 2.01 (s, 3H)).

EXAMPLE 35

4-[3-(5,7-Difluoro-quinolin-6-ylmethyl)-imidazo[1,2-b]pyridazin-6-yl]-piperazine-1-carbaldehyde

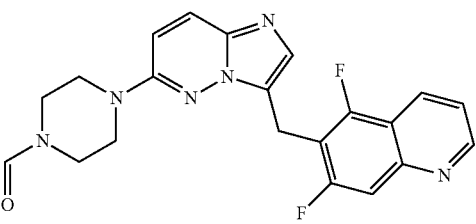 [SMILES: O=CN1CCN(c2ccc3ncc(Cc4c(F)cc5ncccc5c4F)n3n2)CC1]

The title compound was prepared in analogy to Example 12 using 5,7-difluoro-6-(6-piperazin-1-yl-imidazo[1,2-b]pyridazin-3-ylmethyl)-quinoline (Example 32) ($t_R$ 3.53 min (conditions 5), MH+=409.1, $^1$H-NMR in DMSO-d6: 8.95 (d, 1H); 8.48 (d, 1H); 8.06 (s, 1H); 7.83 (d, 1H); 7.68 (d, 1H); 7.60 (m, 1H); 7.42 (s, 1H); 7.14 (d, 1H); 4.43 (s, 2H); 3.50 (m, 2H); 3.42 (s, 2H); 3.32 (s, 4H)).

EXAMPLE 36

4-[3-(5,7-Difluoro-quinolin-6-ylmethyl)-imidazo[1,2-b]pyridazin-6-yl]-piperazine-1-carboxylic acid methyl ester

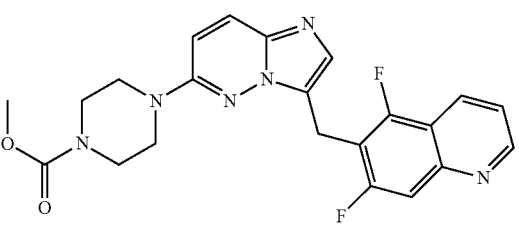 [SMILES: COC(=O)N1CCN(c2ccc3ncc(Cc4c(F)cc5ncccc5c4F)n3n2)CC1]

The title compound was prepared in analogy to Example 14 using 5,7-difluoro-6-(6-piperazin-1-yl-imidazo[1,2-b]pyridazin-3-ylmethyl)-quinoline (Example 32) ($t_R$ 3.88 min (conditions 5), MH+=439.1, $^1$H-NMR in DMSO-d6: 8.95 (d, 1H); 8.48 (d, 1H); 7.83 (d, 1H); 7.68 (d, 1H); 7.60 (m, 1H); 7.44 (s, 1H); 7.13 (d, 1H); 4.43 (s, 2H); 3.61 (s, 3H); 3.42 (m, 8H)).

EXAMPLE 37

4-[3-(7-Fluoro-quinolin-6-ylmethyl)-imidazo[1,2-b]pyridazin-6-yl]-1-methyl-piperazin-2-one

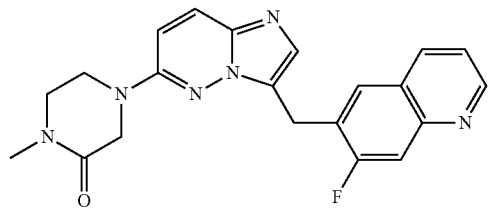 [SMILES: CN1CCN(c2ccc3ncc(Cc4cc5cccnc5cc4F)n3n2)CC1=O]

The title compound was prepared in analogy to Example 38 using 6-(6-chloro-imidazo[1,2-b]pyridazin-3-ylmethyl)-7-fluoro-quinoline (Intermediate J, 50 mg, 0.160 mmol) and 1-methylpiperazin-2-one hydrochloride (36.5 mg, 0.320 mmol) ($t_R$ 3.11 min (conditions 5), MH+=391, $^1$H-NMR in DMSO-d6: 8.84 (d, 1H); 8.33 (d, 1H); 7.95 (s, 1H); 7.85 (d, 1H); 7.71 (d, 1H); 7.48 (m, 1H); 7.46 (s, 1H); 7.15 (d, 1H); 4.42 (s, 2H); 4.06 (s, 2H); 3.75 (m, 2H); 3.49 (m, 2H); 2.83 (m, 3H)).

EXAMPLE 38

4-[3-(7-Fluoro-quinolin-6-ylmethyl)-imidazo[1,2-b]pyridazin-6-yl]-piperazin-2-one

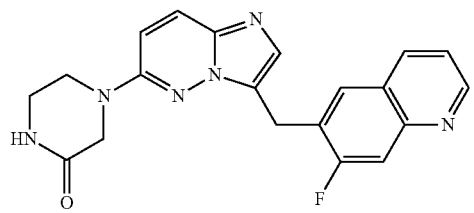 [SMILES: O=C1CN(c2ccc3ncc(Cc4cc5cccnc5cc4F)n3n2)CCN1]

The title compound was prepared using 6-(6-chloro-imidazo[1,2-b]pyridazin-3-ylmethyl)-7-fluoro-quinoline (Intermediate J, 50 mg, 0.160 mmol), piperazin-2-one (80 mg, 0.799 mmol) and KF (27.9 mg, 0.480 mmol) were suspended in NMP (1.0 mL). The RM was stirred at 180° C. for 5 h. The mixture was diluted with EtOAc and washed with 1M NaHCO$_3$ (1×) and water (2×). The combined organic layers were dried over Na$_2$SO$_4$, filtered and concentrated. The residue was purified by flash chromatography and afforded the title compound as a foam ($t_R$ 2.88 min (conditions 5), MH+=377, $^1$H-NMR in DMSO-d6: 8.85 (d, 1H); 8.33 (d, 1H); 8.07 (s, 1H); 7.98 (d, 1H); 7.83 (d, 1H); 7.74 (m, 1H); 7.5 (s, 2H); 7.11 (d, 1H); 4.41 (s, 2H); 4.00 (s, 2H); 3.67 (m, 2H); 3.26 (m, 2H)).

EXAMPLE 39

1-{4-[3-(7-Fluoro-quinolin-6-ylmethyl)-imidazo[1,2-b]pyridazin-6-yl]-piperazin-1-yl}-ethanone

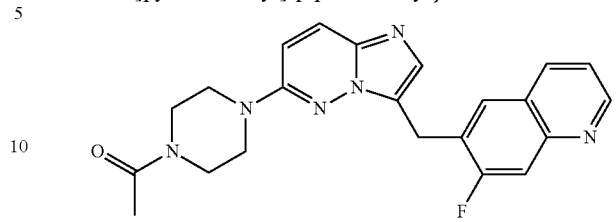

The title compound was prepared in analogy to Example 38 using 6-(6-chloro-imidazo[1,2-b]pyridazin-3-ylmethyl)-7-fluoro-quinoline (Intermediate J, 50 mg, 0.160 mmol) and 1-acetylpiperazine (41.0 mg, 0.320 mmol) ($t_R$ 3.17 min (conditions 5), MH+=391, $^1$H-NMR in DMSO-d6: 8.85 (d, 1H); 8.33 (d, 1H); 7.94 (d, 1H); 7.84 (d, 1H); 7.74 (d, 1H); 7.46 (m, 1H); 7.44 (s, 1H); 7.14 (d, 1H); 4.40 (s, 2H); 3.48 (s, 6H); 3.42 (m, 2H); 2.00 (s, 3H)).

EXAMPLE 40

(rac)-4-{3-[1-(7-Fluoro-quinolin-6-yl)-ethyl]-imidazo[1,2-b]pyridazin-6-yl}-1-methyl-piperazin-2-one

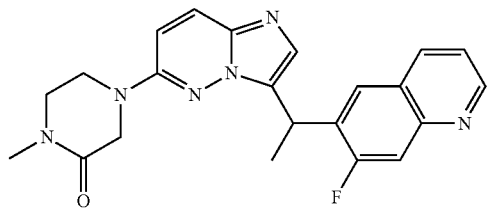 [SMILES: CC(c1cc2cccnc2cc1F)c1cnc2ccc(N3CCN(C)C(=O)C3)nn12]

The title compound was prepared in analogy to Example 38 using (rac)-6-[1-(6-chloro-imidazo[1,2-b]pyridazin-3-yl)ethyl]-7-fluoro-quinoline (Intermediate K, 50 mg, 0.153 mmol), 1-methylpiperazin-2-one hydrochloride (46.1 mg, 0.306 mmol) ($t_R$ 3.24 min (conditions 5), MH+=404, $^1$H-NMR in DMSO-d6: 8.83 (d, 1H); 8.28 (d, 1H); 7.84 (s, 1H); 7.81 (d, 1H); 7.72 (d, 1H); 7.56 (s, 1H); 7.43 (m, 1H); 7.11 (d, 1H); 4.88 (m, 1H); 3.98 (d, 1H); 3.83 (m, 1H); 3.25 (m, 2H); 2.77 (s, 3H); 1.78 (d, 3H)).

EXAMPLE 41

(rac)-4-{3-[1-(7-Fluoro-quinolin-6-yl)-ethyl]-imidazo[1,2-b]pyridazin-6-yl}-piperazin-2-one

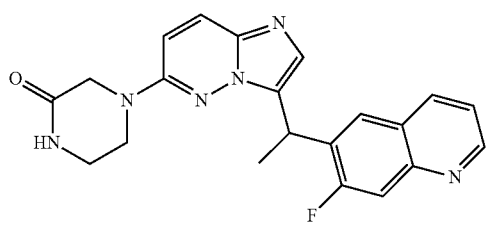 [SMILES: CC(c1cc2cccnc2cc1F)c1cnc2ccc(N3CCNC(=O)C3)nn12]

The title compound was prepared in analogy to Example 3 using (rac)-6-[1-(6-chloro-imidazo[1,2-b]pyridazin-3-yl)-ethyl]-7-fluoro-quinoline (Intermediate K) instead of (rac)-6-

[1-(6-chloro-imidazo[1,2-b]pyridazin-3-yl)-ethyl]-5,7-difluoro-quinoline (t$_R$ 2.55 min (conditions 1), MH+=391.1, $^1$H-NMR in DMSO-d6: 8.85 (d, 1H); 8.31 (d, 1H); 8.07 (s, 1H); 7.85 (m, 2H); 7.74 (d, 1H); 7.55 (s, 1H); 7.46 (m, 1H); 7.09 (d, 1H); 4.91 (m, 1H); 3.97 (d, 1H); 3.80 (d, 1H); 3.58 (m, 2H); 3.20 (m, 2H); 1.80 (d, 3H)).

EXAMPLE 42

(rac)-1-(4-{3-[1-(7-Fluoro-quinolin-6-yl)-ethyl]-imidazo[1,2-b]pyridazin-6-yl}-piperazin-1-yl)ethanone

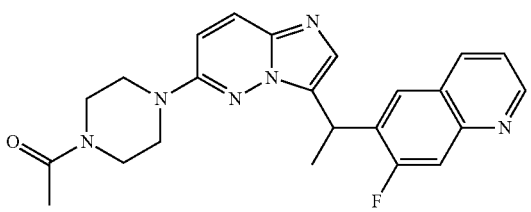 [SMILES: CC(=O)N1CCN(c2ccc3ncc(C(C)c4cc5cccnc5cc4F)n3n2)CC1]

The title compound was prepared in analogy to Example 38 using (rac)-6-[1-(6-chloro-imidazo[1,2-b]pyridazin-3-yl)-ethyl]-7-fluoro-quinoline (Intermediate K, 50 mg, 0.153 mmol) and 1-acetylpiperazine (39.2 mg, 0.306 mmol) (t$_R$ 3.33 min (conditions 5), MH+=419, $^1$H-NMR in DMSO-d6: 8.83 (d, 1H); 8.30 (d, 1H); 7.83 (d, 1H); 7.74 (d, 1H); 7.56 (s, 1H); 7.44 (m, 1H); 7.10 (d, 1H); 4.87 (m, 1H); 3.37 (m, 8H); 1.98 (s, 3H); 1.78 (d, 3H)).

EXAMPLE 43

4-[3-(5-Fluoro-quinolin-6-ylmethyl)-imidazo[1,2-b]pyridazin-6-yl]-1-methyl-piperazin-2-one

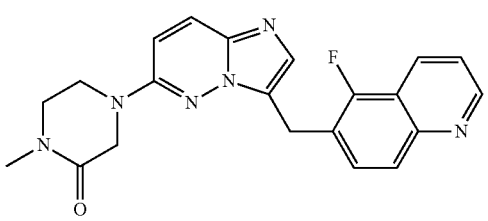 [SMILES: CN1CCN(c2ccc3ncc(Cc4ccc5ncccc5c4F)n3n2)CC1=O]

The title compound was prepared in analogy to Example 38 using 6-(6-chloro-imidazo[1,2-b]pyridazin-3-ylmethyl)-5-fluoro-quinoline (Intermediate N, 70 mg, 0.224 mmol), 1-methylpiperazin-2-one hydrochloride (67.4 mg, 0.448 mmol) (t$_R$ 3.31 min (conditions 5), MH+=391, $^1$H-NMR in DMSO-d6: 8.91 (m, 1H); 8.47 (d, 1H); 7.85 (d, 1H); 7.78 (d, 1H); 7.69 (d, 1H); 7.66 (s, 1H); 7.61 (m, 1H); 7.50 (s, 1H); 4.42 (s, 2H); 4.03 (s, 2H); 3.74 (m, 2H); 3.35 (m, 2H); 2.84 (s, 3H)).

EXAMPLE 44

4-[3-(5-Fluoro-quinolin-6-ylmethyl)-imidazo[1,2-b]pyridazin-6-yl]-piperazin-2-one

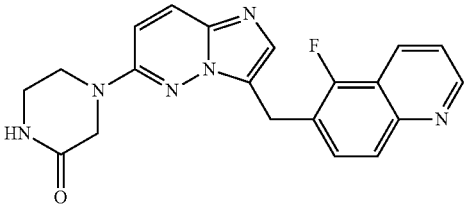 [SMILES: O=C1CN(c2ccc3ncc(Cc4ccc5ncccc5c4F)n3n2)CCN1]

The title compound was prepared in analogy to Example 38 6-(6-chloro-imidazo[1,2-b]pyridazin-3-ylmethyl)-5-fluoro-quinoline (Intermediate N, 100 mg, 0.320 mmol), piperazin-2-one (96 mg, 0.959 mmol) (t$_R$ 3.16 min (conditions 5), MH+=377, $^1$H-NMR in DMSO-d6: 8.91 (m, 1H); 8.47 (d, 1H); 8.07 (s, 1H); 7.84 (d, 1H); 7.78 (d, 1H); 7.69 (m, 1H); 7.60 (m, 1H); 7.47 (s, 1H); 7.12 (d, 1H); 4.42 (s, 2H); 3.98 (s, 2H); 3.66 (m, 2H); 3.25 (m, 4H)).

EXAMPLE 45

1-{4-[3-(5-Fluoro-quinolin-6-ylmethyl)-imidazo[1,2-b]pyridazin-6-yl]-piperazin-1-yl}-ethanone

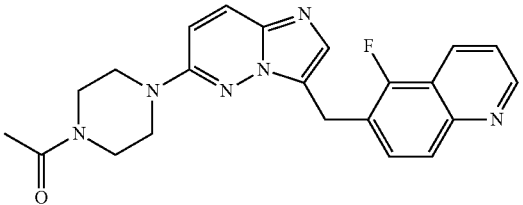 [SMILES: CC(=O)N1CCN(c2ccc3ncc(Cc4ccc5ncccc5c4F)n3n2)CC1]

The title compound was prepared in analogy to Example 38 using 6-(6-chloro-imidazo[1,2-b]pyridazin-3-ylmethyl)-5-fluoro-quinoline (Intermediate N, 70 mg, 0.224 mmol) and 1-acetylpiperazine (57.4 mg, 0.448 mmol) (t$_R$ 3.40 min (conditions 5), MH+=405, $^1$H-NMR in DMSO-d6: 8.92 (m, 1H); 8.49 (d, 1H); 7.83 (d, 1H); 7.79 (d, 1H); 7.67 (m, 1H); 7.61 (m, 1H); 7.45 (s, 1H); 7.13 (d, 1H); 4.41 (s, 2H); 3.47 (s, 4H); 3.41 (m, 1H); 3.28 (m, 1H); 2.00 (s, 3H)).

EXAMPLE 46

(rac)-4-{3-[1-(5-Fluoro-quinolin-6-yl)-ethyl]-imidazo[1,2-b]pyridazin-6-yl}-1-methyl-piperazin-2-one

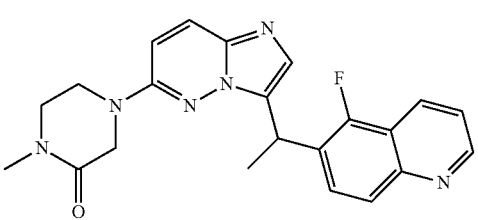 [SMILES: CC(c1ccc2ncccc2c1F)c1cnc2ccc(N3CCN(C)C(=O)C3)nn12]

The title compound was prepared in analogy to Example 38 using (rac)-6-(6-chloro-imidazo[1,2-b]pyridazin-3-ylmethyl)-5-fluoro-quinoline (Intermediate O, 100 mg, 0.306 mmol) and 1-methylpiperazin-2-one hydrochloride (92 mg, 0.612 mmol) ($t_R$ 3.44 min (conditions 5), MH+=405, $^1$H-NMR in DMSO-d6: 8.91 (m, 1H); 8.49 (d, 1H); 7.94 (d, 1H); 7.75 (d, 1H); 7.68 (s, 1H); 7.60 (m, 1H); 7.55 (m, 1H); 7.12 (d, 1H); 4.97 (m, 1H); 4.01 (d, 1H); 3.77 (d, 1H); 3.62 (m, 2H); 3.23 (m, 2H); 2.77 (s, 3H); 1.77 (d, 3H)).

EXAMPLE 47

(rac)-4-{3-[1-(5-Fluoro-quinolin-6-yl)-ethyl]-imidazo[1,2-b]pyridazin-6-yl}-piperazin-2-one

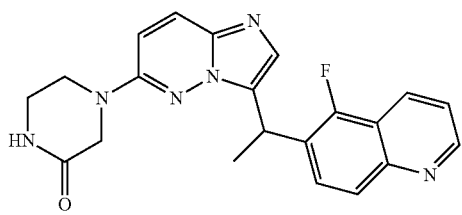 [SMILES: CC(c1ccc2ncccc2c1F)c1cnc2ccc(N3CCNC(=O)C3)nn12]

The title compound was prepared in analogy to Example 38 using (rac)-6-(6-chloro-imidazo[1,2-b]pyridazin-3-ylmethyl)-5-fluoro-quinoline (Intermediate O, 100 mg, 0.320 mmol) and piperazin-2-one (92 mg, 0.918 mmol) ($t_R$ 3.33 min (conditions 5), MH+=391, $^1$H-NMR in DMSO-d6: 8.91 (m, 1H); 8.48 (d, 1H); 8.00 (s, 1H); 7.81 (d, 1H); 7.74 (d, 1H); 7.59 (m, 3H); 7.05 (d, 1H); 4.97 (m, 1H); 3.96 (d, 1H); 3.72 (d, 1H); 3.54 (m, 2H); 3.15 (m, 2H); 1.77 (d 3H)).

EXAMPLE 48

(rac)-1-(4-{3-[1-(5-Fluoro-quinolin-6-yl)-ethyl]-imidazo[1,2-b]pyridazin-6-yl}-piperazin-1-yl)ethanone

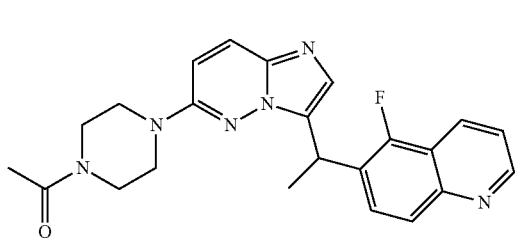 [SMILES: CC(=O)N1CCN(c2ccc3ncc(C(C)c4ccc5ncccc5c4F)n3n2)CC1]

The title compound was prepared in analogy to Example 38 using (rac)-6-(6-chloro-imidazo[1,2-b]pyridazin-3-ylmethyl)-5-fluoro-quinoline (Intermediate O, 100 mg, 0.306 mmol) and 1-acetylpiperazine (78 mg, 0.612 mmol) ($t_R$ 3.56 min (conditions 5), MH+=419, $^1$H-NMR in DMSO-d6: 8.92 (m, 1H); 8.52 (d, 1H); 7.79 (d, 1H); 7.75 (d, 1H); 7.60 (m, 2H); 7.53 (m, 1H); 7.05 (d, 1H); 4.95 (s, 1H); 3.34 (m, 8H); 1.95 (s, 3H); 1.77 (d, 3H)).

EXAMPLE 49

(rac)-4-(3-(1-(4,6-difluoro-1-methyl-1H-indazol-5-yl)ethyl)imidazo[1,2-b]pyridazin-6-yl)-1-methylpiperazin-2-one

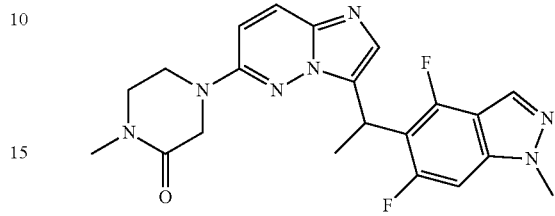

(rac)-6-chloro-3-(1-(6-fluoro-1-methyl-1H-indazol-5-yl) ethyl)imidazo[1,2-b]pyridazine (Intermediate R, 69.5 mg, 0.2 mmol), KF (58.1 mg, 1.0 mmol) and 1-methylperazine-2-one hydrochloride (95.0 mg, 0.6 mmol) were suspended in NMP (0.5 mL). The RM was stirred at 180° C. for 4.5 h. The mixture was diluted with CH$_3$CN and purified by reverse phase chromatography (Büchi MPLC: 3-26% CH$_3$CN, 0.1% HCOOH). The fractions was combined, concentrated and neutralized with NaHCO$_3$, extracted with EtOAc. The combined organics layers were tried over Na$_2$SO$_4$, filtered, concentrated to afford the title compound as a light brown foam ($t_R$ 3.76 min (conditions 4), MH+=426.2, $^1$H-NMR in DMSO-d6: 8.08 (s, 1H); 7.80 (d, 1H); 7.53 (s, 1H); 7.36 (d, 1H); 7.05 (d, 1H); 4.85 (m, 1H); 4.01 (d, 1H); 3.95 (s, 3H); 3.77 (d, 1H); 3.62 (m, 2H); 3.25 (m, 2H); 2.81 (s, 3H); 1.79 (d, 3H)).

EXAMPLE 50

4-{3-[(S)-1-(4,6-Difluoro-1-methyl-1H-indazol-5-yl)-ethyl]-imidazo[1,2-b]pyridazin-6-yl}-1-methyl-piperazin-2-one

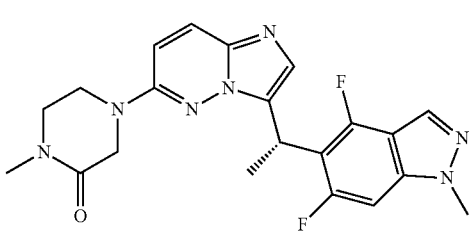

6-Chloro-3-[(S)-1-(4,6-difluoro-1-methyl-1H-indazol-5-yl)-ethyl]-imidazo[1,2-b]pyridazine (Intermediate Q, 50.0 mg, 0.144 mmol), KF (42.6 mg, 0.719 mmol) and 1-methylperazine-2-one hydrochloride (67.0 mg, 0.431 mmol) were suspended in NMP (0.4 mL). The RM was stirred at 180° C. for 4 h. The mixture was diluted with EtOAc and washed with NaHCO$_3$ 10% (2×) and water (4×). The combined organic layers were dried over Na$_2$SO$_4$, filtered and concentrated. The residue was purified by flash chromatography and afforded the title compound as a light brown foam ($t_R$ 3.75 min (conditions 5), ($t_R$ 11.35 min (conditions 2), MH+=425.9, $^1$H-NMR in DMSO-d6: 8.07 (s, 1H); 7.80 (d, 1H); 7.52 (s, 1H); 7.36 (d, 1H); 7.05 (d, 1H); 4.85 (m, 1H); 4.01 (d, 1H); 3.95 (s, 3H); 3.78 (d, 1H); 3.62 (m, 2H); 3.27 (m, 2H); 2.81 (s, 3H); 1.79 (d, 3H)).

EXAMPLE 51

(rac)-4-{3-[1-(4,6-difluoro-1-methyl-1H-indazol-5-yl)-ethyl]-imidazo[1,2-b]pyridazine-}-piperidin-2-one

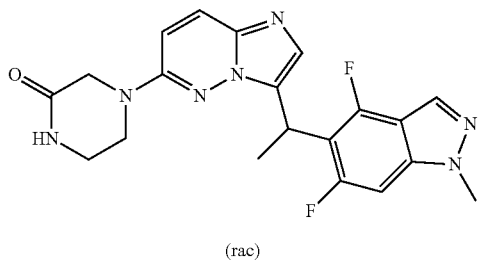 [SMILES: CC(c1c(F)cc2c(cnn2C)c1F)c1cnc2ccc(N3CCNC(=O)C3)nn12]

(rac)

The title compound was prepared in analogy to Example 28 using (rac)-6-chloro-3-[1-(4,6-difluoro-1-methyl-1H-indazol-5-yl)-ethyl]-imidazo[1,2-b]pyridazine (Intermediate R) instead of (rac)-6-chloro-3-[1-(6-fluoro-1-methyl-1H-indazol-5-yl)-ethyl]-imidazo[1,2-b]pyridazine ($t_R$ 0.96 min (conditions 4), MH+=412, $^1$H-NMR in DMSO-d6: 8.13-8.00 (m, 2H); 7.80 (d, 1H); 7.54 (s, 1H); 7.37 (d, 1H); 7.04 (d, 1H); 4.85 (d, 1H); 4.02-3.89 (m, 4H); 3.72 (d, 1H); 3.54 (q, 2H); 3.21 (d, 1H); 3.13 (d, 1H); 1.79 (d, 3H)).

EXAMPLE 52

4-{3-[(S)-1-(4,6-Difluoro-1-methyl-1H-indazol-5-yl)-ethyl]-imidazo[1,2-b]pyridazin-6-yl}-piperazin-2-one

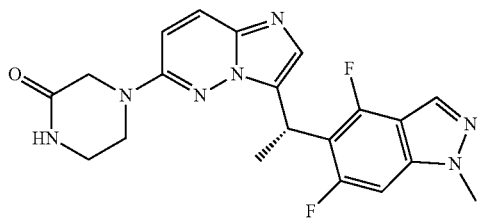 [SMILES: C[C@@H](c1c(F)cc2c(cnn2C)c1F)c1cnc2ccc(N3CCNC(=O)C3)nn12]

6-Chloro-3-[(S)-1-(4,6-difluoro-1-methyl-1H-indazol-5-yl)-ethyl]-imidazo[1,2-b]pyridazine (Intermediate Q, 50 mg, 0.144 mmol), KF, 42.6 mg, 0.719 mmol) and piperazin-2-one (44.5 mg, 0.431 mmol) were suspended in NMP (0.3 mL). The RM was stirred at 170° C. for 3 h. The mixture was diluted with EtOAc and washed with NaHCO₃ 10% (2×) and water (4×). The combined organic layers were dried over Na₂SO₄, filtered and concentrated. The residue was purified by flash chromatography and then crystallized in EtOAc/Pentane to afford the title compound as a light brown solid ($t_R$ 3.63 min (conditions 5), ($t_R$ 10.82 min (conditions 2), MH+=412.2, $^1$H-NMR in DMSO-d6: 8.07 (s, 1H); 8.03 (s, 1H); 7.79 (d, 1H); 7.52 (s, 1H); 7.36 (d, 1H); 7.02 (d, 1H); 4.85 (m, 1H); 3.95 (d, 1H); 3.95 (s, 3H); 3.73 (d, 1H); 3.54 (m, 2H); 3.17 (m, 2H); 1.79 (d, 3H)).

EXAMPLE 53

1-(4-{3-[(S)-1-(4,6-Difluoro-1-methyl-1H-indazol-5-yl)-ethyl]-imidazo[1,2-b]pyridazin-6-yl}-piperazin-1-yl)-ethanone

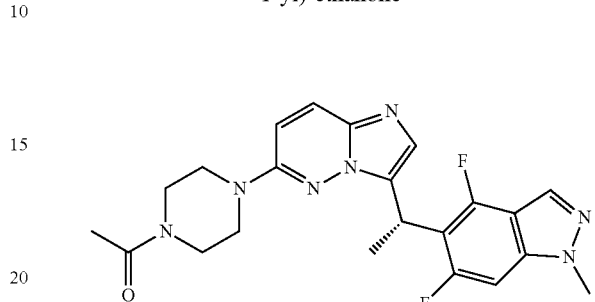

6-Chloro-3-[(S)-1-(4,6-difluoro-1-methyl-1H-indazol-5-yl)-ethyl]-imidazo[1,2-b]pyridazine (Intermediate Q, 36.6 mg, 0.105 mmol), KF (30.6 mg, 0.526 mmol) and 1-acetylpiperazine (40.5 mg, 0.316 mmol) were suspended in NMP (0.4 mL). The RM was stirred at 180° C. for 3.5 h. The mixture was diluted with EtOAc and washed with NaHCO₃ 10% (2×) and water (4×). The combined organic layers were dried over Na₂SO₄, filtered and concentrated. The residue was purified by flash chromatography and afforded the title compound as a light brown foam ($t_R$ 3.80 min (conditions 5), $t_R$ 13.31 min (conditions 3), MH+=440.3, $^1$H-NMR in DMSO-d6: 8.12 (s, 1H); 7.79 (d, 1H); 7.52 (s, 1H); 7.39 (d, 1H); 7.04 (d, 1H); 4.84 (m, 1H); 3.96 (s, 3H); 3.36 (m, 8H); 1.99 (s, 3H); 1.79 (d, 3H)).

EXAMPLE 54

4-[3-(4,6-Difluoro-1-methyl-1H-indazol-5-ylmethyl)-imidazo[1,2-b]pyridazin-6-yl]-piperazin-2-one

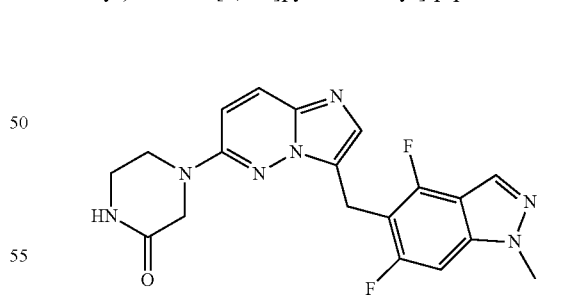

The title compound was prepared in analogy to Example 52 using 6-chloro-3-((4,6-difluoro-1-methyl-1H-indazol-5-yl)methyl)imidazo[1,2-b]pyridazine (Intermediate T, (100 mg, 0.300 mmol) and piperazin-2-one (90 mg, 0.899 mmol) ($t_R$ 3.47 min (conditions 4), MH+=398, $^1$H-NMR in DMSO-d6: 8.13 (s, 1H); 8.11 (s, 1H); 7.81 (d, 1H); 7.45 (d, 1H); 7.27 (s, 1H); 7.09 (d, 1H), 4.27 (s, 2H); 3.98 (m, 5H); 3.67 (m, 2H), 3.29 (m, 2H)).

EXAMPLE 55

1-(4-(3-((4,6-difluoro-1-methyl-1H-indazol-5-yl)methyl)imidazo[1,2-b]pyridazin-6-yl)piperazin-1-yl)ethanone

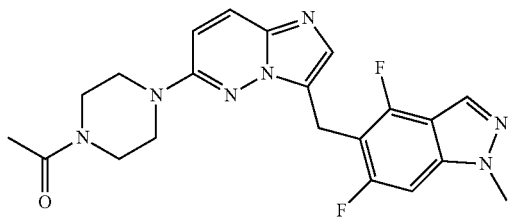 [SMILES: CC(=O)N1CCN(c2ccc3ncc(Cc4c(F)cc5c(cnn5C)c4F)n3n2)CC1]

6-chloro-3-((4,6-difluoro-1-methyl-1H-indazol-5-yl)methyl)imidazo[1,2-b]pyridazine (Intermediate T, 40.0 mg, 0.12 mmol), KF (34.8 mg, 0.6 mmol) and 1-acetylpiperazine (46.1 mg, 0.36 mmol) were suspended in NMP (0.3 mL). The RM was stirred at 180° C. for 3 h. The mixture was diluted with EtOAc and washed with NaHCO₃ 10% (2×) and water (4×). The combined organic layers were dried over Na₂SO₄, filtered and concentrated. The residue was purified by flash chromatography and afforded the title compound as a light brown foam ($t_R$ 3.72 min (conditions 5), MH+=426.3, ¹H-NMR in DMSO-d6: 8.16 (s, 1H); 7.80 (d, 1H); 7.46 (d, 1H); 7.27 (s, 1H); 7.10 (d, 1H); 4.27 (s, 2H); 3.98 (s, 3H); 3.50 (s, 6H); 3.44 (m, 2H); 2.03 (s, 3H)).

EXAMPLE 56

(rac)-4-(3-(1-(4,6-difluoro-1-isopropyl-1H-indazol-5-yl)ethyl)imidazo[1,2-b]pyridazin-6-yl)-1-methylpiperazin-2-one

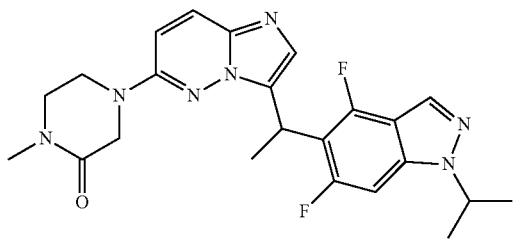 [SMILES: CC(c1c(F)cc2c(cnn2C(C)C)c1F)c1cnc2ccc(N3CCN(C)C(=O)C3)nn12]

(rac)-6-chloro-3-(1-(4,6-difluoro-1-isopropyl-1H-indazol-5-yl)ethyl)imidazo[1,2-b]pyridazine (Intermediate U, 56.4 mg, 0.15 mmol), KF (43.6 mg, 0.75 mmol) and 1-methylperazin-2-one hydrochloride (51.4 mg, 0.45 mmol) were suspended in NMP (0.4 mL). The RM was stirred at 180° C. for 4 h. The mixture was diluted with EtOAc and washed with NaHCO₃ 10% (2×) and water (4×). The combined organic layers were dried over Na₂SO₄, filtered and concentrated. The residue was purified by flash chromatography and afforded the title compound as a light brown foam ($t_R$ 4.06 min (conditions 5), MH+=454.3, ¹H-NMR in DMSO-d6: 8.09 (s, 1H); 7.81 (d, 1H); 7.53 (s, 1H); 7.43 (d, 1H); 7.05 (d, 1H); 4.86 (m, 2H); 4.03 (d, 1H); 3.81 (d, 1H); 3.64 (m, 2H); 3.24 (m, 2H); 2.80 (s, 3H); 1.79 (d, 3H), 1.41 (m, 6H)).

EXAMPLE 57

(rac)-4-(3-(1-(4,6-difluoro-1-isopropyl-1H-indazol-5-yl)ethyl)imidazo[1,2-b]pyridazin-6-yl)piperazin-2-one

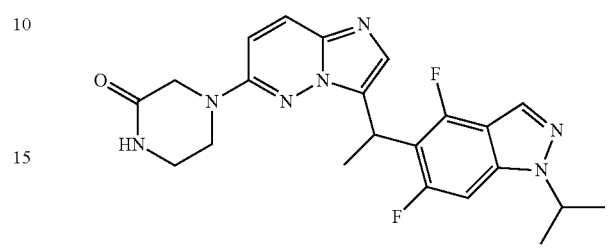

(rac)-6-chloro-3-(1-(4,6-difluoro-1-isopropyl-1H-indazol-5-yl)ethyl)imidazo[1,2-b]pyridazine (Intermediate U, 56.4 mg, 0.15 mmol), KF (44.5 mg, 0.75 mmol) and piperazin-2-one (46.4 mg, 0.45 mmol) were suspended in NMP (0.5 mL). The RM was stirred at 180° C. for 3 h. The mixture was diluted with CH₃CN and purified by reverse phase chromatography (Büchi MPLC: 5-28% CH₃CN, 0.1% HCOOH). The fractions was combined, concentrated and neutralized with NaHCO₃, extracted with EtOAc. The combined organics layers were tried over Na₂SO₄, filtered, concentrated, crystallized in EtOAc to afford the title compound as a white solid ($t_R$ 3.98 min (conditions 5), MH+=440.3, ¹H-NMR in DMSO-d6: 8.09 (s, 1H); 7.80 (d, 1H); 7.53 (s, 1H); 7.41 (d, 1H); 7.05 (d, 1H), 4.86 (m, 2H); 4.03 (d, 1H); 3.74 (d, 1H); 3.54 (d, 2H); 3.17 (m, 2H); 1.79 (d, 3H); 1.41 (m, 6H)).

EXAMPLE 58

(rac)-4-{3-[(S)-1-(5,7-Difluoro-quinolin-6-yl)-ethyl]-imidazo[1,2-b]pyridazin-6-yl}-3-methyl-piperazin-2-one

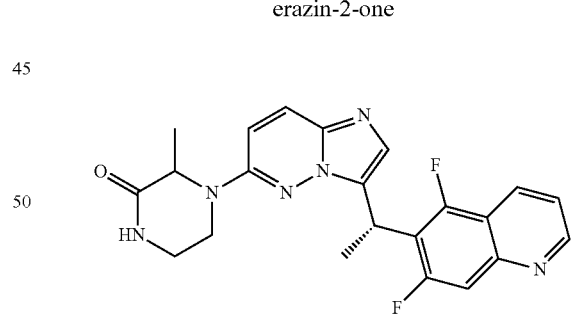

(rac, S)

The title compound was prepared in analogy to Example 18, using enantiomerically pure 6-[(S)-1-(6-chloro-imidazo[1,2-b]pyridazin-3-yl)-ethyl]-5,7-difluoro-quinoline (Intermediate B, 50 mg, 0.145 mmol) instead of the racemate and reverse phase chromatography (Büchi MPLC: 5-24% CH₃CN, 0.1% HCOOH) for the purification ($t_R$ 3.58 min (conditions 5), $t_R$ 7.38 and 8.53 min (conditions 2), MH+=423.1, ¹H-NMR in DMSO-d6: 8.92 (m, 1H); 8.46 (d, 1H); 7.90 (s, 1H); 7.80 (d, 1H); 7.69-7.54 (m, 3H); 7.02 (d, 1H); 4.95 (m, 1H); 4.51 and 4.28 (q, 1H); 3.87 (m, 1H); 3.38-2.88 (m, 3H); 1.86 (m, 3H); 1.32 and 0.92 (d, 3H)).

EXAMPLE 59

(R)-4-{3-[(S)-1-(5,7-Difluoro-quinolin-6-yl)-ethyl]-imidazo[1,2-b]pyridazin-6-yl}-3-methyl-piperazin-2-one

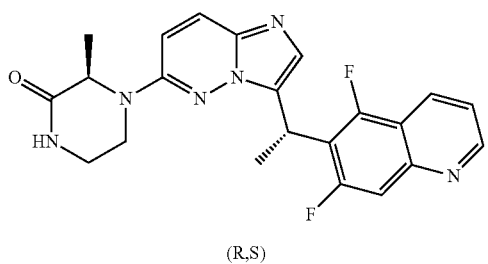 [SMILES: C[C@@H](c1c(F)cc2ncccc2c1F)c1cnc2ccc(N3CCNC(=O)[C@H]3C)nn12]

(R,S)

The title compound was prepared in analogy to Example 18, using enantiomerically pure 6-[(S)-1-(6-chloro-imidazo[1,2-b]pyridazin-3-yl)-ethyl]-5,7-difluoro-quinoline (Intermediate B, 50 mg, 0.145 mmol) and (R)-3-methyl-piperazin-2-one (33.1 mg, 0.29 mmol) instead of the racemates and flash chromatography for the purification. 2:1 mixture of title compound with compound of Example 60 ($t_R$ 3.59 min (conditions 5), $t_R$ 8.66 and 10.19 min (conditions 3, 90% n-hexane and 10% isopropanol), MH+=423.1, $^1$H-NMR in DMSO-d6: 8.91 (m, 1H); 8.42 (d, 1H); 7.90 (s, 1H); 7.80 (d, 1H); 7.69-7.50 (m, 3H); 7.05 (d, 1H); 4.93 (m, 1H); 4.50 and 4.28 (q, 1H); 3.87 (m, 1H); 3.43-2.89 (m, 3H); 1.84 (m, 3H); 1.30 and 0.93 (d, 3H)).

EXAMPLE 60

(S)-4-{3-[(S)-1-(5,7-Difluoro-quinolin-6-yl)-ethyl]-imidazo[1,2-b]pyridazin-6-yl}-3-methyl-piperazin-2-one

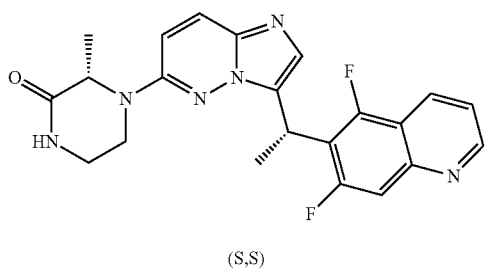 [SMILES: C[C@@H](c1c(F)cc2ncccc2c1F)c1cnc2ccc(N3CCNC(=O)[C@@H]3C)nn12]

(S,S)

The title compound was prepared in analogy to Example 18, using enantiomerically pure 6-[(S)-1-(6-chloro-imidazo[1,2-b]pyridazin-3-yl)-ethyl]-5,7-difluoro-quinoline (Intermediate B, 50 mg, 0.145 mmol) and (S)-3-methyl-piperazin-2-one (33.1 mg, 0.29 mmol) instead of the racemates and flash chromatography for the purification. 70:30 mixture of title compound with compound of Example 59 ($t_R$ 3.54 min (conditions 5), $t_R$ 8.63 and 10.13 min (conditions 3, 90% n-hexane and 10% isopropanol), MH+=423.1, $^1$H-NMR in DMSO-d6: 8.92 (m, 1H); 8.43 (d, 1H); 7.90 (s, 1H); 7.78 (d, 1H); 7.66-7.51 (m, 3H); 7.00 (d, 1H); 4.93 (m, 1H); 4.49 and 4.29 (q, 1H); 3.85 (m, 1H); 3.40-2.88 (m, 3H); 1.85 (m, 3H); 1.30 and 0.93 (d, 3H)).

C-Met Enzyme Assay

A number of compounds of the present invention were assayed in an antibody based kinase phosphorylation assay as follows.

Epk c-Met Profiling Assay:

The EPK kinase assay for c-Met receptor tyrosine kinase was developed, using the purified recombinant GST-fusion protein, containing the cytoplasmic domain of the enzyme. GST-c-Met(969-1390) was purified by affinity chromatography.

The kinase assay is based on the LanthaScreen™ technology. LanthaScreen™ is the detection of Time-Resolved Fluorescence Resonance Energy Transfer (TR-FRET) using lanthanide chelates to measure interactions between various binding partners. In a TR-FRET kinase assay, a long-lifetime lanthanide donor species is conjugated to an antibody that specifically binds to a phosphorylated product of a kinase reaction that is labeled with a suitable acceptor fluorophore. This antibody-mediated interaction brings the lanthanide donor and the acceptor into proximity such that resonance energy transfer can take place, resulting in a detectible increase in the FRET signal.

The kinase reactions were performed in 384 well microtiter plates in a total reaction volume of 9.05 µL. The assay plates were prepared with 0.05 µL per well of test compound in the appropriate test concentration, as described under "preparation of compound dilutions". The reactions were started by combining 4.5 µL of ATP solution with 4.5 µL of enzyme-substrate mix (consisting of kinase and substrate). The final concentrations in the kinase reactions were 35 mM Tris/HCl, 1 mM DTT, 0.025% Tween20, 10 µM sodium orthovanadate, 0.25% BSA, 0.6% DMSO, 10 mM MgCl$_2$, 3 mM MnCl$_2$, 2 µM ATP, 50 nM Fluorescein-PolyEAY, and 0.3 nM enzyme.

The reactions were incubated for 60 minutes at room temperature and stopped by adding 4.5 µL of stop buffer (50 mM EDTA, 0.04% NP40, 20 mM Tris/HCl).

Subsequently 4.5 µL of detection mix (50 mM Tris/HCl, 2 mM DTT, 0.05% Tween20, 20 µM sodium orthovanadate, 1% BSA, 1.72 µg/mL Tb-PY20 antibody) were added to the stopped reactions. After 30 minutes incubation at room temperature, the plates were measured in a BMG Pherastar fluorescence reader. The effect of compound on the enzymatic activity was in all assays obtained from the linear progress curves and determined from one reading (end point measurement). Results are summarized in Table 1 below.

Preparation of Compound Dilutions

Test compounds were dissolved in DMSO (10 mM) and transferred into 1.4 mL flat bottom or V-shaped Matrix tubes carrying a unique 2D matrix. The stock solutions were stored at –20° C. if not used immediately. For the test procedure the vials were defrosted and identified by a scanner whereby a working sheet was generated that guided the subsequent working steps.

Compound dilutions were made in 96 well plates. This format enabled the assay of maximally 40 individual test compounds at 8 concentrations (single points) including 4 reference compounds. The dilution protocol included the production of "pre-dilution plates", "master plates" and "assay plates".

Pre-dilution plates: 96 polypropylene well plates were used as pre-dilution plates. A total of 4 pre-dilution plates were prepared including 10 test compounds each on the plate positions A1-A10, one standard compound at A11 and one DMSO control at A12. All dilution steps were done on a HamiltonSTAR robot.

Master plates: 100 µL of individual compound dilutions including standard compound and controls of the 4 "pre-dilution plates" were transferred into a 384 "master plate" including the following concentrations 1'820, 564, 182, 54.6, 18.2, 5.46, 1.82 and 0.546 µM, respectively in 90% of DMSO.

Assay plates: Identical "assay plates" were then prepared by pipetting 50 nL each of compound dilutions of the "master plates" into 384-well "assay plates" by means of a Humming-Bird 384-channel dispenser. These plates were used directly for the assay which was performed in a total volume of 9.05 µL. This led to a final compound concentration of 10, 3.0, 1.0, 0.3, 0.1, 0.03, 0.01 and 0.003 µM and a final DMSO concentration of 0.5% in the assay.

TABLE 1

| Example | c-Met $IC_{50}$ [uM] |
|---|---|
| 1 | 0.0086 |
| 2 | <0.003 |
| 3 | 0.0052 |
| 4 | 0.68 |
| 5 | <0.003 |
| 6 | 0.0045 |
| 7 | 0.0041 |
| 8 | 0.0057 |
| 9 | 0.0029 |
| 10 | <0.003 |
| 11 | 0.0036 |
| 12 | 0.008 |
| 13 | <0.003 |
| 14 | 0.0079 |
| 15 | 0.0054 |
| 16 | 0.0017 |
| 17 | 0.024 |
| 18 | 0.0083 |
| 19 | 0.0071 |
| 20 | 0.027 |
| 21 | 0.019 |
| 22 | 0.014 |
| 23 | 0.015 |
| 24 | 0.004 |
| 25 | 0.015 |
| 26 | 0.026 |
| 27 | 0.073 |
| 28 | 0.017 |
| 29 | 0.055 |
| 30 | 0.0066 |
| 31 | 0.0082 |
| 32 | 0.0074 |
| 33 | 0.014 |
| 34 | 0.01 |
| 35 | 0.0099 |
| 36 | 0.011 |
| 37 | 0.058 |
| 38 | 0.031 |
| 39 | 0.084 |
| 40 | 0.039 |
| 41 | 0.023 |
| 42 | 0.049 |
| 43 | 0.084 |
| 44 | 0.014 |
| 45 | 0.17 |
| 46 | 0.03 |
| 47 | 0.015 |
| 48 | 0.14 |
| 49 | 0.016 |
| 50 | 0.0083 |
| 51 | 0.022 |
| 52 | <0.003 |
| 53 | 0.0052 |
| 54 | 0.02 |
| 55 | 0.029 |

TABLE 1-continued

| Example | c-Met $IC_{50}$ [uM] |
|---|---|
| 56 | 0.027 |
| 57 | 0.017 |
| 58 | 0.0027 |
| 59 | 0.003 |
| 60 | 0.0026 |

C-Met Dependent Cellular Assays

A number of compounds of the present invention were assayed in a c-Met dependent proliferation and phosphorylation assay as follows.

GTL-16 proliferation assay: the MET-amplified gastric cancer cell line GTL-16 was grown under standard cell culture conditions in DMEM [Dulbecco's Modified Eagle Medium] (high glucose) supplemented with 10% heat-inactivated fetal calf serum and 2 mM L-glutamine. For proliferation assays, cells were seeded at 3000 per well in 96-well-plates. 24 h later, a 10-point dilution series of each compound (3-fold steps, ranging from 1 mM to 0.05 mM) was prepared in DMSO. Compound were then diluted 1000-fold in growth media in two steps and added to cells in triplicates, resulting in a final volume of 100 mL per well and maximal final compound concentrations of 1 mM. A DMSO-only control was included. Cells were incubated for 72 h and the amount of viable cells was then measured by adding 20 mL of MTS reagent (CellTiter 96® AQueous Non-Radioactive Cell Proliferation Assay, Promega), further incubation for 30', and reading the optical density at 490 nm. Calculation of IC50 values from this data was done using the curve-fitting software XLFit 4.3.2

GTL-16 c-Met autophosphorylation measured by AlphaScreen® detection: the human MET-amplified gastric cancer cells GTL-16 were plated in 384-well plates at a density of 10'000 cells in 20 ul complete growth medium (DMEM high glucose supplemented with 10% (v/v) heat inactivated fetal calf serum and of 1 mM sodium pyruvate) and were incubated at 37% C/5% CO2/95% humidity for 20 h. The cells were washed and the 30 ul assay buffer (DMEM high glucose, 1 mM sodium pyruvate, 0.1% bovine serum albumine) was added. Compounds were diluted in 384-well compound plates to obtain 8-point serial dilutions for 40 test compounds in 90% DMSO, as well as a reference compound plus 16 high- and 16 low (inhibited) controls. These compound plates were prediluted 1:200 in assay buffer into a compound predilution plate and 10 ul of prediluted compound solution were transferred to the cell plate using a 384-well pipettor, resulting in a final DMSO concentration of 0.11%. Cells were incubated for 1 h at 37% C/5% CO2/95% humidity. The supernatant was removed, the cells were lysed in 25 ul of RIPA [radio immuno precipitation assay] lysis buffer supplemented with 2 mM sodium vanadate and a protease inhibitor cocktail, and cell plates were stored at −80° C.

For detection of p-c-Met, an AlphaScreen®-based assay was used. AlphaScreen® (Amplified Luminescent Proximity Homogeneous Assay, ALPHA, Perkin Elmer, U.S.A) is a non-radioactive bead-based proximity assay technology to study biomolecular interactions in a homogenous microtiter plate format. This technique has been adapted to measure the phosphorylation of endogenous cellular proteins in cell lysates by the use of specific antibody pairs against the total protein and a phospho-specific epitope. 5 ul of cell lysate was transferred to 384-well low volume Proxiplates for detection using a 384-well pipettor. First, 5 ul of a premix of an anti-c-

Met antibody (0.25 ug/ml f.c.), a biotinylated PY20 antibody (phosphotyrosine antibody, 0.05 ug/ml f.c.) and AlphaScreen® Protein A-coupled acceptor beads (10 ug/ml f.c.) in RIPA buffer supplemented with 0.25% (v/w) TOP BLOCK, 2 mM sodium vanadate, and a protease inhibitor cocktail and was added, the plate was sealed, and incubated on a plate shaker for 2 hours at room temperature. Second, 2 ul of dilution buffer containing AlphaScreen® Streptavidin-coated donor beads (10 ug/ml f.c.) in RIPA buffer was added, and the plate was incubated on plate shaker as above for a further 2 hours. The plate was read on an AlphaScreen® compatible plate reader, using standard AlphaScreen® settings. Results are summarized in Table 2 below.

TABLE 2

| | GTL-16 IC$_{50}$ [uM] | |
| --- | --- | --- |
| Example | proliferation | c-Met phosphorylation |
| 1 | 0.0091 | <0.003 |
| 2 | 0.0017 | 0.0027 |
| 3 | 0.006 | <0.003 |
| 5 | 0.0036 | <0.003 |
| 6 | 0.0116 | 0.003 |
| 7 | 0.0064 | 0.0021 |
| 8 | 0.0155 | <0.003 |
| 9 | 0.01 | 0.0022 |
| 10 | 0.0146 | <0.003 |
| 11 | 0.0072 | 0.0044 |
| 13 | 0.0092 | 0.0025 |
| 15 | 0.018 | 0.0083 |
| 16 | 0.015 | 0.0055 |
| 17 | 0.02 | 0.014 |
| 18 | 0.0092 | na |
| 19 | 0.016 | <0.003 |
| 20 | 0.021 | 0.007 |
| 21 | 0.009 | <0.003 |
| 22 | 0.015 | 0.006 |
| 23 | 0.0085 | 0.0033 |
| 24 | 0.0098 | 0.004 |
| 25 | 0.013 | 0.008 |
| 26 | 0.066 | 0.010 |
| 27 | 0.173 | 0.003 |
| 28 | 0.026 | 0.011 |
| 29 | 0.136 | 0.025 |
| 30 | 0.037 | <0.003 |
| 31 | 0.015 | 0.0047 |
| 32 | 0.025 | <0.003 |
| 33 | 0.046 | 0.009 |
| 34 | 0.065 | 0.007 |
| 35 | 0.045 | 0.008 |
| 36 | 0.025 | <0.003 |
| 40 | 0.147 | 0.011 |
| 41 | 0.049 | <0.003 |
| 42 | 0.193 | 0.039 |
| 44 | 0.133 | 0.031 |
| 46 | 0.047 | 0.015 |
| 47 | 0.019 | 0.0055 |
| 48 | 0.168 | 0.035 |
| 49 | 0.029 | 0.0065 |
| 50 | 0.011 | 0.0027 |
| 51 | 0.016 | 0.008 |
| 52 | 0.011 | 0.0022 |
| 53 | 0.022 | 0.0044 |
| 54 | 0.036 | <0.003 |
| 56 | 0.049 | 0.007 |
| 57 | 0.036 | 0.009 |
| 58 | 0.0071 | 0.0037 |
| 59 | 0.0056 | 0.0036 |
| 60 | 0.0048 | 0.0023 |

Solubility

A number of compounds of the present invention were assayed in a solubility assay at pH 7 and in fasted state simulated intestinal fluid (FaSSIF).

Solubility of the compounds was determined by suspending about 0.3 to 1.0 mg of drug substance in 0.1 mL of phosphate buffer at pH 7 and respectively FaSSIF.

Buffer pH 7 was obtained from MERCK as Tritisol® Phosphate Buffer. The Medium to Simulate the Fasted State Upper Small Intestine (Fasted State Simulated Intestinal Fluid) or FaSSIF was developed according to J. Dressmann publication Jantratid Ekarat; Janssen Niels; Reppas Christos; Dressman Jennifer B Dissolution media simulating conditions in the proximal human gastrointestinal tract: an update. Pharmaceutical research (2008), 25(7), 1663-76.

Composition from the FaSSIF is described in the following Table 3.

TABLE 3

| Composition | |
| --- | --- |
| Sodium taurocholate (mM) | 3 |
| Lecithin (mM) | 0.2 |
| Maleic acid (mM) | 19.12 |
| Sodium hydroxide (mM) | 34.8 |
| Sodium chloride (mM) | 68.62 |
| pH | 6.5 |
| Osmolality (mOsm kg$^{-1}$) | 180 × 10 |
| Buffer capacity (mmol l$^{-1}$ ΔpH$^{-1}$) | 10 |

The sodium taurocholate and sodium chloride are first dissolved in 400 mL of purified water followed by addition of 1 mL of 1 N HCl. After stirring for 30 min, the lecithin is added and the mixture is sonicated for 30 min. The solution is stirred for 2 hours before the addition of maleic acid and 500 mL water. The solution is then stirred for overnight and the pH is adjusted to 6.8 the next morning with 1 N NaOH and the total volume is adjusted to 1 liter. The final solution is clear and is stored at 4° C. when not used.

The suspensions or solutions were stirred over night at room temperature. After separation of the un-dissolved part by filtration (centrifugation using 0.45 μm PVDF or PTFE filters), the solutions were if necessary, diluted with acetonitrile to obtain concentrations below 1.0 mg/mL prior to UPLC analysis. Samples were then analyzed by UPLC to get the concentrations level of compound in the different media. Prior to analysis a method has been developed for each compound with an according calibration.

UPLC parameters: Column Aquity 50*2.1 mm C18 1.7ym; Column temperature: 40° C.; mobile phase A: water MilliQ+ 0.1% TFA and B acetonitrile, gradient grade, +0.1% TFA. Results are summarized in Table 4 below.

TABLE 4

| | Solubility | |
| --- | --- | --- |
| Example | Buffer pH 7 (mg/mL) | FaSSIF (mg/mL) |
| 2 | 0.029 | 0.289 |
| 5 | 0.091 | 0.164 |
| 7 | 0.248 | 0.172 |
| 11 | 0.032 | 1.354 |
| 28 | 0.117 | 0.374 |

The invention claimed is:
1. A compound of the formula (I),

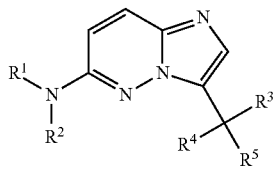

wherein
R¹ and R² together with the nitrogen to which they are attached form a 6 membered saturated monocyclic group comprising 1 ring N atom to which R¹ and R² are attached, and optionally 1 additional ring N atom, wherein said monocyclic group is unsubstituted or substituted one or more times by a substituent independently selected from $C_1$-$C_7$-alkyl, $C_3$-$C_{12}$-cycloalkyl, halo-$C_1$-$C_7$-alkyl, amino-$C_1$-$C_7$-alkyl, $C_1$-$C_7$-alkylcarbonyl, $C_1$-$C_7$-alkoxycarbonyl, formyl, amino-carbonyl, amino-$C_1$-$C_7$-alkyl-carbonyl, halo-$C_1$-$C_7$-alkylcarbonyl, halo-$C_1$-$C_7$-alkoxycarbonyl, phenyl, pyridyl, oxo;
R³ is hydrogen, hydroxy, halogen or $C_1$-$C_7$-alkyl;
R⁴ is hydrogen, halogen or $C_1$-$C_7$-alkyl;
R⁵ is indazolyl or quinolinyl, each being substituted by at least one halogen atom;
or a pharmaceutically acceptable salt or N-oxide thereof.
2. The compound of claim 1, wherein,
R¹ and R² together with the nitrogen to which they are attached form a group:

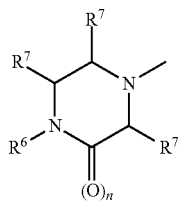

wherein,
n is 0 or 1;
R⁶ is hydrogen or a group selected from $C_1$-$C_7$-alkyl, $C_3$-$C_{12}$-cycloalkyl, halo-$C_1$-$C_7$-alkyl, amino-$C_1$-$C_7$-alkyl, $C_1$-$C_7$-alkylcarbonyl, $C_1$-$C_7$-alkoxycarbonyl, formyl, amino-carbonyl, amino-$C_1$-$C_7$-alkyl-carbonyl, halo-$C_1$-$C_7$-alkylcarbonyl, halo-$C_1$-$C_7$-alkoxycarbonyl, phenyl, pyridyl; and
each R⁷ is independently selected from hydrogen, unsubstituted $C_1$-$C_7$-alkyl or substituted $C_1$-$C_7$-alkyl selected from halo-$C_1$-$C_7$-alkyl, amino-$C_1$-$C_7$-alkyl, hydroxy-$C_1$-$C_7$-alkyl,
or a pharmaceutically acceptable salt thereof.
3. The compound of claim 2, wherein,
R⁵ is indazolyl or quinolinyl substituted by at least one halo substituent,
or a pharmaceutically acceptable salt thereof.
4. The compound of claim 3, wherein,
R⁵ is indazolyl or quinolinyl substituted by at least one fluoro substituent,
or a pharmaceutically acceptable salt thereof.
5. The compound of claim 4, wherein,
R⁵ is indazolyl or quinolinyl substituted by one or two fluoro substituents,
or a pharmaceutically acceptable salt thereof.
6. The compound of claim 1 selected from,
(rac)-4-{3-[1-(5,7-Difluoro-quinolin-6-yl)-ethyl]-imidazo[1,2-b]pyridazin-6-yl}-1-methyl-piperazin-2-one;
4-{3-[(S)-1-(5,7-Difluoro-quinolin-6-yl)-ethyl]-imidazo[1,2-b]pyridazin-6-yl}-1-methyl-piperazin-2-one;
(rac)-4-{3-[1-(5,7-Difluoro-quinolin-6-yl)-ethyl]-imidazo[1,2-b]pyridazin-6-yl}-piperazin-2-one;
4-{3-[(R)-1-(5,7-Difluoro-quinolin-6-yl)-ethyl]-imidazo[1,2-b]pyridazin-6-yl}-piperazin-2-one;
4-{3-[(S)-1-(5,7-Difluoro-quinolin-6-yl)-ethyl]-imidazo[1,2-b]pyridazin-6-yl}-piperazin-2-one;
(rac)-5,7-Difluoro-6-[1-(6-piperazin-1-yl-imidazo[1,2-b]pyridazin-3-yl)-ethyl]-quinoline;
5,7-Difluoro-6-[(S)-1-(6-piperazin-1-yl-imidazo[1,2-b]pyridazin-3-yl)-ethyl]-quinoline;
(rac)-5,7-Difluoro-6-{1-[6-(4-methyl-piperazin-1-yl)-imidazo[1,2-b]pyridazin-3-yl]-ethyl}-quinoline;
5,7-Difluoro-6-{(S)-1-[6-(4-methyl-piperazin-1-yl)-imidazo[1,2-b]pyridazin-3-yl]-ethyl}-quinoline;
(rac)-1-(4-{3-[1-(5,7-Difluoro-quinolin-6-yl)-ethyl]-imidazo[1,2-b]pyridazin-6-yl}-piperazin-1-yl)-ethanone;
1-(4-{3-[(S)-1-(5,7-Difluoro-quinolin-6-yl)-ethyl]-imidazo[1,2-b]pyridazin-6-yl}-piperazin-1-yl)-ethanone;
(rac)-4-{3-[1-(5,7-Difluoro-quinolin-6-yl)-ethyl]-imidazo[1,2-b]pyridazin-6-yl}-piperazine-1-carbaldehyde;
4-{3-[(S)-1-(5,7-Difluoro-quinolin-6-yl)-ethyl]-imidazo[1,2-b]pyridazin-6-yl}-piperazine-1-carbaldehyde;
(rac)-4-{3-[1-(5,7-Difluoro-quinolin-6-yl)-ethyl]-imidazo[1,2-b]pyridazin-6-yl}-piperazine-1-carboxylic acid methyl ester;
(rac)-4-{3-[1-(5,7-Difluoro-quinolin-6-yl)-ethyl]-imidazo[1,2-b]pyridazin-6-yl}-piperazine-1-carboxylic acid amide;
4-{3-[(S)-1-(5,7-Difluoro-quinolin-6-yl)-ethyl]-imidazo[1,2-b]pyridazin-6-yl}-piperazine-1-carboxylic acid amide;
(rac)-1-(4-{3-[1-(5,7-Difluoro-quinolin-6-yl)-ethyl]-imidazo[1,2-b]pyridazin-6-yl}-piperazin-1-yl)-2,2,2-trifluoro-ethanone;
(rac)-4-{3-[1-(5,7-Difluoro-quinolin-6-yl)-ethyl]-imidazo[1,2-b]pyridazin-6-yl}-3-methyl-piperazin-2-one;
(rac)-4-{3-[1-(5,7-Difluoro-quinolin-6-yl)-ethyl]-imidazo[1,2-b]pyridazin-6-yl}-1-cyclopentylpiperazin-2-one;
(rac)-4-{3-[1-(5,7-Difluoro-quinolin-6-yl)-ethyl]-imidazo[1,2-b]pyridazin-6-yl}-1,3-dimethylpiperazin-2-one;
(rac)-4-{3-[1-(5,7-Difluoro-quinolin-6-yl)-ethyl]-imidazo[1,2-b]pyridazin-6-yl}-1-phenylpiperazin-2-one;
(rac)-4-{3-[1-(5,7-Difluoro-quinolin-6-yl)-ethyl]-imidazo[1,2-b]pyridazin-6-yl}-5-methylpiperazin-2-one;
(rac)-4-{3-[1-(5,7-Difluoro-quinolin-6-yl)-ethyl]-imidazo[1,2-b]pyridazin-6-yl}-6-methylpiperazin-2-one;
(rac)-4-{3-[1-(5,7-Difluoro-quinolin-6-yl)-ethyl]-imidazo[1,2-b]pyridazin-6-yl}-1-(pyridin-2-yl)piperazin-2-one;
4-{3-[(S)-1-(6-Fluoro-1-methyl-1H-indazol-5-yl)-ethyl]-imidazo[1,2-b]pyridazin-6-yl}-1-methyl-piperazin-2-one;
(rac)-4-{3-[1-(6-Fluoro-1-methyl-1H-indazol-5-yl)-ethyl]-imidazo[1,2-b]pyridazin-6-yl}-piperazin-2-one;

4-{3-[(S)-1-(6-Fluoro-1-methyl-1H-indazol-5-yl)-ethyl]-imidazo[1,2-b]pyridazin-6-yl}-piperazin-2-one;
1-(4-{3-[(S)-1-(6-Fluoro-1-methyl-1H-indazol-5-yl)-ethyl]-imidazo[1,2-b]pyridazin-6-yl}-piperazin-1-yl)-ethanone; 4-[3-(5,7-Difluoro-quinolin-6-ylmethyl)-imidazo[1,2-b]pyridazin-6-yl]-1-methyl-piperazin-2-one;
4-[3-(5,7-Difluoro-quinolin-6-ylmethyl)-imidazo[1,2-b]pyridazin-6-yl]-piperazin-2-one;
5,7-Difluoro-6-(6-piperazin-1-yl-imidazo[1,2-b]pyridazin-3-ylmethyl)-quinoline;
5,7-Difluoro-6-[6-(4-methyl-piperazin-1-yl)-imidazo[1,2-b]pyridazin-3-ylmethyl]-quinoline;
1-{4-[3-(5,7-Difluoro-quinolin-6-ylmethyl)-imidazo[1,2-b]pyridazin-6-yl]-piperazin-1-yl}-ethanone;
4-[3-(5,7-Difluoro-quinolin-6-ylmethyl)-imidazo[1,2-b]pyridazin-6-yl]-piperazine-1-carbaldehyde;
4-[3-(5,7-Difluoro-quinolin-6-ylmethyl)-imidazo[1,2-b]pyridazin-6-yl]-piperazine-1-carboxylic acid methyl ester;
4-[3-(7-Fluoro-quinolin-6-ylmethyl)-imidazo[1,2-b]pyridazin-6-yl]-1-methyl-piperazin-2-one;
4-[3-(7-Fluoro-quinolin-6-ylmethyl)-imidazo[1,2-b]pyridazin-6-yl]-piperazin-2-one;
1-{4-[3-(7-Fluoro-quinolin-6-ylmethyl)-imidazo[1,2-b]pyridazin-6-yl]-piperazin-1-yl}-ethanone;
(rac)-4-{3-[1-(7-Fluoro-quinolin-6-yl)-ethyl]-imidazo[1,2-b]pyridazin-6-yl}-1-methyl-piperazin-2-one;
(rac)-4-{3-[1-(7-Fluoro-quinolin-6-yl)-ethyl]-imidazo[1,2-b]pyridazin-6-yl}-piperazin-2-one;
(rac)-1-(4-{3-[1-(7-Fluoro-quinolin-6-yl)-ethyl]-imidazo[1,2-b]pyridazin-6-yl}-piperazin-1-yl)-ethanone;
4-[3-(5-Fluoro-quinolin-6-ylmethyl)-imidazo[1,2-b]pyridazin-6-yl]-1-methyl-piperazin-2-one;
4-[3-(5-Fluoro-quinolin-6-ylmethyl)-imidazo[1,2-b]pyridazin-6-yl]-piperazin-2-one;
1-{4-[3-(5-Fluoro-quinolin-6-ylmethyl)-imidazo[1,2-b]pyridazin-6-yl]-piperazin-1-yl}-ethanone;
(rac)-4-{3-[1-(5-Fluoro-quinolin-6-yl)-ethyl]-imidazo[1,2-b]pyridazin-6-yl}-1-methyl-piperazin-2-one;
(rac)-4-{3-[1-(5-Fluoro-quinolin-6-yl)-ethyl]-imidazo[1,2-b]pyridazin-6-yl}-piperazin-2-one;
(rac)-1-(4-{3-[1-(5-Fluoro-quinolin-6-yl)-ethyl]-imidazo[1,2-b]pyridazin-6-yl}-piperazin-1-yl)-ethanone;
(rac)-4-(3-(1-(4,6-difluoro-1-methyl-1H-indazol-5-yl)ethyl)imidazo[1,2-b]pyridazin-6-yl)-1-methylpiperazin-2-one;
4-{3-[(S)-1-(4,6-Difluoro-1-methyl-1H-indazol-5-yl)-ethyl]-imidazo[1,2-b]pyridazin-6-yl}-1-methyl-piperazin-2-one;
(rac)-4-{3-[1-(4,6-difluoro-1-methyl-1H-indazol-5-yl)-ethyl]-imidazo[1,2-b]pyridazine-}-piperidin-2-one;
4-{3-[(S)-1-(4,6-Difluoro-1-methyl-1H-indazol-5-yl)-ethyl]-imidazo[1,2-b]pyridazin-6-yl}-piperazin-2-one;
1-(4-{3-[(S)-1-(4,6-Difluoro-1-methyl-1H-indazol-5-yl)-ethyl]-imidazo[1,2-b]pyridazin-6-yl}-piperazin-1-yl)-ethanone;
4-[3-(4,6-Difluoro-1-methyl-1H-indazol-5-ylmethyl)-imidazo[1,2-b]pyridazin-6-yl]-piperazin-2-one;
1-(4-(3-((4,6-difluoro-1-methyl-1H-indazol-5-yl)methyl)imidazo[1,2-b]pyridazin-6-yl)piperazin-1-yl)ethanone;
(rac)-4-(3-(1-(4,6-difluoro-1-isopropyl-1H-indazol-5-yl)ethyl)imidazo[1,2-b]pyridazin-6-yl)-1-methylpiperazin-2-one;
(rac)-4-(3-(1-(4,6-difluoro-1-isopropyl-1H-indazol-5-yl)ethyl)imidazo[1,2-b]pyridazin-6-yl)piperazin-2-one;
(rac)-4-{3-[(S)-1-(5,7-Difluoro-quinolin-6-yl)-ethyl]-imidazo[1,2-b]pyridazin-6-yl}-3-methyl-piperazin-2-one;
(R)-4-{3-[(S)-1-(5,7-Difluoro-quinolin-6-yl)-ethyl]-imidazo[1,2-b]pyridazin-6-yl}-3-methyl-piperazin-2-one;
(S)-4-{3-[(S)-1-(5,7-Difluoro-quinolin-6-yl)-ethyl]-imidazo[1,2-b]pyridazin-6-yl}-3-methyl-piperazin-2-one.

7. The compound of claim 1 in free form or in pharmaceutically acceptable salt form for use as pharmaceutical.

8. A pharmaceutical composition comprising a therapeutically effective amount of a compound of claim 1 in free form or in pharmaceutically acceptable salt form as active ingredient, and one or more pharmaceutically acceptable carrier material(s) and/or diluents.

9. A combined pharmaceutical composition, adapted for simultaneous or sequential administration, comprising a therapeutically effective amount of a compound of claim 1 in free form or in pharmaceutically acceptable salt form, therapeutically effective amount(s) of one or more combination partners, and one or more pharmaceutically acceptable carrier material(s) and/or diluents.

* * * * *